US008591892B2

(12) United States Patent
Alinari et al.

(10) Patent No.: US 8,591,892 B2
(45) Date of Patent: Nov. 26, 2013

(54) FTY720 INCREASES CD74 EXPRESSION AND SENSITIZES CANCER CELLS TO ANTI-CD74 ANTIBODY-MEDIATED CELL DEATH

(75) Inventors: Lapo Alinari, Dublin, OH (US); Robert A. Baiocchi, Dublin, OH (US); Natarajan Muthusamy, Galloway, OH (US); Hans J. Hansen, Picayune, MS (US); David M. Goldenberg, Mendham, NJ (US)

(73) Assignees: The Ohio State University, Columbus, OH (US); Immunomedics, Inc., Morris Plains, NJ (US)

( * ) Notice: Subject to any disclaimer, the term of this patent is extended or adjusted under 35 U.S.C. 154(b) by 0 days.

(21) Appl. No.: 13/551,866

(22) Filed: Jul. 18, 2012

(65) Prior Publication Data
US 2013/0022541 A1 Jan. 24, 2013

Related U.S. Application Data

(60) Provisional application No. 61/508,852, filed on Jul. 18, 2011.

(51) Int. Cl.
*A61K 39/395* (2006.01)
(52) U.S. Cl.
USPC ...................................................... 424/130.1
(58) Field of Classification Search
None
See application file for complete search history.

(56) References Cited

U.S. PATENT DOCUMENTS

| | | | |
|---|---|---|---|
| 4,816,567 | A | 3/1989 | Cabilly et al. |
| 5,618,920 | A | 4/1997 | Robinson et al. |
| 5,693,762 | A | 12/1997 | Queen et al. |
| 5,846,534 | A | 12/1998 | Waldmann et al. |
| 6,051,230 | A | 4/2000 | Thorpe et al. |
| 6,306,393 | B1 | 10/2001 | Goldenberg et al. |
| 6,653,104 | B2 | 11/2003 | Goldenberg et al. |
| 7,312,318 | B2 | 12/2007 | Hansen et al. |
| 7,585,491 | B2 | 9/2009 | Govindan |
| 2002/0018749 | A1 | 2/2002 | Hudson et al. |
| 2002/0041847 | A1 | 4/2002 | Goldenberg |
| 2003/0013122 | A1 | 1/2003 | Bucala et al. |
| 2010/0022655 | A1 | 1/2010 | Byrd et al. |

FOREIGN PATENT DOCUMENTS

| | | |
|---|---|---|
| WO | 98/50432 | 11/1998 |
| WO | 00/67795 | 11/2000 |
| WO | 00/74718 | 12/2000 |

OTHER PUBLICATIONS

Liu et al (Clin Cancer Res, 2010, 16(12): 3182-3192).*
Chang et al (Blood, 2005, 106(13): 4308-4314).*
Ohsawa et al (J Clin Pathol, 1994, 47(10): Abstract).*
Abdel-Raheem et al., "Severe Evan's syndrome secondary to interleukin-2 therapy: treatment with chimeric monoclonal anti-CD20 antibody", Ann Hematol. Sep. 2001;80(9):543-5.
Alinari et al., "FTY720-induced blockage of autophagy enhances anticancer efficacy of milatuzumab in mantle cell lymphoma: is FTY720 the next autophagy-blocking agent in lymphome treatment?", Autophagy. Mar. 2012;8(3):416-7.
Alinari et al., "FTY720 increases CD74 expression and sensitizes mantle cell lymphoma cells to milatuzumab-mediated cell death", Blood. Dec. 22, 2011;118(26):6893-903.
Banapour et al.; "Characterization and epitope mapping of a human monoclonal antibody reactive with the envelope glycoprotein of human immunodeficiency virus", J Immunol. Dec. 15, 1987;139(12):4027-33.
Bendig, M., "Humanization of Rodent Monoclonal Antibodies by CDR Grafting", Academic Press Inc., New York, NY, vol. 8, (1995), pp. 83-93.
Burgess et al., "Possible dissociation of the heparin-binding and mitogenic activities of heparin-binding (acidic fibroblast) growth factor-1 from its receptor-binding activities by site-directed mutagenesis of a single lysine residue". J. Cell Biol. 111:2129-2138 (1990).
Colman, P., "Effects of amino acid sequence changes on antibody-antigen interactions", Res. Immunol. 1994, 145:33-36.
Datta et al., "Expression of MHC class II-associated invariant chain (Ii;CD74) in thymic epithelial neoplasms", Appl Immunohistochem Mol Morphol. Sep. 2000:8(3):210-215.
Ellis et al , "Engineered anti-CD38 monoclonal antibodies for immunotherapy of multiple myeloma", J Immunol. Jul. 15, 1995;155(2):925-37.
Gondo et al., "HLA class II antigen associated invariant chain gene expression in malignant lymphoma", Br. J. Haematol. Dec. 1987;61(4):413-7.
Griffiths et al., "Cure of SCID Mice Bearing Human B-Lymphoma Xenografts by an Anti-CD74 Antibody-Anthracycline Drug Conjugate", vol. 9, 6567-6571, Dec. 15, 2003.
Hansen et al., "Internalization and catabolism of radiolabelled antibodies to the MHC class-II invariant chain by B-cell lymphomas", Biochem. J. 1996, 320:293-300.
Ibragimova et al., "Stability of the beta-sheet of the WW domain: A molecular dynamics simulation study", Biophys J. Oct. 1999:77(4):2191-8.
Inukai et al., "Expression of HLA-DR and its enhancing molecules in muscle fibers in polymyositis"; Muscle Nerve. Mar. 2000;23(3):385-92.
Ioachim at al., "Lymphoid monoclonal antibodies reactive with lung tumors. Diagnostic applications" Am J Surg Pathol. Jan. 1996;20(1):64-71.
Ishigami et al., "Invariant chain expression in gastric cancer", Cancer Lett. Jul. 10, 2001;168(1):87-91.
Kolata, G., "Clinical promise with new hormones", Science 236:517-519 (1987).
Lazar et al., "Transforming growth factor alpha: an aromatic side chain at position 38 is essential for biological activity", Mol. Cell. Biol. 8(3):1247-1252 (1988).
Lazova et al., "LN-2 (CD74). A marker to distinguish atypical fibroxanthoma from malignant fibrous histiocytoma", Cancer. Jun. 1, 1997;79(11):2115-24.

(Continued)

Primary Examiner — Sean Aeder
(74) Attorney, Agent, or Firm — Richard A. Nakashima

(57) ABSTRACT

Disclosed herein are methods and compositions comprising fingolimod and anti-CD74 antibodies or fragments thereof. In preferred embodiments, the fingolimod increases the expression of CD74 in target cells and increases the sensitivity of the cells to the cytotoxic effects of the anti-CD74 antibodies. The compositions and methods are of use to treat diseases involving $CD74^+$ cells, such as cancer cells, autoimmune disease cells or immune dysfunction disease cells.

48 Claims, 14 Drawing Sheets

(56) References Cited

OTHER PUBLICATIONS

Leung et al., "Chimerization of LL2, a Rapidly Internalizing Antibody Specific for B Cell Lymphoma", Hybridoma 13(6):469-76 (1994).

Leung et al., "Construction and characterization of a humanized, internalizing, b-cell (CD22)-specific, leukemia/lymphma antibody, LL2", Mol. Immunol. 32(17/18):1413-1427 (1995).

Liu et al., "FTY720 shows promising in vitro and in vivo preclinical activity by downmodulating Cyclin D1 and phospho-Akt in mantle cell lymphoma", Clin Cancer Res. Jun. 15, 2010;16(12):3182-92.

Marks et al., "By-passing immunization. Human antibodies from V-gene libraries displayed on phage", J Mol Biol. Dec. 5, 1991;222(3):581-97.

Moller et al., "CD74", J. Biol. Regul. Homeost. Agents Oct.-Dec. 2000;14(4):299-301.

Ochakovskaya et al., "Therapy of Disseminated B-Cell Lymphoma Xenografts in Severe Combined Immunodeficient Mice with an Anti-CD74 Antibody Conjugated with (111)Indium, (67)Gallium, or (90)Yttrium", Clin. Cancer Res. 7(6):1505-1510 (2001).

Ong et al., "Cell surface expression and metabolism of major histocompatibility complex class II invariant chain (CD74) by diverse cell lines", Immunology. Oct. 1999;98(2)296-302.

Orlandi et al., "Cloning immunoglobulin variable domains for expression by the polymerase chain reaction", Proc. Natl. Acad. Sci. USA 86:3833-3837 (1989).

Oster et al., "Erythropoietin for the Treatment of Anemia of Malignancy Associated with Neoplastic Bone Marrow Infiltration", J. Clin. Oncol., 8(6):956-962 (1990).

Pawlak-Byczkowska et al. "Two new monoclonal antibodies, EPB-1 and EPB-2, reactive with human lymphoma", Cancer Res. Aug. 15, 1989;49(16):4568-77.

Perez-Soler et al., "Use of Drug Carriers to Ameliorate the Therapeutic Index of Anthracycline Antibiotics", Chapter 19; ACS Symposium Series; American Chemical Society, Washington, DC 1994.

Qu et al., "Internalization and Cytotoxic Effects of a Humanized Anti-CD74 Antibody, LL1", Proc. Am. Assoc. Cancer Res 2002;43:255.

Roche et al,, "Cell surface HLA-DR-invariant chain complexes are targeted to endosomes by rapid internalization", Prot Natl Acad Sci USA. Sep. 15, 1993;90(18):8581-5.

Rudikoff et al., "Single amino acid substitution altering antigen-binding specificity", Proc. Natl. Acad. Sci. USA 1982; 79(6):1979-83.

Salopek et al., "Anti-CD20 Chimeric Monoclonal Antibody (Rituximab) for the Treatment of Recalcitrant, Life-Threatening Pemphigus Vulgaris: Implications for its Use in Other Autoimmune Antibody Mediated Diseases", J Investig Dermatol. 117(2):542, Abstract #916.

Shan et al., "Apoptosis of malignant human B cells by ligation of CD20 with monoclonal antibodies", Blood. Mar. 1, 1998;91(5):1644-52.

Shih et al., "Localization of an antibody to CD74 (MHC class II invariant chain) to human B cell lymphoma xenografts in nude mice", Cancer Immunol. Immunother. 49:208-216 (2000).

Tutt et al., "Monoclonal Antibody Therapy of B Cell Lymphoma: Signaling Activity on Tumor Cells Appears More Important Than Recruitment of Effectors", J. Immunol. 161(6):3176-85 (1998).

Wurflein et al., "Evaluating antibodies for their capacity to induce cell-mediated lysis of malignant B cells", Cancer Res Jul. 15, 1998;58(14):3051-8.

Young et al., "Expression profiling of renal epithelial neoplasms: a method for tumor classification and discovery of diagnostic molecular markers", Am J Pathol May 2001;158(5):1639-51.

\* cited by examiner

| Patient | Age/Sex | Variants of mantle cell lymphoma | Stage | Source of tumor cells | Previous therapy |
|---|---|---|---|---|---|
| 1 | 52M | Blastoid | IVB | PBMC | No |
| 2 | 60M | Blastoid | IVB | PBMC | Yes |
| 3 | 55F | Classic | IVB | LN | No |
| 4 | 59M | Classic | IVA | PBMC | No |
| 5 | 65M | Classic | IVB | PBMC | No |
| 6 | 63F | Blastoid | IVB | PBMC | YES |

FIG. 4B

FTY720 INCREASES CD74 EXPRESSION AND SENSITIZES CANCER CELLS TO ANTI-CD74 ANTIBODY-MEDIATED CELL DEATH

CROSS-REFERENCE TO RELATED APPLICATIONS

This application claims the benefit under 35 U.S.C. 119(e) of provisional application Ser. No. 61/508,852, filed Jul. 18, 2011, the entire text of which is incorporated herein by reference.

The instant application contains a Sequence Listing which has been submitted in ASCII format via EFS-Web and is hereby incorporated by reference in its entirety. Said ASCII copy, created on Jul. 17, 2012, is named IMM334US.txt and is 18,154 bytes in size.

FIELD OF THE INVENTION

The present invention concerns compositions and methods of therapeutic treatment of cancer and/or other diseases using anti-CD74 antibodies, antibody fragments, antibody fusion proteins or immunoconjugates. Preferably, the compositions and methods relate to use of FTY720 (fingolimod) or similar compounds, such as other modulators of the sphingosine 1-phosphate receptor, to increase expression of CD74 (also known as the invariant chain (Ii) of the HLA-DR complex) and to increase sensitivity of cancer cells to anti-CD74 antibodies, antibody fragments, antibody fusion proteins and/or immunoconjugates. In more preferred embodiments, the methods and compositions are effective to treat hematopoietic cancers, including but not limited to leukemias, lymphomas, mantle cell lymphoma, non-Hodgkin's lymphoma (NHL), multiple myeloma, chronic lymphocytic leukemia, acute lymphocytic leukemia, acute myelogenous leukemia, glioblastoma, follicular lymphoma and diffuse large B cell lymphoma. However, the skilled artisan will be aware that many types of cancers, such as colon cancer, pancreatic cancer, renal cancer, lung cancer, stomach cancer, breast cancer, prostate cancer, ovarian cancer and melanoma, express CD74 and any such cancer may be treated using the disclosed methods and compositions. The methods and compositions are also of use for other diseases associated with CD74 positive cells, such as autoimmune disease or immune dysregulation disease (e.g., graft-versus-host disease, organ transplant rejection).

BACKGROUND

The CD74 antigen is an epitope of the major histocompatibility complex (MHC) class II antigen invariant chain, Ii, present on the cell surface and taken up in large amounts of up to $8 \times 10^6$ molecules per cell per day (Hansen et al., 1996, Biochem. J., 320: 293-300). CD74 is present on the cell surface of B-lymphocytes, monocytes and histiocytes, human B-lymphoma cell lines, melanomas, T-cell lymphomas and a variety of other tumor cell types. (Hansen et al., 1996, Biochem. J., 320: 293-300) CD74 associates with $\alpha/\beta$ chain MHC II heterodimers to form MHC II $\alpha\beta$Ii complexes that are involved in antigen processing and presentation to T cells (Dixon et al., 2006, Biochemistry 45:5228-34; Loss et al., 1993, J Immunol 150:3187-97; Cresswell et al, 1996; Cell 84:505-7).

CD74 plays an important role in cell proliferation and survival. Binding of the CD74 ligand, macrophage migration inhibitory factor (MIF), to CD74 activates the MAP kinase cascade and promotes cell proliferation (Leng et al., 2003, J Exp Med 197:1467-76). Binding of MIF to CD74 also enhances cell survival through activation of NF-κB and Bcl-2 (Lantner et al., 2007, Blood 110:4303-11). MIF is a cytokine involved in the regulation of inflammation as well as in cell proliferation and survival of many different types of cells, including cancer and autoimmune disease cells (see, e.g., Leng et al., 2003, J Exp Med 197:1467-76; Bernhagen et al. 2007, Nature Med 12:587-96). CD74 acts in conjunction with CD44 to mediate the intracellular effects of MIF (Id.). MIF is known to suppress the action of the tumor-suppressor gene p53, resulting in promotion of cell growth and inhibition of apoptosis (Meyer-Siegler et al., 2006, J Immunol 177:8730-39). Numerous studies have demonstrated that reducing tumor MIF results in decreased cell proliferation, induction of apoptosis and reduction in the synthesis and secretion of other growth factors (Id.). Deactivation of MIF by antibodies or inhibition of MIF binding to CD74 has been shown to attenuate tumor growth and angiogenesis (Cournia et al., 2009, J Med Chem 53:416-24). MIF is also implicated in various inflammatory and autoimmune diseases, such as rheumatoid arthritis, atherosclerosis, asthma and systemic lupus (Id.)

In addition to inducing NF-κB activation, binding of MIF to CD74 up-regulates TAp63 expression, resulting in IL-8 secretion which in turn promotes cell survival (Shachar & Haran, 2011, Leuk Lymphoma 52:1446-54). TAp63 binds to the Bcl-2 promoter and induces the transcription of Bcl-2 mRNA and production of the Bcl-2 anti-apoptotic protein, which enhances cell survival (Id.). Thus, the MIF/CD74/NF-κB/Tap63 axis defines a novel anti-apoptotic pathway in mature B cells, shaping both the B cell repertoire and the immune response (Id.). Blocking of CD74 with anti-CD74 antibodies results in dramatic down-regulation of Bcl-2 expression, and augmentation of apoptosis (Id.). It now appears that the broad effects of anti-CD74 antibodies in inducing apoptosis of CD74+ cells in cancer and autoimmune disease are mediated at least in part through inhibition of MIF's promotion of cell proliferation and survival.

Antibodies against CD74 that have been reported to show efficacy against CD74-associated diseases include the anti-CD74 hLL1 antibody (milatuzumab) (Berkova et al., Expert Opin. Investig. Drugs 19:141-49; Burton et al., 2004, Clin Cancer Res 10:6605-11; Chang et al., 2005, Blood 106:4308-14; Griffiths et al., 2003, Clin Cancer Res 9:6567-71; Stein et al., 2007, Clin Cancer Res 13:5556s-63s; Stein et al., 2010, Blood 115:5180-90). However, despite the efficacy of such antibodies against cancer, some types of CD74 expressing cancers have been reported to be resistant to antibody therapy (see, e.g., Stein et al., 2010, Blood 115:5180-90). A need exists for more effective methods and compositions for therapeutic use of anti-CD74 antibodies.

Fingolimod (FTY720) is a synthetic analog of sphingosine that was developed as an immunosuppressive agent (Mandala et al., 2002, Science 296:346-349; Tedesco-Silva et al., 2005, Transplantation 79:1553-1560). Based on the results of a recent phase III clinical trial, FTY720 has been approved by the FDA as the first oral agent to treat relapsed multiple sclerosis (Cohen et al., 2010, N Engl J Med 362:402-41). The studies reported in the working Examples below demonstrate that FTY720 increases CD74 expression and sensitizes CD74 positive tumors, such as mantle cell lymphoma, to cell death mediated by anti-CD74 antibodies.

SUMMARY

The present invention concerns improved compositions and methods of use of anti-CD74 antibodies or antigen-binding antibody fragments. In preferred embodiments, the compositions and methods include fingolimod (FTY720), which may be administered prior to or concurrently with the anti-CD74 antibodies or fragments thereof. More preferably, the administration of FTY720 increases the expression of CD74 and enhances the sensitivity of cancer cells, autoimmune disease cells or immune dysfunction cells to the cytotoxic effects of anti-CD74 antibodies.

Many examples of anti-CD74 antibodies are known in the art and any such known antibody, fragment, immunoconjugate or fusion protein thereof may be utilized. In a preferred embodiment, the anti-CD74 antibody is an hLL1 antibody (also known as milatuzumab) that comprises the light chain complementarity-determining region (CDR) sequences CDR1 (RSSQSLVHRNGNTYLH; SEQ ID NO:1), CDR2 (TVSNRFS; SEQ ID NO:2), and CDR3 (SQSSHVPPT; SEQ ID NO:3) and the heavy chain variable region CDR sequences CDR1 (NYGVN; SEQ ID NO:4), CDR2 (WINPNTGEPTFDDDFKG; SEQ ID NO:5), and CDR3 (SRGKNEAWFAY; SEQ ID NO:6). A humanized LL1 (hLL1) anti-CD74 antibody suitable for use is disclosed in U.S. Pat. No. 7,312,318, incorporated herein by reference from Col. 35, line 1 through Col. 42, line 27 and FIG. 1 through FIG. 4. However, in alternative embodiments, other known anti-CD74 antibodies may be utilized, such as LS-B 1963, LS-B2594, LS-B1859, LS-B2598, LS-C5525, LS-C44929, etc. (LSBio, Seattle, Wash.); LN2 (BIOLEGEND®, San Diego, Calif.); PIN.1, SPM523, LN3, CerCLIP.1 (ABCAM®, Cambridge, Mass.); At14/19, Bu45 (SEROTEC®, Raleigh, N.C.); 1D1 (ABNOVA®, Taipei City, Taiwan); 5-329 (EBIOSCIENCE®, San Diego, Calif.); and any other anti-CD74 antibody known in the art.

The anti-CD74 antibody may be selected such that it competes with or blocks binding to CD74 of an LL1 antibody comprising the light chain CDR sequences CDR1 (RSSQSLVHRNGNTYLH; SEQ ID NO:1), CDR2 (TVSNRFS; SEQ ID NO:2), and CDR3 (SQSSHVPPT; SEQ ID NO:3) and the heavy chain variable region CDR sequences CDR1 (NYGVN; SEQ ID NO:4), CDR2 (WINPNTGEPTFDDDFKG; SEQ ID NO:5), and CDR3 (SRGKNEAWFAY; SEQ ID NO:6). Alternatively, the anti-CD74 antibody may bind to the same epitope of CD74 as an LL1 antibody. In still other alternatives, the anti-CD74 antibody may exhibit a functional characteristic such as internalization by Raji lymphoma cells in culture or inducing apoptosis of Raji cells in cell culture when cross-linked.

The anti-CD74 antibodies or fragments thereof may be used as naked antibodies, alone or in combination with one or more therapeutic agents. Alternatively, the antibodies or fragments may be utilized as immunoconjugates, attached to one or more therapeutic agents. (For methods of making immunoconjugates, see, e.g., U.S. Pat. Nos. 4,699,784; 4,824,659; 5,525,338; 5,677,427; 5,697,902; 5,716,595; 6,071,490; 6,187,284; 6,306,393; 6,548,275; 6,653,104; 6,962,702; 7,033,572; 7,147,856; and 7,259,240, the Examples section of each incorporated herein by reference.) Therapeutic agents may be selected from the group consisting of a radionuclide, a cytotoxin, a chemotherapeutic agent, a drug, a pro-drug, a toxin, an enzyme, an immunomodulator, an anti-angiogenic agent, a pro-apoptotic agent, a cytokine, a hormone, an oligonucleotide molecule (e.g., an antisense molecule or a gene) or a second antibody or fragment thereof.

Antisense molecules may include antisense molecules that correspond to bcl-2 or p53. However, other antisense molecules are known in the art, as described below, and any such known antisense molecule may be used. Second antibodies or fragments thereof may bind to an antigen selected from the group consisting of carbonic anhydrase IX, CCCL19, CCCL21, CSAp, CD1, CD1a, CD2, CD3, CD4, CD5, CD8, CD11A, CD14, CD15, CD16, CD18, CD19, IGF-1R, CD20, CD21, CD22, CD23, CD25, CD29, CD30, CD32b, CD33, CD37, CD38, CD40, CD40L, CD45, CD46, CD52, CD54, CD55, CD59, CD64, CD66a-e, CD67, CD70, CD74, CD79a, CD80, CD83, CD95, CD126, CD133, CD138, CD147, CD154, CXCR4, CXCR7, CXCL12, HIF-1α, AFP, PSMA, CEACAM5, CEACAM6, B7, ED-B of fibronectin, Factor H, FHL-1, Flt-3, folate receptor, GROB, HMGB-1, hypoxia inducible factor (HIF), HM1.24, insulin-like growth factor-1 (IGF-1), IFN-γ, IFN-α, IFN-β, IL-2, IL-4R, IL-6R, IL-13R, IL-15R, IL-17R, IL-18R, IL-6, IL-8, IL-12, IL-15, IL-17, IL-18, IL-25, W-10, MAGE, mCRP, MCP-1, MIP-1A, MIP-1B, MIF, MUC1, MUC2, MUC3, MUC4, MUC5, NCA-95, NCA-90, Ia, HM1.24, EGP-1, EGP-2, HLA-DR, tenascin, Le(y), RANTES, T101, TAC, Tn antigen, Thomson-Friedenreich antigens, tumor necrosis antigens, TNF-α, TRAIL receptor (R1 and R2), VEGFR, EGFR, PlGF, complement factors C3, C3a, C3b, C5a, C5, and an oncogene product.

The therapeutic agent may be selected from the group consisting of aplidin, azaribine, anastrozole, azacytidine, bleomycin, bortezomib, bryostatin-1, busulfan, calicheamycin, camptothecin, 10-hydroxycamptothecin, carmustine, celecoxib, chlorambucil, cisplatinum, irinotecan (CPT-11), SN-38, carboplatin, cladribine, cyclophosphamide, cytarabine, dacarbazine, docetaxel, dactinomycin, daunomycin glucuronide, daunorubicin, dexamethasone, diethylstilbestrol, doxorubicin, doxorubicin glucuronide, epirubicin glucuronide, ethinyl estradiol, estramustine, etoposide, etoposide glucuronide, etoposide phosphate, floxuridine, 3',5'-O-dioleoyl-FudR, fludarabine, flutamide, fluorouracil, fluoxymesterone, gemcitabine, hydroxyprogesterone caproate, hydroxyurea, idarubicin, ifosfamide, L-asparaginase, leucovorin, lomustine, mechlorethamine, medroprogesterone acetate, megestrol acetate, melphalan, mercaptopurine, 6-mercaptopurine, methotrexate, mitoxantrone, mithramycin, mitomycin, mitotane, phenyl butyrate, prednisone, procarbazine, paclitaxel, pentostatin, PSI-341, semustine streptozocin, tamoxifen, taxanes, testosterone propionate, thalidomide, thioguanine, thiotepa, teniposide, topotecan, uracil mustard, vinblastine, vinorelbine, vincristine, ricin, abrin, ribonuclease, onconase, rapLR1, DNase I, Staphylococcal enterotoxin-A, pokeweed antiviral protein, gelonin, diphtheria toxin, Pseudomonas exotoxin, and Pseudomonas endotoxin.

The therapeutic agent may comprise a radionuclide selected from the group consisting of $^{103m}$Rh, $^{103}$Ru, $^{105}$Rh, $^{105}$Ru, $^{107}$Hg, $^{109}$Pd, $^{109}$Pt, $^{111}$Ag, $^{111}$In, $^{113m}$In, $^{119}$Sb, $^{11}$C, $^{121m}$Te, $^{122m}$Te, $^{125}$I, $^{125m}$Te, $^{126}$I, $^{131}$I, $^{133}$I, $^{13}$N, $^{142}$Pr, $^{143}$Pr, $^{149}$Pm, $^{152}$Dy, $^{153}$Sm, $^{15}$O, $^{161}$Ho, $^{161}$Tb, $^{165}$Tm, $^{166}$Dy, $^{166}$Ho, $^{167}$Tm, $^{168}$Tm, $^{169}$Er, $^{169}$Yb, $^{177}$Lu, $^{186}$Re, $^{188}$Re, $^{189m}$Os, $^{189}$Re, $^{192}$Ir, $^{194}$Ir, $^{197}$Pt, $^{198}$Au, $^{199}$Au, $^{201}$Tl, $^{203}$Hg, $^{211}$At, $^{211}$Bi, $^{211}$Pb, $^{212}$Bi, $^{212}$Pb, $^{213}$Bi, $^{215}$Po, $^{217}$At, $^{219}$Rn, $^{221}$Fr, $^{223}$Ra, $^{224}$Ac, $^{225}$Ac, $^{225}$Fm, $^{32}$P, $^{33}$P, $^{47}$Sc, $^{51}$Cr, $^{57}$Co, $^{58}$Co, $^{59}$Fe, $^{62}$Cu, $^{67}$Cu, $^{67}$Ga, $^{75}$Br, $^{75}$Se, $^{76}$Br, $^{77}$As, $^{77}$Br, $^{80m}$Br, $^{89}$Sr, $^{90}$Y, $^{95}$Ru, $^{97}$Ru, $^{99}$Mo and $^{99m}$Tc.

The therapeutic agent may be an enzyme selected from the group consisting of malate dehydrogenase, staphylococcal nuclease, delta-V-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase.

An immunomodulator of use may be selected from the group consisting of a cytokine, a stem cell growth factor, a lymphotoxin, a hematopoietic factor, a colony stimulating factor (CSF), an interferon (IFN), erythropoietin, thrombopoietin and combinations thereof. Exemplary immunomodulators may include IL-1, IL-2, IL-3, IL-6, IL-10, IL-12, IL-18, IL-21, interferon-α, interferon-β, interferon-γ, G-CSF, GM-CSF, and mixtures thereof.

Exemplary anti-angiogenic agents may include angiostatin, endostatin, baculostatin, canstatin, maspin, anti-VEGF binding molecules, anti-placental growth factor binding molecules, or anti-vascular growth factor binding molecules.

In certain embodiments, the antibody or fragment may comprise one or more chelating moieties, such as NOTA, DOTA, DTPA, TETA, Tscg-Cys, or Tsca-Cys. In certain embodiments, the chelating moiety may form a complex with a therapeutic or diagnostic cation, such as Group II, Group III, Group IV, Group V, transition, lanthanide or actinide metal cations, Tc, Re, Bi, Cu, As, Ag, Au, At, or Pb.

In some embodiments, the antibody or fragment thereof may be a human, chimeric, or humanized antibody or fragment thereof. A humanized antibody or fragment thereof may comprise the complementarity-determining regions (CDRs) of a murine antibody and the constant and framework (FR) region sequences of a human antibody, which may be substituted with at least one amino acid from corresponding FRs of a murine antibody. A chimeric antibody or fragment thereof may include the light and heavy chain variable regions of a murine antibody, attached to human antibody constant regions. The antibody or fragment thereof may include human constant regions of IgG1, IgG2a, IgG3, or IgG4.

In certain preferred embodiments, the anti-CD74 complex may be formed by a technique known as dock-and-lock (DNL) (see, e.g., U.S. Pat. Nos. 7,521,056; 7,527,787; 7,534,866; 7,550,143 and U.S. Patent Publ. No. 20090060862, filed Oct. 26, 2007, the Examples section of each of which is incorporated herein by reference.) Generally, the DNL technique takes advantage of the specific and high-affinity binding interaction between a dimerization and docking domain (DDD) sequence derived from cAMP-dependent protein kinase and an anchor domain (AD) sequence derived from any of a variety of AKAP proteins. The DDD and AD peptides may be attached to any protein, peptide or other molecule. Because the DDD sequences spontaneously dimerize and bind to the AD sequence, the DNL technique allows the formation of complexes between any selected molecules that may be attached to DDD or AD sequences. Although the standard DNL complex comprises a trimer with two DDD-linked molecules attached to one AD-linked molecule, variations in complex structure allow the formation of dimers, trimers, tetramers, pentamers, hexamers and other multimers. In some embodiments, the DNL complex may comprise two or more antibodies, antibody fragments or fusion proteins which bind to the same antigenic determinant or to two or more different antigens. The DNL complex may also comprise one or more other effectors, such as a cytokine or PEG moiety.

Also disclosed is a method for treating and/or diagnosing a disease or disorder that includes administering to a patient a therapeutic and/or diagnostic composition that includes any of the aforementioned antibodies or fragments thereof. Typically, the composition is administered to the patient intravenously, intramuscularly or subcutaneously at a dose of 20-5000 mg.

In preferred embodiments, the disease or disorder is associated with CD74-expressing cells and may be a cancer, an immune dysregulation disease, an autoimmune disease, an organ-graft rejection, a graft-versus-host disease, a solid tumor, non-Hodgkin's lymphoma, Hodgkin's lymphoma, multiple myeloma, a B-cell malignancy, or a T-cell malignancy. A B-cell malignancy may include indolent forms of B-cell lymphomas, aggressive forms of B-cell lymphomas, chronic lymphatic leukemias, acute lymphatic leukemias, and/or multiple myeloma. Solid tumors may include melanomas, carcinomas, sarcomas, and/or gliomas. A carcinoma may include renal carcinoma, lung carcinoma, intestinal carcinoma, stomach carcinoma, breast carcinoma, prostate cancer, ovarian cancer, and/or melanoma.

Exemplary autoimmune diseases include acute idiopathic thrombocytopenic purpura, chronic idiopathic thrombocytopenic purpura, dermatomyositis, Sydenham's chorea, myasthenia gravis, systemic lupus erythematosus, lupus nephritis, rheumatic fever, polyglandular syndromes, bullous pemphigoid, diabetes mellitus, Henoch-Schonlein purpura, post-streptococcal nephritis, erythema nodosum, Takayasu's arteritis, Addison's disease, rheumatoid arthritis, multiple sclerosis, sarcoidosis, ulcerative colitis, erythema multiforme, IgA nephropathy, polyarteritis nodosa, ankylosing spondylitis, Goodpasture's syndrome, thromboangitis obliterans, Sjogren's syndrome, primary biliary cirrhosis, Hashimoto's thyroiditis, thyrotoxicosis, scleroderma, chronic active hepatitis, polymyositis/dermatomyositis, polychondritis, pemphigus vulgaris, Wegener's granulomatosis, membranous nephropathy, amyotrophic lateral sclerosis, tabes dorsalis, giant cell arteritis/polymyalgia, pernicious anemia, rapidly progressive glomerulonephritis, psoriasis, or fibrosing alveolitis. However, the skilled artisan will realize that any disease or condition characterized by expression of CD74 may be treated using the claimed compositions and methods.

FIG. 3. CD74 expression in FTY treated MCL cell lines. (A) Jeko-1 and Mino cell lines were treated with FTY720, chloroquine, rapamycin or combinations at the indicated concentrations, harvested at 24 hours, and immunoblotted for CD74 (top panels). Actin was used as a loading control. Representative histograms summarizing 3 independent experiments are also shown (middle panels). Histograms were obtained using densitometry data for CD74 levels in treated samples relative to untreated samples and normalized to the actin control. CD74 mRNA expression in MCL cell lines treated with FTY720 at the indicated concentrations for 8 or 24 hours was measured by real-time RT-PCR. (bottom panels). The bar graph shows normalized fold expression of CD74 mRNA relative to untreated control using GAPDH as an internal control. (B) CD74 MFI of MCL cells treated with FTY720, chloroquine or rapamycin at the indicated concentrations after 8 and 24 hours. Cells were stained with an anti-CD74 antibody (FITC conjugated and CD74 MFI was measured by flow cytometry. Representative histograms summarizing the MFI of untreated and treated Jeko-1, Mino, UPN-1 and Z-138 cells are shown. (C) The amount of total cellular CD74 was determined by confocal microscopy. Jeko-1, Mino, UPN-1 and Z-138 cells were treated with FTY720 at the indicated doses, chloroquine (40 µM), rapamycin (10 µM) or the combination of FTY720 and chloroquine, for 4, 8 and 24 hours. CD74 fluorescence intensity was measured in 4 microscopic fields and integrated intensity was averaged relative to the number of cells per field (~180-220 cells per condition). Representative histograms summarizing CD74 fluorescence intensity are shown. P values are calculated comparing FTY720, chloroquine and rapamycin treatment to the untreated control.

FIG. 4. FTY720 sensitizes MCL cell lines and primary patient tumor cells to milatuzumab-mediated cytotoxicity. (A) Four MCL cell lines and primary cells from 6 patients were treated with FTY720 and/or milatuzumab plus cross-linking antibodies at the indicated concentrations. (B) Patient characteristics. (C) Individual patient responses. (D) Representative histograms summarizing patient responses. Cell death was determined by annexin V/PI staining and flow cytometry at 24 hours. Data are shown as the percentage of annexin V−/PI− cells (live cells) and are normalized to untreated controls. Combination treatment resulted in a statistically significant enhanced induction of cell death compared with either agent alone in MCL cell lines and primary cells (P<0.01). Combination treatment resulted in synergistic cell death in blastic variant derived cell lines (Jeko-1, UPN-1 and Z-138), and was additive in a classic variant derived cell line (Mino) and primary MCL cells.

Figure 5:
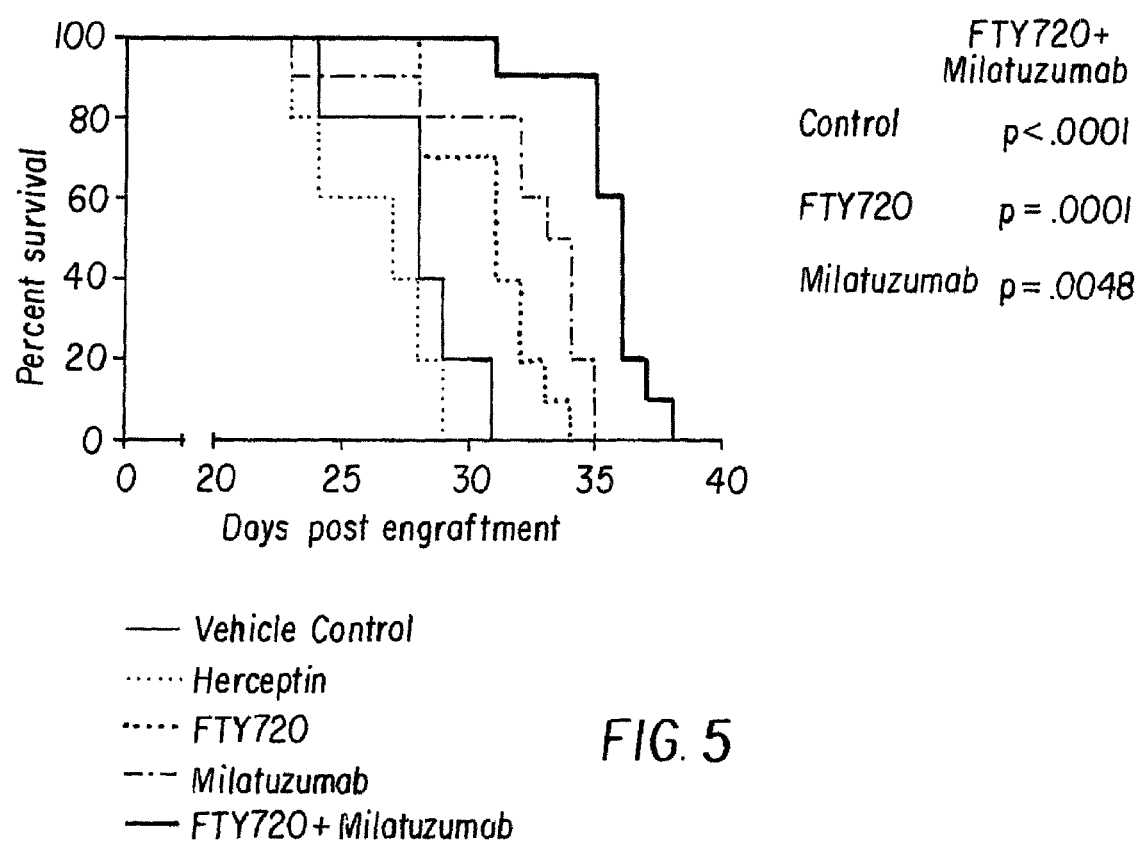

FIG. 5. Evaluation of in vivo therapeutic activity of FTY720 and milatuzumab in the preclinical MCL model. SCID mice were injected i.v. with $40 \times 10^6$ JeKo cells and observed daily for signs of tumor burden. The median survival for FTY720 and milatuzumab treated mice (N=10) was 36 days (95% CI:31-36), compared to 31 days for the FTY720 treated mice (95% CI:28-32) and 33.5 days for the milatuzumab treated mice (95% CI:23-34).

DETAILED DESCRIPTION

Definitions

As used herein, the terms "a", "an" and "the" may refer to either the singular or plural, unless the context otherwise makes clear that only the singular is meant.

An "antibody" refers to a full-length (i.e., naturally occurring or formed by normal immunoglobulin gene fragment recombinatorial processes) immunoglobulin molecule (e.g., an IgG antibody) or an immunologically active (i.e., antigen-binding) portion of an immunoglobulin molecule, like an antibody fragment.

An "antibody fragment" is a portion of an antibody such as F(ab')$_2$, F(ab)$_2$, Fab', Fab, Fv, scFv, single domain antibodies (DABs or VHHs) and the like, including half-molecules of IgG4 (van der Neut Kolfschoten et al. (Science 2007; 317 (14 September):1554-1557). Regardless of structure, an antibody fragment binds with the same antigen that is recognized by the intact antibody. For example, an anti-CD74 antibody fragment binds with an epitope of CD74. The term "antibody fragment" also includes isolated fragments consisting of the variable regions, such as the "Fv" fragments consisting of the variable regions of the heavy and light chains and recombinant single chain polypeptide molecules in which light and heavy chain variable regions are connected by a peptide linker ("scFv proteins").

A "chimeric antibody" is a recombinant protein that contains the variable domains including the complementarity determining regions (CDRs) of an antibody derived from one species, preferably a rodent antibody, while the constant domains of the antibody molecule are derived from those of a human antibody. For veterinary applications, the constant domains of the chimeric antibody may be derived from that of other species, such as a cat or dog.

A "humanized antibody" is a recombinant protein in which the CDRs from an antibody from one species; e.g., a rodent antibody, are transferred from the heavy and light variable chains of the rodent antibody into human heavy and light variable domains. Additional FR amino acid substitutions from the parent, e.g. murine, antibody may be made. The constant domains of the antibody molecule are derived from those of a human antibody.

A "human antibody" is an antibody obtained from transgenic mice that have been genetically engineered to produce human antibodies in response to antigenic challenge. In this technique, elements of the human heavy and light chain locus are introduced into strains of mice derived from embryonic stem cell lines that contain targeted disruptions of the endogenous heavy chain and light chain loci. The transgenic mice can synthesize human antibodies specific for human antigens, and the mice can be used to produce human antibody-secreting hybridomas. Methods for obtaining human antibodies from transgenic mice are described by Green et al., Nature Genet. 7:13 (1994), Lonberg et al., Nature 368:856 (1994), and Taylor et al., Int. Immun. 6:579 (1994). A fully human antibody also can be constructed by genetic or chromosomal transfection methods, as well as phage display technology, all of which are known in the art. (See, e.g., McCafferty et al., Nature 348:552-553 (1990) for the production of human antibodies and fragments thereof in vitro, from immunoglobulin variable domain gene repertoires from unimmunized donors). In this technique, antibody variable domain genes are cloned in-frame into either a major or minor coat protein gene of a filamentous bacteriophage, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. In this way, the phage mimics some of the properties of the B cell. Phage display can be performed in a variety of formats, for their review, see, e.g. Johnson and Chiswell, Current Opinion in Structural Biology 3:5564-571 (1993). Human antibodies may also be generated by in vitro activated B cells. (See, U.S. Pat. Nos. 5,567,610 and 5,229,275).

A "therapeutic agent" is an atom, molecule, or compound that is useful in the treatment of a disease. Examples of therapeutic agents include but are not limited to antibodies, antibody fragments, drugs, toxins, enzymes, nucleases, hormones, immunomodulators, antisense oligonucleotides, chelators, boron compounds, photoactive agents, dyes and radioisotopes.

A "diagnostic agent" is an atom, molecule, or compound that is useful in diagnosing a disease. Useful diagnostic agents include, but are not limited to, radioisotopes, dyes, contrast agents, fluorescent compounds or molecules and enhancing agents (e.g., paramagnetic ions). Preferably, the diagnostic agents are selected from the group consisting of radioisotopes, enhancing agents, and fluorescent compounds.

An "immunoconjugate" is a conjugate of an antibody, antibody fragment, antibody fusion protein, bispecific antibody or multispecific antibody with an atom, molecule, or a higher-ordered structure (e.g., with a carrier, a therapeutic agent, or a diagnostic agent). A "naked antibody" is an antibody that is not conjugated to any other agent.

As used herein, the term "antibody fusion protein" is a recombinantly produced antigen-binding molecule in which an antibody or antibody fragment is linked to another protein or peptide, such as the same or different antibody or antibody fragment or a DDD or AD peptide. The fusion protein may comprise a single antibody component, a multivalent or multispecific combination of different antibody components or multiple copies of the same antibody component. The fusion protein may additionally comprise an antibody or an antibody fragment and a therapeutic agent. Examples of therapeutic agents suitable for such fusion proteins include immunomodulators and toxins. One preferred toxin comprises a ribonuclease (RNase), preferably a recombinant RNase.

A "multispecific antibody" is an antibody that can bind simultaneously to at least two targets that are of different structure, e.g., two different antigens, two different epitopes on the same antigen, or a hapten and/or an antigen or epitope. A "multivalent antibody" is an antibody that can bind simultaneously to at least two targets that are of the same or different structure. Valency indicates how many binding arms or sites the antibody has to a single antigen or epitope; i.e., monovalent, bivalent, trivalent or multivalent. The multivalency of the antibody means that it can take advantage of multiple interactions in binding to an antigen, thus increasing the avidity of binding to the antigen. Specificity indicates how many antigens or epitopes an antibody is able to bind; i.e., monospecific, bispecific, trispecific, multispecific. Using these definitions, a natural antibody, e.g., an IgG, is bivalent because it has two binding arms but is monospecific because it binds to one epitope. Multispecific, multivalent antibodies are constructs that have more than one binding site of different specificity. For example, a diabody, where one binding site reacts with one antigen and the other with another antigen.

A "bispecific antibody" is an antibody that can bind simultaneously to two targets which are of different structure. Bispecific antibodies (bsAb) and bispecific antibody fragments (bsFab) may have at least one arm that specifically binds to, for example, a B-cell, T-cell, myeloid-, plasma-, and mast-cell antigen or epitope and at least one other arm that specifically binds to a targetable conjugate that bears a therapeutic or diagnostic agent. A variety of bispecific antibodies can be produced using molecular engineering.

Fingolimod

In preferred embodiments, FTY720 (fingolimod) or compounds of similar activity are used in combination with anti-CD74 antibodies to treat a variety of CD74-associated disease states, such as cancer, autoimmune disease or immune system dysfunction (e.g., graft-versus host disease, organ transplant rejection). Fingolimod is an immunomodulating drug approved for therapy of multiple sclerosis. Fingolimod is a sphingosine 1-phosphate receptor modulator that sequesters lymphocytes in lymph nodes, preventing them from contributing to autoimmune and/or inflammatory reactions (Chun & Hartung, 2010, Clin Neuropharmacol 33:91-101). As discussed in Example 1 below, fingolimod also induces expression of CD74 and acts synergistically with anti-CD74 antibodies to induce cell death of target cells in CD74-associated diseases. Fingolimod has also been reported to be a cannabinoid receptor antagonist, a cPLA2 inhibitor and a ceramide synthase inhibitor (Paugh et al., 2006, Mol Pharmacol 70:41-50; Payne et al., 2007, Blood 109:1077-85; Berdyshev et al., 2009, J Biol Chem 284:5467-777).

Fingolimod is the lead compound in the class of sphingosine 1-phosphate (S1P) receptor modulators (Dev et al., 2008, Pharmacol Ther 117:77-93; Baumruker et al., 2007, Expert Opin Investig Drugs 16:283-89). SIP is a pleiotropic bioactive lipid mediator that regulates several processes important for hematologic cancer progression, including cell migration, growth, survival and angiogenesis (Stevenson et al., 2011, Anticancer Agents Med Chem 11:794-98). S1P is generated by two sphingosine kinases, SphK1 and SphK2 and is exported outside the cell, where it activates specific cell surface S1P G-protein coupled receptors (Id.). Evidence exists that SphK1 and SphK2 may exert opposite effects on various processes, such as cell proliferation, and that increased SphK1 may be associated with the transformed phenotype (Id.). Elevated SphK1 is observed in multiple cancer types, including acute leukemia (Id.). Other therapeutic agents of potential use for combination therapy with anti-CD74 antibodies may include known SphK1 inhibitors, such as N—N-dimtheylsphingosine (DMS), N,N-dimethylphytosphingosine, F-12509a, 4-[[4-(4-chlorophenyl)-2-thiazoyl]amino]phenol (SKI-II), (2R,3S,4E)-N-methyl-5-(4-pentylphenyl)-2-aminopent-4-ene-1,3-diol (SK1-I) and 2-(p-hydroxyanilino)-4-(p-chlorophenyl)thiazole (Stevenson et al., 2011, Anticancer Agents Med Chem 11:794-98).

Fingolimod is phosphorylated by SphK2. The phosphorylated form of the drug is a potent agonist of four the five G protein coupled receptors for S1P: $S1P_1$, $S1P_3$, $S1P_4$ and $S1P_5$ (Adachi & Chiba, 2007, Perspectives in Medicinal Chemistry 1:11-23). It has been suggested that immunomodulatory activity of FTY720 is based on agonism at the S1P$_1$ receptor (Id.). In certain alternative embodiments, other S1P receptor modulators may be of use in combination with anti-CD74 antibodies and/or fingolimod. Exemplary S1P receptor modulators have been reported, such as AFD(R) (Brinkmann et al., 2002, J Biol Chem 277:21453-57), KRP-203 (Adachi & Chiba, 2007, Perspectives in Medicinal Chemistry 1:11-23) and various fingolimod analogs (Id.).

In still other alternative embodiments, other agents that are known to increase CD74 expression in cells may be used in combination with anti-CD74 antibodies. As reported in Example 2 below, an exemplary agent inducing CD74 expression is interferon-γ.

Although Example 1 below discloses the synergistic effects of fingolimod and anti-CD74 antibody in mantle cell lymphoma, the skilled artisan will realize that S1P is associated with tumor progression and/or inhibition of apoptosis in a variety of cancer types (Milstein & Spiegel, 2006, Cancer Cell 9:148-50; Pyne & Pyne, 2010, Nat Rev Cancer 10:489-503), including many leukemias and lymphomas (Stevenson et al., 2011, Anticancer Agents Med Chem 11:794-98).

Preparation of Antibodies

The immunoconjugates and compositions described herein may include monoclonal antibodies. Rodent monoclonal antibodies to specific antigens may be obtained by methods known to those skilled in the art. (See, e.g., Kohler and Milstein, Nature 256: 495 (1975), and Coligan et al. (eds.), CURRENT PROTOCOLS IN IMMUNOLOGY, VOL. 1, pages 2.5.1-2.6.7 (John Wiley & Sons 1991)).

General techniques for cloning murine immunoglobulin variable domains have been disclosed, for example, by the publication of Orlandi et al., Proc. Nat'l Acad. Sci. USA 86: 3833 (1989). Techniques for constructing chimeric antibodies are well known to those of skill in the art. As an example, Leung et al., Hybridoma 13:469 (1994), disclose how they produced an LL2 chimera by combining DNA sequences encoding the V$_k$ and V$_H$ domains of LL2 monoclonal antibody, an anti-CD22 antibody, with respective human and IgG$_1$ constant region domains. This publication also provides the nucleotide sequences of the LL2 light and heavy chain variable regions, V$_k$ and V$_H$, respectively. Techniques for producing humanized antibodies are disclosed, for example, by Jones et al., Nature 321: 522 (1986), Reichmann et al., Nature 332: 323 (1988), Verhoeyen et al., Science 239: 1534 (1988), Carter et al., Proc. Nat'l Acad. Sci. USA 89: 4285 (1992), Sandhu, Crit. Rev. Biotech. 12: 437 (1992), and Singer et al., J. Immun. 150: 2844 (1993).

A chimeric antibody is a recombinant protein that contains the variable domains including the CDRs derived from one species of animal, such as a rodent antibody, while the remainder of the antibody molecule; i.e., the constant domains, is derived from a human antibody. Accordingly, a chimeric monoclonal antibody can also be humanized by replacing the sequences of the murine FR in the variable domains of the chimeric antibody with one or more different human FR. Specifically, mouse CDRs are transferred from heavy and light variable chains of the mouse immunoglobulin into the corresponding variable domains of a human antibody. As simply transferring mouse CDRs into human FRs often results in a reduction or even loss of antibody affinity, additional modification might be required in order to restore the original affinity of the murine antibody. This can be accomplished by the replacement of one or more some human residues in the FR regions with their murine counterparts to obtain an antibody that possesses good binding affinity to its epitope. (See, e.g., Tempest et al., Biotechnology 9:266 (1991) and Verhoeyen et al., Science 239: 1534 (1988)).

A fully human antibody can be obtained from a transgenic non-human animal. (See, e.g., Mendez et al., Nature Genetics, 15: 146-156, 1997; U.S. Pat. No. 5,633,425.) Methods for producing fully human antibodies using either combinatorial approaches or transgenic animals transformed with human immunoglobulin loci are known in the art (e.g., Mancini et al., 2004, New Microbiol. 27:315-28; Conrad and Scheller, 2005, Comb. Chem. High Throughput Screen. 8:117-26; Brekke and Loset, 2003, Curr. Opin. Pharmacol. 3:544-50; each incorporated herein by reference). Such fully human antibodies are expected to exhibit even fewer side effects than chimeric or humanized antibodies and to function in vivo as essentially endogenous human antibodies. In certain embodiments, the claimed methods and procedures may utilize human antibodies produced by such techniques.

In one alternative, the phage display technique may be used to generate human antibodies (e.g., Dantas-Barbosa et al., 2005, Genet. Mol. Res. 4:126-40, incorporated herein by reference). Human antibodies may be generated from normal humans or from humans that exhibit a particular disease state, such as cancer (Dantas-Barbosa et al., 2005). The advantage to constructing human antibodies from a diseased individual is that the circulating antibody repertoire may be biased towards antibodies against disease-associated antigens.

In one non-limiting example of this methodology, Dantas-Barbosa et al. (2005) constructed a phage display library of human Fab antibody fragments from osteosarcoma patients. Generally, total RNA was obtained from circulating blood lymphocytes (Id.) Recombinant Fab were cloned from the μ, γ and κ chain antibody repertoires and inserted into a phage display library (Id.) RNAs were converted to cDNAs and used to make Fab cDNA libraries using specific primers against the heavy and light chain immunoglobulin sequences (Marks et al., 1991, *J. Mol. Biol.* 222:581-97). Library construction was performed according to Andris-Widhopf et al. (2000, In: *Phage Display Laboratory Manual*, Barbas et al. (eds), 1$^{st}$ edition, Cold Spring Harbor Laboratory Press, Cold Spring Harbor, N.Y. pp. 9.1 to 9.22, incorporated herein by reference). The final Fab fragments were digested with restriction endonucleases and inserted into the bacteriophage genome to make the phage display library. Such libraries may be screened by standard phage display methods. The skilled artisan will realize that this technique is exemplary only and any known method for making and screening human antibodies or antibody fragments by phage display may be utilized.

In another alternative, transgenic animals that have been genetically engineered to produce human antibodies may be used to generate antibodies against essentially any immunogenic target, using standard immunization protocols as discussed above. Methods for obtaining human antibodies from transgenic mice are described by Green et al., Nature Genet. 7:13 (1994), Lonberg et al., Nature 368:856 (1994), and Taylor et al., Int. Immun. 6:579 (1994). A non-limiting example of such a system is the XENOMOUSE® (e.g., Green et al., 1999, *J. Immunol. Methods* 231:11-23, incorporated herein by reference) from Abgenix (Fremont, Calif.). In the XENOMOUSE® and similar animals, the mouse antibody genes have been inactivated and replaced by functional human antibody genes, while the remainder of the mouse immune system remains intact.

The XENOMOUSE® was transformed with germline-configured YACs (yeast artificial chromosomes) that contained portions of the human IgH and Ig kappa loci, including the majority of the variable region sequences, along accessory genes and regulatory sequences. The human variable region repertoire may be used to generate antibody producing B cells, which may be processed into hybridomas by known techniques. A XENOMOUSE® immunized with a target antigen will produce human antibodies by the normal immune response, which may be harvested and/or produced by standard techniques discussed above. A variety of strains of XENOMOUSE® are available, each of which is capable of producing a different class of antibody. Transgenically produced human antibodies have been shown to have therapeutic potential, while retaining the pharmacokinetic properties of normal human antibodies (Green et al., 1999). The skilled artisan will realize that the claimed compositions and methods are not limited to use of the XENOMOUSE® system but may utilize any transgenic animal that has been genetically engineered to produce human antibodies.

Known Antibodies

In various embodiments, the claimed methods and compositions may utilize any of a variety of antibodies known in the art. Antibodies of use may be commercially obtained from a number of known sources. For example, a variety of antibody secreting hybridoma lines are available from the American Type Culture Collection (ATCC, Manassas, Va.). A large number of antibodies against various disease targets, including but not limited to tumor-associated antigens, have been deposited at the ATCC and/or have published variable region sequences and are available for use in the claimed methods and compositions. See, e.g., U.S. Pat. Nos. 7,312,318; 7,282,567; 7,151,164; 7,074,403; 7,060,802; 7,056,509; 7,049,060; 7,045,132; 7,041,803; 7,041,802; 7,041,293; 7,038,018; 7,037,498; 7,012,133; 7,001,598; 6,998,468; 6,994,976; 6,994,852; 6,989,241; 6,974,863; 6,965,018; 6,964,854; 6,962,981; 6,962,813; 6,956,107; 6,951,924; 6,949,244; 6,946,129; 6,943,020; 6,939,547; 6,921,645; 6,921,645; 6,921,533; 6,919,433; 6,919,078; 6,916,475; 6,905,681; 6,899,879; 6,893,625; 6,887,468; 6,887,466; 6,884,594; 6,881,405; 6,878,812; 6,875,580; 6,872,568; 6,867,006; 6,864,062; 6,861,511; 6,861,227; 6,861,226; 6,838,282; 6,835,549; 6,835,370; 6,824,780; 6,824,778; 6,812,206; 6,793,924; 6,783,758; 6,770,450; 6,767,711; 6,764,688; 6,764,681; 6,764,679; 6,743,898; 6,733,981; 6,730,307; 6,720,155; 6,716,966; 6,709,653; 6,693,176; 6,692,908; 6,689,607; 6,689,362; 6,689,355; 6,682,737; 6,682,736; 6,682,734; 6,673,344; 6,653,104; 6,652,852; 6,635,482; 6,630,144; 6,610,833; 6,610,294; 6,605,441; 6,605,279; 6,596,852; 6,592,868; 6,576,745; 6,572,856; 6,566,076; 6,562,618; 6,545,130; 6,544,749; 6,534,058; 6,528,625; 6,528,269; 6,521,227; 6,518,404; 6,511,665; 6,491,915; 6,488,930; 6,482,598; 6,482,408; 6,479,247; 6,468,531; 6,468,529; 6,465,173; 6,461,823; 6,458,356; 6,455,044; 6,455,040; 6,451,310; 6,444,206; 6,441,143; 6,432,404; 6,432,402; 6,419,928; 6,413,726; 6,406,694; 6,403,770; 6,403,091; 6,395,276; 6,395,274; 6,387,350; 6,383,759; 6,383,484; 6,376,654; 6,372,215; 6,359,126; 6,355,481; 6,355,444; 6,355,245; 6,355,244; 6,346,246; 6,344,198; 6,340,571; 6,340,459; 6,331,175; 6,306,393; 6,254,868; 6,187,287; 6,183,744; 6,129,914; 6,120,767; 6,096,289; 6,077,499; 5,922,302; 5,874,540; 5,814,440; 5,798,229; 5,789,554; 5,776,456; 5,736,119; 5,716,595; 5,677,136; 5,587,459; 5,443,953; 5,525,338, the Examples section of each of which is incorporated herein by reference. These are exemplary only and a wide variety of other antibodies and their hybridomas are known in the art. The skilled artisan will realize that antibody sequences or antibody-secreting hybridomas against almost any disease-associated antigen may be obtained by a simple search of the ATCC, NCBI and/or USPTO databases for antibodies against a selected disease-associated target of interest. The antigen binding domains of the cloned antibodies may be amplified, excised, ligated into an expression vector, transfected into an adapted host cell and used for protein production, using standard techniques well known in the art (see, e.g., U.S. Pat. Nos. 7,531,327; 7,537,930; 7,608,425 and 7,785,880, the Examples section of each of which is incorporated herein by reference).

Particular antibodies that may be of use for therapy of cancer within the scope of the claimed methods and compositions include, but are not limited to, LL1 (anti-CD74), LL2 and RFB4 (anti-CD22), RS7 (anti-epithelial glycoprotein-1 (EGP-1)), PAM4 and KC4 (both anti-mucin), MN-14 (anti-carcinoembryonic antigen (CEA, also known as CD66e), Mu-9 (anti-colon-specific antigen-p), Immu 31 (an anti-alpha-fetoprotein), TAG-72 (e.g., CC49), Tn, J591 or HuJ591 (anti-PSMA (prostate-specific membrane antigen)), AB-PG1-XG1-026 (anti-PSMA dimer), DNB (anti-PSMA), G250 (anti-carbonic anhydrase IX), hL243 (anti-HLA-DR), alemtuzumab (anti-CD52), bevacizumab (anti-VEGF), cetuximab (anti-EGFR), gemtuzumab (anti-CD33), ibritumomab tiuxetan (anti-CD20); panitumumab (anti-EGFR); rituximab (anti-CD20); tositumomab (anti-CD20); GA101 (anti-CD20); and trastuzumab (anti-ErbB2). Such antibodies are known in the art (e.g., U.S. Pat. Nos. 5,686,072; 5,874, 540; 6,107,090; 6,183,744; 6,306,393; 6,653,104; 6,730.300; 6,899,864; 6,926,893; 6,962,702; 7,074,403; 7,230,084; 7,238,785; 7,238,786; 7,256,004; 7,282,567; 7,300,655; 7,312,318; 7,585,491; 7,612,180; 7,642,239; and U.S. Patent Application Publ. No. 20040202666 (now abandoned); 20050271671; and 20060193865; the Examples section of each incorporated herein by reference.) Specific known antibodies of use include hPAM4 (U.S. Pat. No. 7,282,567), hA20 (U.S. Pat. No. 7,251,164), hA19 (U.S. Pat. No. 7,109, 304), hIMMU31 (U.S. Pat. No. 7,300,655), hLL1 (U.S. Pat. No. 7,312,318), hLL2 (U.S. Pat. No. 7,074,403), hMu-9 (U.S. Pat. No. 7,387,773), hL243 (U.S. Pat. No. 7,612,180), hMN-14 (U.S. Pat. No. 6,676,924), hMN-15 (U.S. Pat. No. 7,541, 440), hR1 (U.S. patent application Ser. No. 12/772,645), hRS7 (U.S. Pat. No. 7,238,785), hMN-3 (U.S. Pat. No. 7,541, 440), AB-PG1-XG1-026 (U.S. patent application Ser. No. 11/983,372, deposited as ATCC PTA-4405 and PTA-4406) and D2/B (WO 2009/130575) the text of each recited patent or application is incorporated herein by reference with respect to the Figures and Examples sections.

Anti-TNF-α antibodies are known in the art and may be of use to treat immune diseases, such as autoimmune disease, immune dysfunction (e.g., graft-versus-host disease, organ transplant rejection) or diabetes. Known antibodies against TNF-α include the human antibody CDP571 (Ofei et al., 2011, Diabetes 45:881-85); murine antibodies MTNFAI, M2TNFAI, M3TNFAI, M3TNFABI, M302B and M303 (Thermo Scientific, Rockford, Ill.); infliximab (Centocor, Malvern, Pa.); certolizumab pegol (UCB, Brussels, Belgium); and adalimumab (Abbott, Abbott Park, Ill.). These and many other known anti-TNF-α antibodies may be used in the claimed methods and compositions. Other antibodies of use for therapy of immune dysregulatory or autoimmune disease include, but are not limited to, anti-B-cell antibodies such as veltuzumab, epratuzumab, milatuzumab or hL243; tocilizumab (anti-IL-6 receptor); basiliximab (anti-CD25); daclizumab (anti-CD25); efalizumab (anti-CD11a); muromonab-CD3 (anti-CD3 receptor); anti-CD40L (UCB, Brussels, Belgium); natalizumab (anti-α4 integrin) and omalizumab (anti-IgE).

Type-1 and Type-2 diabetes may be treated using known antibodies against B-cell antigens, such as CD22 (epratuzumab), CD74 (milatuzumab), CD19 (hA19), CD20 (veltuzumab) or HLA-DR (hL243) (see, e.g., Winer et al., 2011, Nature Med 17:610-18). Anti-CD3 antibodies also have been proposed for therapy of type 1 diabetes (Cernea et al., 2010, Diabetes Metab Rev 26:602-05).

Macrophage migration inhibitory factor (MIF) is an important regulator of innate and adaptive immunity and apoptosis. It has been reported that CD74 is the endogenous receptor for MIF (Leng et al., 2003, J Exp Med 197:1467-76). The therapeutic effect of antagonistic anti-CD74 antibodies on MIF-mediated intracellular pathways may be of use for treatment of a broad range of disease states, such as cancers of the bladder, prostate, breast, lung, colon and chronic lymphocytic leukemia (e.g., Meyer-Siegler et al., 2004, BMC Cancer 12:34; Shachar & Haran, 2011, Leuk Lymphoma 52:1446-54); autoimmune diseases such as rheumatoid arthritis and systemic lupus erythematosus (Morand & Leech, 2005, Front Biosci 10:12-22; Shachar & Haran, 2011, Leuk Lymphoma 52:1446-54); kidney diseases such as renal allograft rejection (Lan, 2008, Nephron Exp Nephrol. 109:e79-83); and numerous inflammatory diseases (Meyer-Siegler et al., 2009, Mediators Inflamm epub Mar. 22, 2009; Takahashi et al., 2009, Respir Res 10:33; Milatuzumab (hLL1) is an exemplary anti-CD74 antibody of therapeutic use for treatment of MIF-mediated diseases.

The pharmaceutical composition of the present invention may be used to treat a subject having a metabolic disease, such amyloidosis, or a neurodegenerative disease, such as Alzheimer's disease. Bapineuzumab is in clinical trials for Alzheimer's disease therapy. Other antibodies proposed for therapy of Alzheimer's disease include Alz 50 (Ksiezak-Reding et al., 1987, J Biol Chem 263:7943-47), gantenerumab, and solanezumab. Infliximab, an anti-TNF-α antibody, has been reported to reduce amyloid plaques and improve cognition.

In a preferred embodiment, diseases that may be treated using the claimed compositions and methods include cardiovascular diseases, such as fibrin clots, atherosclerosis, myocardial ischemia and infarction. Antibodies to fibrin (e.g., scFv(59D8); T2G1s; MH1) are known and in clinical trials as imaging agents for disclosing said clots and pulmonary emboli, while anti-granulocyte antibodies, such as MN-3, MN-15, anti-NCA95, and anti-CD15 antibodies, can target myocardial infarcts and myocardial ischemia. (See, e.g., U.S. Pat. Nos. 5,487,892; 5,632,968; 6,294,173; 7,541,440, the Examples section of each incorporated herein by reference) Anti-macrophage, anti-low-density lipoprotein (LDL), anti-MIF, and anti-CD74 (e.g., hLL1) antibodies can be used to target atherosclerotic plaques. Abciximab (anti-glycoprotein IIb/IIIa) has been approved for adjuvant use for prevention of restenosis in percutaneous coronary interventions and the treatment of unstable angina (Waldmann et al., 2000, Hematol 1:394-408). Anti-CD3 antibodies have been reported to reduce development and progression of atherosclerosis (Steffens et al., 2006, Circulation 114:1977-84). Antibodies against oxidized LDL induced a regression of established atherosclerosis in a mouse model (Ginsberg, 2007, J Am Coll Cardiol 52:2319-21). Anti-ICAM-1 antibody was shown to reduce ischemic cell damage after cerebral artery occlusion in rats (Zhang et al., 1994, Neurology 44:1747-51). Commercially available monoclonal antibodies to leukocyte antigens are represented by: OKT anti-T-cell monoclonal antibodies (available from Ortho Pharmaceutical Company) which bind to normal T-lymphocytes; the monoclonal antibodies produced by the hybridomas having the ATCC accession numbers HB44, HB55, HB12, HB78 and HB2; G7E11, W8E7, NKP15 and GO22 (Becton Dickinson); NEN9.4 (New England Nuclear); and FMC11 (Sera Labs). A description of antibodies against fibrin and platelet antigens is contained in Knight, Semin. Nucl. Med., 20:52-67 (1990).

Antibody Allotypes

Immunogenicity of therapeutic antibodies is associated with increased risk of infusion reactions and decreased duration of therapeutic response (Baert et al., 2003, N Engl J Med 348:602-08). The extent to which therapeutic antibodies induce an immune response in the host may be determined in part by the allotype of the antibody (Stickler et al., 2011, Genes and Immunity 12:213-21). Antibody allotype is related to amino acid sequence variations at specific locations in the constant region sequences of the antibody. The allotypes of IgG antibodies containing a heavy chain γ-type constant region are designated as Gm allotypes (1976, J Immunol 117:1056-59).

For the common IgG1 human antibodies, the most prevalent allotype is G1m1 (Stickler et al., 2011, Genes and Immunity 12:213-21). However, the G1m3 allotype also occurs frequently in Caucasians (Id.). It has been reported that G1m1 antibodies contain allotypic sequences that tend to induce an immune response when administered to non-G1m1 (nG1m1) recipients, such as G1m3 patients (Id.). Non-G1m1 allotype antibodies are not as immunogenic when administered to G1m1 patients (Id.).

The human G1m1 allotype comprises the amino acids aspartic acid at Kabat position 356 and leucine at Kabat position 358 in the CH3 sequence of the heavy chain IgG1. The nG1m1 allotype comprises the amino acids glutamic acid at Kabat position 356 and methionine at Kabat position 358. Both G1m1 and nG1m1 allotypes comprise a glutamic acid residue at Kabat position 357 and the allotypes are sometimes referred to as DEL and EEM allotypes.

Jefferis and Lefranc (2009, mAbs 1:1-7) reviewed sequence variations characteristic of IgG allotypes and their effect on immunogenicity. They reported that the G1m3 allotype is characterized by an arginine residue at Kabat position 214, compared to a lysine residue at Kabat 214 in the G1m17 allotype. The nG1m1,2 allotype was characterized by glutamic acid at Kabat position 356, methionine at Kabat position 358 and alanine at Kabat position 431. The G1m1,2 allotype was characterized by aspartic acid at Kabat position 356, leucine at Kabat position 358 and glycine at Kabat position 431. In addition to heavy chain constant region sequence variants, Jefferis and Lefranc (2009) reported allotypic variants in the kappa light chain constant region, with the Km1 allotype characterized by valine at Kabat position 153 and leucine at Kabat position 191, the Km1,2 allotype by alanine at Kabat position 153 and leucine at Kabat position 191, and the Km3 allotype characterized by alanine at Kabat position 153 and valine at Kabat position 191.

With regard to therapeutic antibodies, veltuzumab and rituximab are, respectively, humanized and chimeric IgG1 antibodies against CD20, of use for therapy of a wide variety of hematological malignancies and/or autoimmune diseases. Table 1 compares the allotype sequences of rituximab vs. veltuzumab. As shown in Table 1, rituximab (G1m17,1) is a DEL allotype IgG1, with an additional sequence variation at Kabat position 214 (heavy chain CH1) of lysine in rituximab vs. arginine in veltuzumab. It has been reported that veltuzumab is less immunogenic in subjects than rituximab (see, e.g., Morchhauser et al., 2009, J Clin Oncol 27:3346-53; Goldenberg et al., 2009, Blood 113:1062-70; Robak & Robak, 2011, BioDrugs 25:13-25), an effect that has been attributed to the difference between humanized and chimeric antibodies. However, the difference in allotypes between the EEM and DEL allotypes likely also accounts for the lower immunogenicity of veltuzumab.

TABLE 1

Allotypes of Rituximab vs. Veltuzumab

|  | Complete allotype | Heavy chain position and associated allotypes | | | |
|---|---|---|---|---|---|
|  |  | 214 (allotype) | 356/358 (allotype) | | 431 (allotype) |
| Rituximab | G1m17,1 | K | 17 | D/L | 1 | A | — |
| Veltuzumab | G1m3 | R | 3 | E/M | — | A | — |

In order to reduce the immunogenicity of therapeutic antibodies in individuals of nG1m1 genotype, it is desirable to select the allotype of the antibody to correspond to the G1m3 allotype, characterized by arginine at Kabat 214, and the nG1m1,2 null-allotype, characterized by glutamic acid at Kabat position 356, methionine at Kabat position 358 and alanine at Kabat position 431. Surprisingly, it was found that repeated subcutaneous administration of G1m3 antibodies over a long period of time did not result in a significant immune response. In alternative embodiments, the human IgG4 heavy chain in common with the G1m3 allotype has arginine at Kabat 214, glutamic acid at Kabat 356, methionine at Kabat 359 and alanine at Kabat 431. Since immunogenicity appears to relate at least in part to the residues at those locations, use of the human IgG4 heavy chain constant region sequence for therapeutic antibodies is also a preferred embodiment. Combinations of G1m3 IgG1 antibodies with IgG4 antibodies may also be of use for therapeutic administration.

Antibody Fragments

Antibody fragments which recognize specific epitopes can be generated by known techniques. The antibody fragments are antigen binding portions of an antibody, such as F(ab)$_2$, Fab', Fab, Fv, scFv and the like. Other antibody fragments include, but are not limited to: the F(ab')$_2$ fragments which can be produced by pepsin digestion of the antibody molecule and the Fab' fragments, which can be generated by reducing disulfide bridges of the F(ab')$_2$ fragments. Alternatively, Fab' expression libraries can be constructed (Huse et al., 1989, Science, 246:1274-1281) to allow rapid and easy identification of monoclonal Fab' fragments with the desired specificity.

A single chain Fv molecule (scFv) comprises a VL domain and a VH domain. The VL and VH domains associate to form a target binding site. These two domains are further covalently linked by a peptide linker (L). Methods for making scFv molecules and designing suitable peptide linkers are disclosed in U.S. Pat. No. 4,704,692, U.S. Pat. No. 4,946,778, R. Raag and M. Whitlow, "Single Chain Fvs." FASEB Vol 9:73-80 (1995) and R. E. Bird and B. W. Walker, "Single Chain Antibody Variable Regions," TIBTECH, Vol 9: 132-137 (1991).

An antibody fragment can be prepared by known methods, for example, as disclosed by Goldenberg, U.S. Pat. Nos. 4,036,945 and 4,331,647 and references contained therein. Also, see Nisonoff et al., Arch Biochem. Biophys. 89: 230 (1960); Porter, Biochem. J. 73: 119 (1959), Edelman et al., in METHODS IN ENZYMOLOGY VOL. 1, page 422 (Academic Press 1967), and Coligan at pages 2.8.1-2.8.10 and 2.10.-2.10.4.

A single complementarity-determining region (CDR) is a segment of the variable region of an antibody that is complementary in structure to the epitope to which the antibody binds and is more variable than the rest of the variable region. Accordingly, a CDR is sometimes referred to as hypervariable region. A variable region comprises three CDRs. CDR peptides can be obtained by constructing genes encoding the CDR of an antibody of interest. Such genes are prepared, for example, by using the polymerase chain reaction to synthesize the variable region from RNA of antibody-producing cells. (See, e.g., Larrick et al., Methods: A Companion to Methods in Enzymology 2: 106 (1991); Courtenay-Luck, "Genetic Manipulation of Monoclonal Antibodies," in MONOCLONAL ANTIBODIES: PRODUCTION, ENGINEERING AND CLINICAL APPLICATION, Ritter et al. (eds.), pages 166-179 (Cambridge University Press 1995); and Ward et al., "Genetic Manipulation and Expression of Antibodies," in MONOCLONAL ANTIBODIES: PRINCIPLES AND APPLICATIONS, Birch et al., (eds.), pages 137-185 (Wiley-Liss, Inc. 1995).

Another form of an antibody fragment is a single-domain antibody (dAb), sometimes referred to as a single chain antibody. Techniques for producing single-domain antibodies are well known in the art (see, e.g., Cossins et al., Protein Expression and Purification, 2007, 51:253-59; Shuntao et al., Molec Immunol 2006, 43:1912-19; Tanha et al., J. Biol. Chem. 2001, 276:24774-780).

In certain embodiments, the sequences of antibodies, such as the Fc portions of antibodies, may be varied to optimize the physiological characteristics of the conjugates, such as the half-life in serum. Methods of substituting amino acid sequences in proteins are widely known in the art, such as by site-directed mutagenesis (e.g. Sambrook et al., Molecular Cloning, A laboratory manual, $2^{nd}$ Ed, 1989). In preferred embodiments, the variation may involve the addition or removal of one or more glycosylation sites in the Fc sequence (e.g., U.S. Pat. No. 6,254,868, the Examples section of which is incorporated herein by reference). In other preferred embodiments, specific amino acid substitutions in the Fc sequence may be made (e.g., Hornick et al., 2000, J Nucl Med 41:355-62; Hinton et al., 2006, J Immunol 176:346-56; Petkova et al. 2006, Int Immunol 18:1759-69; U.S. Pat. No. 7,217,797).

Multispecific and Multivalent Antibodies

Various embodiments may concern use of multispecific and/or multivalent antibodies. For example, an anti-CD74 antibody or fragment thereof and an anti-HLA-DR antibody or fragment thereof may be joined together by means such as the dock-and-lock technique described below. Other combinations of antibodies or fragments thereof may be utilized. For example, another antigen expressed by the CD74-expressing cell may include a tumor marker selected from a B-cell lineage antigen, (e.g., CD19, CD20, or CD22 for the treatment of B-cell malignancies). The tumor cell marker may be a non-B-cell lineage antigen selected from the group consisting of CD30, CD33, CD52 MUC1, MUC5 and TAC. Other useful antigens may include carbonic anhydrase IX, B7, CCCL19, CCCL21, CSAp, HER-2/neu, BrE3, CD1, CD1a, CD2, CD3, CD4, CD5, CD8, CD11A, CD14, CD15, CD16, CD18, CD19, CD20 (e.g., C2B8, hA20, 1F5 MAbs), CD21, CD22, CD23, CD25, CD29, CD30, CD32b, CD33, CD37, CD38, CD40, CD40L, CD44, CD45, CD46, CD52, CD54, CD55, CD59, CD64, CD67, CD70, CD74, CD79a, CD80, CD83, CD95, CD126, CD133, CD138, CD147, CD154, CXCR4, CXCR7, CXCL12, HIF-1α, CEACAM5, CEACAM-6, alpha-fetoprotein (AFP), VEGF (e.g. AVASTIN®, fibronectin splice variant), ED-B fibronectin (e.g., L19), EGP-1, EGP-2 (e.g., 17-1A), EGF receptor (ErbB1) (e.g., ERBITUX®), ErbB2, ErbB3, Factor H, FHL-1, Flt-3, folate receptor, Ga 733, GROB, HMGB-1, hypoxia inducible factor (HIF), HM1.24, HER-2/neu, insulin-like growth factor (IGF), IFN-γ, IFN-α, IL-2R, IL-4R, IL-6R, IL-13R, IL-15R, IL-17R, IL-18R, IL-2, IL-6, IL-8, IL-12, IL-15, IL-17, IL-18, IL-25, IP-10, IGF-1R, Ia, HM1.24, gangliosides, HCG, the HLA-DR antigen to which L243 binds, CD66 antigens, i.e., CD66a-d or a combination thereof, MAGE, mCRP, MCP-1, MIP-1A, MIP-1B, macrophage migration-inhibitory factor (MIF), MUC1, MUC2, MUC3, MUC4, MUC5, placental growth factor (PlGF), PSA (prostate-specific antigen), PSMA, pancreatic cancer mucin, pancreatic cancer mucin, NCA-95, NCA-90, A3, A33, Ep-CAM, KS-1, Le(y), mesothelin, S100, tenascin, TAC, Tn antigen, Thomas-Friedenreich antigens, tumor necrosis antigens, tumor angiogenesis antigens, TNF-α, TRAIL receptor (R1 and R2), VEGFR, RANTES, T101, as well as cancer stem cell antigens, complement factors C3, C3a, C3b, C5a, C5, and an oncogene product.

Methods for producing bispecific antibodies include engineered recombinant antibodies which have additional cysteine residues so that they crosslink more strongly than the more common immunoglobulin isotypes. (See, e.g., FitzGerald et al, Protein Eng. 10(10):1221-1225, (1997)). Another approach is to engineer recombinant fusion proteins linking two or more different single-chain antibody or antibody fragment segments with the needed dual specificities. (See, e.g., Coloma et al., Nature Biotech. 15:159-163, (1997)). A variety of bispecific antibodies can be produced using molecular engineering. In one form, the bispecific antibody may consist of, for example, an scFv with a single binding site for one antigen and a Fab fragment with a single binding site for a second antigen. In another form, the bispecific antibody may consist of, for example, an IgG with two binding sites for one antigen and two scFv with two binding sites for a second antigen.

Diabodies, Triabodies and Tetrabodies

The compositions disclosed herein may also include functional bispecific single-chain antibodies (bscAb), also called diabodies. (See, e.g., Mack et al., Proc. Natl. Acad. Sci., 92: 7021-7025, 1995). For example, bscAb are produced by joining two single-chain Fv fragments via a glycine-serine linker using recombinant methods. The V light-chain ($V_L$) and V heavy-chain ($V_H$) domains of two antibodies of interest are isolated using standard PCR methods. The $V_L$ and $V_H$ cDNAs obtained from each hybridoma are then joined to form a single-chain fragment in a two-step fusion PCR. The first PCR step introduces the $(Gly_4\text{-}Ser_1)_3$ linker (SEQ ID NO:7), and the second step joins the $V_L$ and $V_H$ amplicons. Each single chain molecule is then cloned into a bacterial expression vector. Following amplification, one of the single-chain molecules is excised and sub-cloned into the other vector, containing the second single-chain molecule of interest. The resulting bscAb fragment is subcloned into a eukaryotic expression vector. Functional protein expression can be obtained by transfecting the vector into Chinese Hamster Ovary cells.

For example, a humanized, chimeric or human anti-CD74 monoclonal antibody can be used to produce antigen specific diabodies, triabodies, and tetrabodies. The monospecific diabodies, triabodies, and tetrabodies bind selectively to targeted antigens and as the number of binding sites on the molecule increases, the affinity for the target cell increases and a longer residence time is observed at the desired location. For diabodies, the two chains comprising the $V_H$ polypeptide of the humanized CD74 antibody connected to the $V_K$ polypeptide of the humanized CD74 antibody by a five amino acid residue linker may be utilized. Each chain forms one half of the humanized CD74 diabody. In the case of triabodies, the three chains comprising $V_H$ polypeptide of the humanized CD74 antibody connected to the $V_K$ polypeptide of the humanized CD74 antibody by no linker may be utilized. Each chain forms one third of the hCD74 triabody.

More recently, a tetravalent tandem diabody (termed tandab) with dual specificity has also been reported (Cochlovius et al., Cancer Research (2000) 60: 4336-4341). The bispecific tandab is a dimer of two identical polypeptides, each containing four variable domains of two different antibodies ($V_{H1}, V_{L1}, V_{H2}, V_{L2}$) linked in an orientation to facilitate the formation of two potential binding sites for each of the two different specificities upon self-association.

Dock-and-Lock (DNL)

In certain preferred embodiments, bispecific or multispecific antibodies may be produced using the dock-and-lock (DNL) technology (see, e.g., U.S. Pat. Nos. 7,521,056; 7,550, 143; 7,534,866; 7,527,787 and 7,666,400; the Examples section of each of which is incorporated herein by reference). The DNL method exploits specific protein/protein interactions that occur between the regulatory (R) subunits of cAMP-dependent protein kinase (PKA) and the anchoring domain (AD) of A-kinase anchoring proteins (AKAPs) (Baillie et al., FEBS Letters. 2005; 579: 3264. Wong and Scott, Nat. Rev. Mol. Cell Biol. 2004; 5: 959). PKA, which plays a central role in one of the best studied signal transduction pathways triggered by the binding of the second messenger cAMP to the R subunits, was first isolated from rabbit skeletal muscle in 1968 (Walsh et al., J. Biol. Chem. 1968; 243:3763). The structure of the holoenzyme consists of two catalytic subunits held in an inactive form by the R subunits (Taylor, J. Biol. Chem. 1989; 264:8443). Isozymes of PKA are found with two types of R subunits (RI and RII), and each type has α and β isoforms (Scott, Pharmacol. Ther. 1991; 50:123). The R subunits have been isolated only as stable dimers and the dimerization domain has been shown to consist of the first 44 amino-terminal residues (Newlon et al., Nat. Struct. Biol. 1999; 6:222). Binding of cAMP to the R subunits leads to the release of active catalytic subunits for a broad spectrum of serine/threonine kinase activities, which are oriented toward selected substrates through the compartmentalization of PKA via its docking with AKAPs (Scott et al., J. Biol. Chem. 1990; 265; 21561)

Since the first AKAP, microtubule-associated protein-2, was characterized in 1984 (Lohmann et al., Proc. Natl. Acad. Sci USA. 1984; 81:6723), more than 50 AKAPs that localize to various sub-cellular sites, including plasma membrane, actin cytoskeleton, nucleus, mitochondria, and endoplasmic reticulum, have been identified with diverse structures in species ranging from yeast to humans (Wong and Scott, Nat. Rev. Mol. Cell Biol. 2004; 5:959). The AD of AKAPs for PKA is an amphipathic helix of 14-18 residues (Carr et al., J. Biol. Chem. 1991; 266:14188). The amino acid sequences of the AD are quite varied among individual AKAPs, with the binding affinities reported for RH dimers ranging from 2 to 90 nM (Alto et al., Proc. Natl. Acad. Sci. USA. 2003; 100:4445). AKAPs will only bind to dimeric R subunits. For human RIIα, the AD binds to a hydrophobic surface formed by the 23 amino-terminal residues (Colledge and Scott, Trends Cell Biol. 1999; 6:216). Thus, the dimerization domain and AKAP binding domain of human RIIα are both located within the same N-terminal 44 amino acid sequence (Newlon et al., Nat. Struct. Biol. 1999; 6:222; Newlon et al., EMBO J. 2001; 20:1651), which is termed the DDD herein.

We have developed a platform technology to utilize the DDD of human RIIα and the AD of AKAP as an excellent pair of linker modules for docking any two entities, referred to hereafter as A and B, into a noncovalent complex, which could be further locked into a stably tethered structure through the introduction of cysteine residues into both the DDD and AD at strategic positions to facilitate the formation of disulfide bonds. The general methodology of the "dock-and-lock" approach is as follows. Entity A is constructed by linking a DDD sequence to a precursor of A, resulting in a first component hereafter referred to as a. Because the DDD sequence would effect the spontaneous formation of a dimer, A would thus be composed of $a_2$. Entity B is constructed by linking an AD sequence to a precursor of B, resulting in a second component hereafter referred to as b. The dimeric motif of DDD contained in $a_2$ will create a docking site for binding to the AD sequence contained in b, thus facilitating a ready association of $a_2$ and b to form a binary, trimeric complex composed of $a_2b$. This binding event is made irreversible with a subsequent reaction to covalently secure the two entities via disulfide bridges, which occurs very efficiently based on the principle of effective local concentration because the initial binding interactions should bring the reactive thiol groups placed onto both the DDD and AD into proximity (Chmura et al., Proc. Natl. Acad. Sci. USA. 2001; 98:8480) to ligate site-specifically. Using various combinations of linkers, adaptor modules and precursors, a wide variety of DNL constructs of different stoichiometry may be produced and used, including but not limited to dimeric, trimeric, tetrameric, pentameric and hexameric DNL constructs (see, e.g., U.S. Pat. Nos. 7,550,143; 7,521,056; 7,534,866; 7,527,787 and 7,666,400.)

By attaching the DDD and AD away from the functional groups of the two precursors, such site-specific ligations are also expected to preserve the original activities of the two precursors. This approach is modular in nature and potentially can be applied to link, site-specifically and covalently, a wide range of substances, including peptides, proteins, antibodies, antibody fragments, and other effector moieties with a wide range of activities. Utilizing the fusion protein method of constructing AD and DDD conjugated effectors described in the Examples below, virtually any protein or peptide may be incorporated into a DNL construct. However, the technique is not limiting and other methods of conjugation may be utilized.

A variety of methods are known for making fusion proteins, including nucleic acid synthesis, hybridization and/or amplification to produce a synthetic double-stranded nucleic acid encoding a fusion protein of interest. Such double-stranded nucleic acids may be inserted into expression vectors for fusion protein production by standard molecular biology techniques (see, e.g. Sambrook et al., Molecular Cloning, A laboratory manual, $2^{nd}$ Ed, 1989). In such preferred embodiments, the AD and/or DDD moiety may be attached to either the N-terminal or C-terminal end of an effector protein or peptide. However, the skilled artisan will realize that the site of attachment of an AD or DDD moiety to an effector moiety may vary, depending on the chemical nature of the effector moiety and the part(s) of the effector moiety involved in its physiological activity. Site-specific attachment of a variety of effector moieties may be performed using techniques known in the art, such as the use of bivalent cross-linking reagents and/or other chemical conjugation techniques.

For different types of constructs, different AD or DDD sequences may be utilized. Exemplary DDD and AD sequences are provided below.
DDD1: SHIQIPPGLTELLQGYTVEVLRQQPP-DLVEFAVEYFTRLREARA (SEQ ID NO:8)
DDD2: CGHIQIPPGLTELLQGYTVEVLRQQPP-DLVEFAVEYFTRLREARA (SEQ ID NO:9)
AD1: QIEYLAKQIVDNAIQQA (SEQ ID NO:10)
AD2: CGQIEYLAKQIVDNAIQQAGC (SEQ ID NO:11)

The skilled artisan will realize that DDD1 and DDD2 comprise the DDD sequence of the human RIIα form of protein kinase A. However, in alternative embodiments, the DDD and AD moieties may be based on the DDD sequence of the human RIα form of protein kinase A and a corresponding AKAP sequence, as exemplified in DDD3, DDD3C and AD3 below.

DDD3
(SEQ ID NO: 12)
SLRECELYVQKHNIQALLKDSIVQLCTARPERPMAFLREYFERLEKEEAK

DDD3C
(SEQ ID NO: 13)
MSCGGSLRECELYVQKHNIQALLKDSIVQLCTARPERPMAFLREYFERLE

KEEAK

AD3
(SEQ ID NO: 14)
CGFEELAWKIAKMIWSDVFQQGC

In alternative embodiments, any of the human PKA regulatory subunit DDD moieties may be utilized to form DNL complexes. There are only four variants of human PKA DDD sequences, corresponding to the DDD moieties of PKA RIα, RIIα, RIβ and RIIβ. The RIIα DDD sequence is the basis of DDD1 and DDD2 disclosed above. The four human PKA DDD sequences are shown below. The DDD sequence represents residues 1-44 of RIIα, 1-44 of RIIβ, 12-61 of RIα and 13-66 of RIβ. (Note that the sequence of DDD1 is modified slightly from the human PKA RIIα DDD moiety.)

PKA RIα
(SEQ ID NO: 15)
SLRECELYVQKHNIQALLKDVSIVQLCTARPERPMAFLREYFEKLEKEEA

K

PKA RIβ
(SEQ ID NO: 16)
SLKGCELYVQLHGIQQVLKDCIVHLCISKPERPMKFLREHFEKLEKEENR

QILA

PKA RIIα
(SEQ ID NO: 17)
SHIQIPPGLTELLQGYTVEVGQQPPDLVDFAVEYFTRLREARRQ

PKA RIIβ
(SEQ ID NO: 18)
SIEIPAGLTELLQGFTVEVLRHQPADLLEFALQHFTRLQQENER

The structure-function relationships of the AD and DDD domains have been the subject of investigation. (See, e.g., Burns-Hamuro et al., 2005, Protein Sci 14:2982-92; Carr et al., 2001, J Biol Chem 276:17332-38; Alto et al., 2003, Proc Natl Acad Sci USA 100:4445-50; Hundsrucker et al., 2006, Biochem J 396:297-306; Stokka et al., 2006, Biochem J 400: 493-99; Gold et al., 2006, Mol Cell 24:383-95; Kinderman et al., 2006, Mol Cell 24:397-408, the entire text of each of which is incorporated herein by reference.)

For example, Kinderman et al. (2006) examined the crystal structure of the AD-DDD binding interaction and concluded that the human DDD sequence contained a number of conserved amino acid residues that were important in either dimer formation or AKAP binding, underlined in SEQ ID NO:8 below. (See FIG. 1 of Kinderman et al., 2006, incorporated herein by reference.) The skilled artisan will realize that in designing sequence variants of the DDD sequence, one would desirably avoid changing any of the underlined residues, while conservative amino acid substitutions might be made for residues that are less critical for dimerization and AKAP binding.

```
                                        (SEQ ID NO: 8)
SHIQIPPGLTELLQGYTVEVLRQQPPDLVEFAVEYFTRLREARA
```

Alto et al. (2003) performed a bioinformatic analysis of the AD sequence of various AKAP proteins to design an RII selective AD sequence called AKAP-IS (SEQ ID NO:10), with a binding constant for DDD of 0.4 nM. The AKAP-IS sequence was designed as a peptide antagonist of AKAP binding to PKA. Residues in the AKAP-IS sequence where substitutions tended to decrease binding to DDD are underlined in SEQ ID NO:10. The skilled artisan will realize that in designing sequence variants of the AD sequence, one would desirably avoid changing any of the underlined residues, while conservative amino acid substitutions might be made for residues that are less critical for DDD binding.

```
    AKAP-IS sequence
    QIEYLAKQIVDNAIQQA       (SEQ ID NO: 10)
```

Gold (2006) utilized crystallography and peptide screening to develop a SuperAKAP-IS sequence (SEQ ID NO:19), exhibiting a five order of magnitude higher selectivity for the RII isoform of PKA compared with the RI isoform. Underlined residues indicate the positions of amino acid substitutions, relative to the AKAP-IS sequence, which increased binding to the DDD moiety of RIIα. In this sequence, the N-terminal Q residue is numbered as residue number 4 and the C-terminal A residue is residue number 20. Residues where substitutions could be made to affect the affinity for RIIα were residues 8, 11, 15, 16, 18, 19 and 20 (Gold et al., 2006). It is contemplated that in certain alternative embodiments, the SuperAKAP-IS sequence may be substituted for the AKAP-IS AD moiety sequence to prepare DNL constructs. Other alternative sequences that might be substituted for the AKAP-IS AD sequence are shown in SEQ ID NO:20-22. Substitutions relative to the AKAP-IS sequence are underlined. It is anticipated that the AD moiety may also include the additional N-terminal residues cysteine and glycine and C-terminal residues glycine and cysteine. FIG. 2 of Gold et al. disclosed additional DDD-binding sequences from a variety of AKAP proteins, of potential use for formation of DNL complexes.

```
    SuperAKAP-IS
    QIEYVAKQIVDYAIHQA       (SEQ ID NO: 19)

Alternative AKAP sequences
    QIEYKAKQIVDHAIHQA       (SEQ ID NO: 20)

QIEYHAKQIVDHAIHQA       (SEQ ID NO: 21)

QIEYVAKQIVDHAIHQA       (SEQ ID NO: 22)
```

Hundsrucker et al. (2006) developed still other peptide competitors for AKAP binding to PKA, with a binding constant as low as 0.4 nM to the DDD of the RII form of PKA. The sequences of various AKAP antagonistic peptides are provided in Table 1 of Hundsrucker et al. The skilled artisan will realize that these and other amino acid substitutions in the antibody moiety or linker portions of the DNL constructs may be utilized to enhance the therapeutic and/or pharmacokinetic properties of the resulting DNL constructs.

The plasmid vector pdHL2 has been used to produce a number of antibodies and antibody-based constructs. See Gillies et al., J Immunol Methods (1989), 125:191-202; Losman et al., Cancer (Phila) (1997), 80:2660-6. The di-cistronic mammalian expression vector directs the synthesis of the heavy and light chains of IgG. The vector sequences are mostly identical for many different IgG-pdHL2 constructs, with the only differences existing in the variable domain (VH and VL) sequences. Using molecular biology tools known to those skilled in the art, these IgG expression vectors can be converted into Fab-DDD or Fab-AD expression vectors. To generate Fab-DDD expression vectors, the coding sequences for the hinge, CH2 and CH3 domains of the heavy chain are replaced with a sequence encoding the first 4 residues of the hinge, a 14 residue Gly-Ser linker and the first 44 residues of human RIIα (referred to as DDD1). To generate Fab-AD expression vectors, the sequences for the hinge, CH2 and CH3 domains of IgG are replaced with a sequence encoding the first 4 residues of the hinge, a 15 residue Gly-Ser linker and a 17 residue synthetic AD called AKAP-IS (referred to as AD1), which was generated using bioinformatics and peptide array technology and shown to bind RIIα dimers with a very high affinity (0.4 nM). See Alto, et al. Proc. Natl. Acad. Sci., U.S.A (2003), 100:4445-50.

Using the techniques described above, the following IgG or Fab fusion proteins were constructed and incorporated into DNL constructs. The fusion proteins retained the antigen-binding characteristics of the parent antibodies and the DNL constructs exhibited the antigen-binding activities of the incorporated antibodies or antibody fragments.

TABLE 2

| Fusion proteins comprising IgG or Fab Moieties | |
|---|---|
| Fusion Protein | Binding Specificity |
| C-AD1-Fab-h679 | HSG |
| C-AD2-Fab-h679 | HSG |
| C-(AD2)$_2$-Fab-h679 | HSG |
| C-AD2-IgG-h734 | Indium-DTPA |
| C-AD2-IgG-hA20 | CD20 |
| C-AD2-IgG-hA20L | CD20 |
| C-AD2-IgG-hL243 | HLA-DR |
| C-AD2-IgG-hLL2 | CD22 |
| N-AD2-IgG-hLL2 | CD22 |
| C-AD2-IgG-hMN-14 | CEACAM5 |
| C-AD2-IgG-hR1 | IGF-1R |
| C-AD2-IgG-hRS7 | EGP-1 (TROP2) |
| C-AD2-IgG-hPAM4 | pancreatic CA mucin |
| C-AD2-IgG-hLL1 | CD74 |
| C-DDD1-Fab-hMN-14 | CEACAM5 |
| C-DDD2-Fab-hMN-14 | CEACAM5 |
| C-DDD2-Fab-h679 | HSG |
| C-DDD2-Fab-hA19 | CD19 |
| C-DDD2-Fab-hA20 | CD20 |
| C-DDD2-Fab-hAFP | AFP |
| C-DDD2-Fab-hL243 | HLA-DR |
| C-DDD2-Fab-hLL1 | CD74 |
| C-DDD2-Fab-hLL2 | CD22 |
| C-DDD2-Fab-hMN-3 | CEACAM6 |
| C-DDD2-Fab-hMN-15 | CEACAM6 |
| C-DDD2-Fab-hPAM4 | pancreatic CA mucin |

TABLE 2-continued

Fusion proteins comprising IgG or Fab Moieties

| Fusion Protein | Binding Specificity |
|---|---|
| C-DDD2-Fab-hR1 | IGF-1R |
| C-DDD2-Fab-hRS7 | EGP-1 (TROP2) |
| N-DDD2-Fab-hMN-14 | CEACAM5 |

Pre-Targeting

In certain alternative embodiments, therapeutic agents may be administered by a pretargeting method, utilizing bispecific or multispecific antibodies. In pretargeting, the bispecific or multispecific antibody comprises at least one binding arm that binds to an antigen exhibited by a targeted cell or tissue, while at least one other binding arm binds to a hapten on a targetable construct. The targetable construct comprises one or more haptens and one or more therapeutic and/or diagnostic agents.

Pre-targeting is a multistep process originally developed to resolve the slow blood clearance of directly targeting antibodies, which contributes to undesirable toxicity to normal tissues such as bone marrow. With pre-targeting, a radionuclide or other diagnostic or therapeutic agent is attached to a small delivery molecule (targetable construct) that is cleared within minutes from the blood. A pre-targeting bispecific or multispecific antibody, which has binding sites for the targetable construct as well as a target antigen, is administered first, free antibody is allowed to clear from circulation and then the targetable construct is administered.

Pre-targeting methods are disclosed, for example, in Goodwin et al., U.S. Pat. No. 4,863,713; Goodwin et al., J. Nucl. Med. 29:226, 1988; Hnatowich et al., J. Nucl. Med. 28:1294, 1987; Oehr et al., J. Nucl. Med. 29:728, 1988; Klibanov et al., J. Nucl. Med. 29:1951, 1988; Sinitsyn et al., J. Nucl. Med. 30:66, 1989; Kalofonos et al., J. Nucl. Med. 31:1791, 1990; Schechter et al., Int. J. Cancer 48:167, 1991; Paganelli et al., Cancer Res. 51:5960, 1991; Paganelli et al., Nucl. Med. Commun. 12:211, 1991; U.S. Pat. No. 5,256,395; Stickney et al., Cancer Res. 51:6650, 1991; Yuan et al., Cancer Res. 51:3119, 1991; U.S. Pat. Nos. 6,077,499; 7,011,812; 7,300,644; 7,074,405; 6,962,702; 7,387,772; 7,052,872; 7,138,103; 6,090,381; 6,472,511; 6,962,702; and 6,962,702, each incorporated herein by reference.

A pre-targeting method of treating or diagnosing a disease or disorder in a subject may be provided by: (1) administering to the subject a bispecific antibody or antibody fragment; (2) optionally administering to the subject a clearing composition, and allowing the composition to clear the antibody from circulation; and (3) administering to the subject the targetable construct, containing one or more chelated or chemically bound therapeutic or diagnostic agents.

Immunoconjugates

In preferred embodiments, an antibody or antibody fragment may be directly attached to one or more therapeutic agents to form an immunoconjugate. Therapeutic agents may be attached, for example to reduced SH groups and/or to carbohydrate side chains. A therapeutic agent can be attached at the hinge region of a reduced antibody component via disulfide bond formation. Alternatively, such agents can be attached using a heterobifunctional cross-linker, such as N-succinyl 3-(2-pyridyldithio)propionate (SPDP). Yu et al., Int. J. Cancer 56: 244 (1994). General techniques for such conjugation are well-known in the art. See, for example, Wong, CHEMISTRY OF PROTEIN CONJUGATION AND CROSS-LINKING (CRC Press 1991); Upeslacis et al., "Modification of Antibodies by Chemical Methods," in MONOCLONAL ANTIBODIES: PRINCIPLES AND APPLICATIONS, Birch et al. (eds.), pages 187-230 (Wiley-Liss, Inc. 1995); Price, "Production and Characterization of Synthetic Peptide-Derived Antibodies," in MONOCLONAL ANTIBODIES: PRODUCTION, ENGINEERING AND CLINICAL APPLICATION, Ritter et al. (eds.), pages 60-84 (Cambridge University Press 1995). Alternatively, the therapeutic agent can be conjugated via a carbohydrate moiety in the Fc region of the antibody.

Methods for conjugating functional groups to antibodies via an antibody carbohydrate moiety are well-known to those of skill in the art. See, for example, Shih et al., Int. J. Cancer 41: 832 (1988); Shih et al., Int. J. Cancer 46: 1101 (1990); and Shih et al., U.S. Pat. No. 5,057,313, the Examples section of which is incorporated herein by reference. The general method involves reacting an antibody having an oxidized carbohydrate portion with a carrier polymer that has at least one free amine function. This reaction results in an initial Schiff base (imine) linkage, which can be stabilized by reduction to a secondary amine to form the final conjugate.

The Fc region may be absent if the antibody component of the immunoconjugate is an antibody fragment. However, it is possible to introduce a carbohydrate moiety into the light chain variable region of a full length antibody or antibody fragment. See, for example, Leung et al., J. Immunol. 154: 5919 (1995); U.S. Pat. Nos. 5,443,953 and 6,254,868, the Examples section of which is incorporated herein by reference. The engineered carbohydrate moiety is used to attach the therapeutic or diagnostic agent.

An alternative method for attaching therapeutic agents to a targeting molecule involves use of click chemistry reactions. The click chemistry approach was originally conceived as a method to rapidly generate complex substances by joining small subunits together in a modular fashion. (See, e.g., Kolb et al., 2004, Angew Chem Int Ed 40:3004-31; Evans, 2007, Aust J Chem 60:384-95.) Various forms of click chemistry reaction are known in the art, such as the Huisgen 1,3-dipolar cycloaddition copper catalyzed reaction (Tornoe et al., 2002, J Organic Chem 67:3057-64), which is often referred to as the "click reaction." Other alternatives include cycloaddition reactions such as the Diels-Alder, nucleophilic substitution reactions (especially to small strained rings like epoxy and aziridine compounds), carbonyl chemistry formation of urea compounds and reactions involving carbon-carbon double bonds, such as alkynes in thiol-yne reactions.

The azide alkyne Huisgen cycloaddition reaction uses a copper catalyst in the presence of a reducing agent to catalyze the reaction of a terminal alkyne group attached to a first molecule. In the presence of a second molecule comprising an azide moiety, the azide reacts with the activated alkyne to form a 1,4-disubstituted 1,2,3-triazole. The copper catalyzed reaction occurs at room temperature and is sufficiently specific that purification of the reaction product is often not required. (Rostovstev et al., 2002, Angew Chem Int Ed 41:2596; Tornoe et al., 2002, J Org Chem 67:3057.) The azide and alkyne functional groups are largely inert towards biomolecules in aqueous medium, allowing the reaction to occur in complex solutions. The triazole formed is chemically stable and is not subject to enzymatic cleavage, making the click chemistry product highly stable in biological systems. Although the copper catalyst is toxic to living cells, the copper-based click chemistry reaction may be used in vitro for immunoconjugate formation.

A copper-free click reaction has been proposed for covalent modification of biomolecules. (See, e.g., Agard et al., 2004, J Am Chem Soc 126:15046-47.) The copper-free reaction uses ring strain in place of the copper catalyst to promote a [3+2] azide-alkyne cycloaddition reaction (Id.) For example, cyclooctyne is an 8-carbon ring structure comprising an internal alkyne bond. The closed ring structure induces a substantial bond angle deformation of the acetylene, which is highly reactive with azide groups to form a triazole. Thus, cyclooctyne derivatives may be used for copper-free click reactions (Id.)

Another type of copper-free click reaction was reported by Ning et al. (2010, Angew Chem Int Ed 49:3065-68), involving strain-promoted alkyne-nitrone cycloaddition. To address the slow rate of the original cyclooctyne reaction, electron-withdrawing groups are attached adjacent to the triple bond (Id.) Examples of such substituted cyclooctynes include difluorinated cyclooctynes, 4-dibenzocyclooctynol and azacyclooctyne (Id.) An alternative copper-free reaction involved strain-promoted alkyne-nitrone cycloaddition to give N-alkylated isoxazolines (Id.) The reaction was reported to have exceptionally fast reaction kinetics and was used in a one-pot three-step protocol for site-specific modification of peptides and proteins (Id.) Nitrons were prepared by the condensation of appropriate aldehydes with N-methylhydroxylamine and the cycloaddition reaction took place in a mixture of acetonitrile and water (Id.) These and other known click chemistry reactions may be used to attach therapeutic agents to antibodies in vitro.

The specificity of the click chemistry reaction may be used as a substitute for the antibody-hapten binding interaction used in pretargeting with bispecific antibodies. In this alternative embodiment, the specific reactivity of e.g., cyclooctyne moieties for azide moieties or alkyne moieties for nitrone moieties may be used in an in vivo cycloaddition reaction. An antibody or other targeting molecule is activated by incorporation of a substituted cyclooctyne, an azide or a nitrone moiety. A targetable construct is labeled with one or more diagnostic or therapeutic agents and a complementary reactive moiety. I.e., where the targeting molecule comprises a cyclooctyne, the targetable construct will comprise an azide; where the targeting molecule comprises a nitrone, the targetable construct will comprise an alkyne, etc. The activated targeting molecule is administered to a subject and allowed to localize to a targeted cell, tissue or pathogen, as disclosed for pretargeting protocols. The reactive labeled targetable construct is then administered. Because the cyclooctyne, nitrone or azide on the targetable construct is unreactive with endogenous biomolecules and highly reactive with the complementary moiety on the targeting molecule, the specificity of the binding interaction results in the highly specific binding of the targetable construct to the tissue-localized targeting molecule.

Therapeutic Agents

A wide variety of therapeutic reagents can be administered concurrently or sequentially with the subject anti-CD74 antibodies. For example, drugs, toxins, oligonucleotides, immunomodulators, hormones, hormone antagonists, enzymes, enzyme inhibitors, radionuclides, angiogenesis inhibitors, other antibodies or fragments thereof, etc. The therapeutic agents recited here are those agents that also are useful for administration separately with an antibody or fragment thereof as described above. Therapeutic agents include, for example, chemotherapeutic drugs such as vinca alkaloids, anthracyclines, gemcitabine, epipodophyllotoxins, taxanes, antimetabolites, alkylating agents, antibiotics, SN-38, COX-2 inhibitors, antimitotics, anti-angiogenic and pro-apoptotic agents, particularly doxorubicin, methotrexate, paclitaxel, CPT-11, camptothecans, proteosome inhibitors, mTOR inhibitors, HDAC inhibitors, tyrosine kinase inhibitors, and others.

Other useful cancer chemotherapeutic drugs include nitrogen mustards, alkyl sulfonates, nitrosoureas, triazenes, folic acid analogs, COX-2 inhibitors, antimetabolites, pyrimidine analogs, purine analogs, platinum coordination complexes, mTOR inhibitors, tyrosine kinase inhibitors, proteosome inhibitors, HDAC inhibitors, camptothecins, hormones, and the like. Suitable chemotherapeutic agents are described in REMINGTON'S PHARMACEUTICAL SCIENCES, 19th Ed. (Mack Publishing Co. 1995), and in GOODMAN AND GILMAN'S THE PHARMACOLOGICAL BASIS OF THERAPEUTICS, 7th Ed. (MacMillan Publishing Co. 1985), as well as revised editions of these publications. Other suitable chemotherapeutic agents, such as experimental drugs, are known to those of skill in the art.

In a preferred embodiment, conjugates of camptothecins and related compounds, such as SN-38, may be conjugated to an anti-cancer antibody, for example as disclosed in U.S. Pat. No. 7,591,994; and U.S. Ser. No. 11/388,032, filed Mar. 23, 2006, the Examples section of each of which is incorporated herein by reference.

A toxin can be of animal, plant or microbial origin. A toxin, such as Pseudomonas exotoxin, may also be complexed to or form the therapeutic agent portion of an immunoconjugate. Other toxins include ricin, abrin, ribonuclease (RNase), DNase I, Staphylococcal enterotoxin-A, pokeweed antiviral protein, onconase, gelonin, diphtheria toxin, Pseudomonas exotoxin, and Pseudomonas endotoxin. See, for example, Pastan et al., Cell 47:641 (1986), Goldenberg, C A—A Cancer Journal for Clinicians 44:43 (1994), Sharkey and Goldenberg, C A—A Cancer Journal for Clinicians 56:226 (2006). Additional toxins suitable for use are known to those of skill in the art and are disclosed in U.S. Pat. No. 6,077,499, the Examples section of which is incorporated herein by reference.

As used herein, the term "immunomodulator" includes a cytokine, a lymphokine, a monokine, a stem cell growth factor, a lymphotoxin, a hematopoietic factor, a colony stimulating factor (CSF), an interferon (IFN), parathyroid hormone, thyroxine, insulin, proinsulin, relaxin, prorelaxin, follicle stimulating hormone (FSH), thyroid stimulating hormone (TSH), luteinizing hormone (LH), hepatic growth factor, prostaglandin, fibroblast growth factor, prolactin, placental lactogen, OB protein, a transforming growth factor (TGF), TGF-α, TGF-β, insulin-like growth factor (IGF), erythropoietin, thrombopoietin, tumor necrosis factor (TNF), TNF-α, TNF-β, a mullerian-inhibiting substance, mouse gonadotropin-associated peptide, inhibin, activin, vascular endothelial growth factor, integrin, interleukin (IL), granulocyte-colony stimulating factor (G-CSF), granulocyte macrophage-colony stimulating factor (GM-CSF), interferon-α, interferon-β, interferon-γ, S1 factor, IL-1, IL-1cc, IL-2, IL-3, IL-4, IL-5, IL-6, IL-7, IL-8, IL-9, IL-10, IL-11, IL-12, IL-13, IL-14, IL-15, IL-16, IL-17, IL-18, IL-21 and IL-25, LIF, kit-ligand, FLT-3, angiostatin, thrombospondin, endostatin and LT, and the like.

The antibody or fragment thereof may be administered as an immunoconjugate comprising one or more radioactive isotopes useful for treating diseased tissue. Particularly useful therapeutic radionuclides include, but are not limited to $^{111}$In, $^{177}$In, $^{212}$Bi, $^{213}$Bi, $^{211}$At, $^{62}$Cu, $^{64}$Cu, $^{67}$Cu, $^{90}$Y, $^{125}$I, $^{131}$I, $^{32}$P, $^{33}$P, $^{47}$Sc, $^{111}$Ag, $^{67}$Ga, $^{142}$Pr, $^{153}$Sm, $^{161}$Tb, $^{166}$Dy, $^{166}$Ho, $^{186}$Re, $^{188}$Re, $^{189}$Re, $^{212}$Pb, $^{223}$Ra, $^{225}$Ac, $^{59}$Fe, $^{75}$Se, $^{77}$As, $^{89}$Sr, $^{99}$Mo, $^{105}$Rh, $^{109}$Pd, $^{143}$Pr, $^{149}$Pm, $^{169}$Er, $^{194}$Ir, $^{198}$Au, $^{199}$Au, and $^{211}$Pb. The therapeutic radionuclide preferably has a decay energy in the range of 20 to 6,000 keV, preferably in the ranges 60 to 200 keV for an Auger emitter, 100-2,500 keV for a beta emitter, and 4,000-6,000 keV for an alpha emitter. Maximum decay energies of useful beta-particle-emitting nuclides are preferably 20-5,000 keV, more preferably 100-4,000 keV, and most preferably 500-2,500 keV. Also preferred are radionuclides that substantially decay with Auger-emitting particles. For example, Co-58, Ga-67, Br-80m, Tc-99m, Rh-103m, Pt-109, In-111, Sb-119, I-125, Ho-161, Os-189m and Ir-192. Decay energies of useful beta-particle-emitting nuclides are preferably <1,000 keV, more preferably <100 keV, and most preferably <70 keV. Also preferred are radionuclides that substantially decay with generation of alpha-particles. Such radionuclides include, but are not limited to: Dy-152, At-211, Bi-212, Ra-223, Rn-219, Po-215, Bi-211, Ac-225, Fr-221, At-217, Bi-213 and Fm-255. Decay energies of useful alpha-particle-emitting radionuclides are preferably 2,000-10,000 keV, more preferably 3,000-8,000 keV, and most preferably 4,000-7,000 keV.

Additional potential therapeutic radioisotopes include $^{11}$C, $^{13}$N, $^{15}$O, $^{75}$Br, $^{198}$Au, $^{224}$Ac, $^{126}$I, $^{133}$I, $^{77}$Br, $^{113m}$In, $^{95}$Ru, $^{97}$Ru, $^{103}$Ru, $^{105}$Ru, $^{107}$Hg, $^{203}$Hg, $^{121m}$Te, $^{122m}$Te, $^{125m}$Te, $^{165}$Tm, $^{167}$Tm, $^{168}$Tm, $^{197}$Pt, $^{109}$Pd, $^{105}$Rh, $^{142}$Pr, $^{143}$Pr, $^{161}$Tb, $^{166}$Ho, $^{199}$Au, $^{57}$Co, $^{58}$Co, $^{51}$Cr, $^{59}$Fe, $^{75}$Se, $^{201}$Tl, $^{225}$Ac, $^{76}$Br, $^{169}$Yb, and the like.

Interference RNA

In certain preferred embodiments the therapeutic agent may be a siRNA or interference RNA species. The siRNA, interference RNA or therapeutic gene may be attached to a carrier moiety that is conjugated to an antibody or fragment thereof. A variety of carrier moieties for siRNA have been reported and any such known carrier may be incorporated into a therapeutic antibody for use. Non-limiting examples of carriers include protamine (Rossi, 2005, Nat Biotech 23:682-84; Song et al., 2005, Nat Biotech 23:709-17); dendrimers such as PAMAM dendrimers (Pan et al., 2007, Cancer Res. 67:8156-8163); polyethylenimine (Schiffelers et al., 2004, Nucl Acids Res 32:e149); polypropyleneimine (Taratula et al., 2009, J Control Release 140:284-93); polylysine (Inoue et al., 2008, J Control Release 126:59-66); histidine-containing reducible polycations (Stevenson et al., 2008, J Control Release 130:46-56); histone H1 protein (Haberland et al., 2009, Mol Biol Rep 26:1083-93); cationic comb-type copolymers (Sato et al., 2007, J Control Release 122:209-16); polymeric micelles (U.S. Patent Application Publ. No. 20100121043); and chitosan-thiamine pyrophosphate (Rojanarata et al., 2008, Pharm Res 25:2807-14). The skilled artisan will realize that in general, polycationic proteins or polymers are of use as siRNA carriers. The skilled artisan will further realize that siRNA carriers can also be used to carry other oligonucleotide or nucleic acid species, such as antisense oligonucleotides or short DNA genes.

Known siRNA species of potential use include those specific for IKK-gamma (U.S. Pat. No. 7,022,828); VEGF, Flt-1 and Flk-1/KDR (U.S. Pat. No. 7,148,342); Bc12 and EGFR (U.S. Pat. No. 7,541,453); CDC20 (U.S. Pat. No. 7,550,572); transducin (beta)-like 3 (U.S. Pat. No. 7,576,196); KRAS (U.S. Pat. No. 7,576,197); carbonic anhydrase II (U.S. Pat. No. 7,579,457); complement component 3 (U.S. Pat. No. 7,582,746); interleukin-1 receptor-associated kinase 4 (IRAK4) (U.S. Pat. No. 7,592,443); survivin (U.S. Pat. No. 7,608,7070); superoxide dismutase 1 (U.S. Pat. No. 7,632,938); MET proto-oncogene (U.S. Pat. No. 7,632,939); amyloid beta precursor protein (APP) (U.S. Pat. No. 7,635,771); IGF-1R (U.S. Pat. No. 7,638,621); ICAM1 (U.S. Pat. No. 7,642,349); complement factor B (U.S. Pat. No. 7,696,344); p53 (U.S. Pat. No. 7,781,575), and apolipoprotein B (U.S. Pat. No. 7,795,421), the Examples section of each referenced patent incorporated herein by reference.

Additional siRNA species are available from known commercial sources, such as Sigma-Aldrich (St Louis, Mo.), Invitrogen (Carlsbad, Calif.), Santa Cruz Biotechnology (Santa Cruz, Calif.), Ambion (Austin, Tex.), Dharmacon (Thermo Scientific, Lafayette, Colo.), Promega (Madison, Wis.), Mirus Bio (Madison, Wis.) and Qiagen (Valencia, Calif.), among many others. Other publicly available sources of siRNA species include the siRNAdb database at the Stockholm Bioinformatics Centre, the MIT/ICBP siRNA Database, the RNAi Consortium shRNA Library at the Broad Institute, and the Probe database at NCBI. For example, there are 30,852 siRNA species in the NCBI Probe database. The skilled artisan will realize that for any gene of interest, either a siRNA species has already been designed, or one may readily be designed using publicly available software tools. Any such siRNA species may be delivered using the subject DNL complexes.

Exemplary siRNA species known in the art are listed in Table 3. Although siRNA is delivered as a double-stranded molecule, for simplicity only the sense strand sequences are shown in Table 3.

TABLE 3

Exemplary siRNA Sequences

| Target | Sequence | SEQ ID NO |
|---|---|---|
| VEGF R2 | AATGCGGCGGTGGTGACAGTA | SEQ ID NO: 23 |
| VEGF R2 | AAGCTCAGCACACAGAAAGAC | SEQ ID NO: 24 |
| CXCR4 | UAAAAUCUUCCUGCCCACCdTdT | SEQ ID NO: 25 |
| CXCR4 | GGAAGCUGUUGGCUGAAAAdTdT | SEQ ID NO: 26 |
| PPARC1 | AAGACCAGCCUCUUUGCCCAG | SEQ ID NO: 27 |
| Dynamin 2 | GGACCAGGCAGAAAACGAG | SEQ ID NO: 28 |
| Catenin | CUAUCAGGAUGACGCGG | SEQ ID NO: 29 |
| E1A binding protein | UGACACAGGCAGGCUUGACUU | SEQ ID NO: 30 |

TABLE 3-continued

Exemplary siRNA Sequences

| Target | Sequence | SEQ ID NO |
|---|---|---|
| Plasminogen activator | GGTGAAGAAGGGCGTCCAA | SEQ ID NO: 31 |
| K-ras | GATCCGTTGGAGCTGTTGGCGTAGTT CAAGAGACTCGCCAACAGCTCCAACT TTTGGAAA | SEQ ID NO: 32 |
| Sortilin 1 | AGGTGGTGTTAACAGCAGAG | SEQ ID NO: 33 |
| Apolipoprotein E | AAGGTGGAGCAAGCGGTGGAG | SEQ ID NO: 34 |
| Apolipoprotein E | AAGGAGTTGAAGGCCGACAAA | SEQ ID NO: 35 |
| Bcl-X | UAUGGAGCUGCAGAGGAUGdTdT | SEQ ID NO: 36 |
| Raf-1 | TTTGAATATCTGTGCTGAGAACACA GTTCTCAGCACAGATATTCTTTTT | SEQ ID NO: 37 |
| Heat shock transcription factor 2 | AATGAGAAAAGCAAAAGGTGCCCTGTCTC | SEQ ID NO: 38 |
| IGFBP3 | AAUCAUCAUCAAGAAAGGGCA | SEQ ID NO: 39 |
| Thioredoxin | AUGACUGUCAGGAUGUUGCdTdT | SEQ ID NO: 40 |
| CD44 | GAACGAAUCCUGAAGACAUCU | SEQ ID NO: 41 |
| MMP14 | AAGCCTGGCTACAGCAATATGCCTGTCTC | SEQ ID NO: 42 |
| MAPKAPK2 | UGACCAUCACCGAGUUUAUdTdT | SEQ ID NO: 43 |
| FGFR1 | AAGTCGGACGCAACAGAGAAA | SEQ ID NO: 44 |
| ERBB2 | CUACCUUUCUACGGACGUGdTdT | SEQ ID NO: 45 |
| BCL2L1 | CTGCCTAAGGCGGATTTGAAT | SEQ ID NO: 46 |
| ABL1 | TTAUUCCUUCUUCGGGAAGUC | SEQ ID NO: 47 |
| CEACAM1 | AACCTTCTGGAACCCGCCCAC | SEQ ID NO: 48 |
| CD9 | GAGCATCTTCGAGCAAGAA | SEQ ID NO: 49 |
| CD151 | CATGTGGCACCGTTTGCCT | SEQ ID NO: 50 |
| Caspase 8 | AACTACCAGAAAGGTATACCT | SEQ ID NO: 51 |
| BRCA1 | UCACAGUGUCCUUUAUGUAdTdT | SEQ ID NO: 52 |
| p53 | GCAUGAACCGGAGGCCCAUUT | SEQ ID NO: 53 |
| CEACAM6 | CCGGACAGTTCCATGTATA | SEQ ID NO: 54 |

The skilled artisan will realize that Table 3 represents a very small sampling of the total number of siRNA species known in the art, and that any such known siRNA may be utilized in the claimed methods and compositions.

Methods of Therapeutic Treatment

The methods and compositions are of use for treating disease states, such as cancer, autoimmune disease or immune dysfunction. The methods may comprise administering a therapeutically effective amount of a therapeutic antibody or fragment thereof or an immunoconjugate, either alone or in conjunction with one or more other therapeutic agents, administered either concurrently or sequentially.

Multimodal therapies may include therapy with other antibodies, such as anti-CD22, anti-CD19, anti-CD20, anti-CD21, anti-CD74, anti-CD80, anti-CD23, anti-CD45, anti-CD46, anti-MIF, anti-EGP-1, anti-CEACAM5, anti-CEACAM6, anti-pancreatic cancer mucin, anti-IGF-1R or anti-HLA-DR (including the invariant chain) antibodies in the form of naked antibodies, fusion proteins, or as immunoconjugates. Various antibodies of use, such as anti-CD19, anti-CD20, and anti-CD22 antibodies, are known to those of skill in the art. See, for example, Ghetie et al., *Cancer Res.* 48:2610 (1988); Hekman et al., *Cancer Immunol. Immunother.* 32:364 (1991); Longo, *Curr. Opin. Oncol.* 8:353 (1996), U.S. Pat. Nos. 5,798,554; 6,187,287; 6,306,393; 6,676,924; 7,109,304; 7,151,164; 7,230,084; 7,230,085; 7,238,785; 7,238,786; 7,282,567; 7,300,655; 7,312,318; 7,612,180; 7,501,498; the Examples section of each of which is incorporated herein by reference.

In another form of multimodal therapy, subjects receive therapeutic antibodies in conjunction with standard cancer chemotherapy. For example, "CVB" (1.5 g/m$^2$ cyclophosphamide, 200-400 mg/m² etoposide, and 150-200 mg/m² carmustine) is a regimen used to treat non-Hodgkin's lymphoma. Patti et al., *Eur. J. Haematol.* 51: 18 (1993). Other suitable combination chemotherapeutic regimens are well-known to those of skill in the art. See, for example, Freedman et al., "Non-Hodgkin's Lymphomas," in CANCER MEDICINE, VOLUME 2, 3rd Edition, Holland et al. (eds.), pages 2028-2068 (Lea & Febiger 1993). As an illustration, first generation chemotherapeutic regimens for treatment of intermediate-grade non-Hodgkin's lymphoma (NHL) include C-MOPP (cyclophosphamide, vincristine, procarbazine and prednisone) and CHOP (cyclophosphamide, doxorubicin, vincristine, and prednisone). A useful second generation chemotherapeutic regimen is m-BACOD (methotrexate, bleomycin, doxorubicin, cyclophosphamide, vincristine, dexamethasone and leucovorin), while a suitable third generation regimen is MACOP-B (methotrexate, doxorubicin, cyclophosphamide, vincristine, prednisone, bleomycin and leucovorin). Additional useful drugs include phenyl butyrate, bendamustine, and bryostatin-1.

In a preferred multimodal therapy, both chemotherapeutic drugs and cytokines are co-administered with a therapeutic antibody. The cytokines, chemotherapeutic drugs and therapeutic antibody can be administered in any order, or together.

Therapeutic antibodies or fragments thereof can be formulated according to known methods to prepare pharmaceutically useful compositions, whereby the therapeutic antibody is combined in a mixture with a pharmaceutically suitable excipient. Sterile phosphate-buffered saline is one example of a pharmaceutically suitable excipient. Other suitable excipients are well-known to those in the art. See, for example, Ansel et al., PHARMACEUTICAL DOSAGE FORMS AND DRUG DELIVERY SYSTEMS, 5th Edition (Lea & Febiger 1990), and Gennaro (ed.), REMINGTON'S PHARMACEUTICAL SCIENCES, 18th Edition (Mack Publishing Company 1990), and revised editions thereof.

The therapeutic antibody can be formulated for intravenous administration via, for example, bolus injection or continuous infusion. Preferably, the therapeutic antibody is infused over a period of less than about 4 hours, and more preferably, over a period of less than about 3 hours. For example, the first 25-50 mg could be infused within 30 minutes, preferably even 15 min, and the remainder infused over the next 2-3 hrs. Formulations for injection can be presented in unit dosage form, e.g., in ampoules or in multi-dose containers, with an added preservative. The compositions can take such forms as suspensions, solutions or emulsions in oily or aqueous vehicles, and can contain formulatory agents such as suspending, stabilizing and/or dispersing agents. Alternatively, the active ingredient can be in powder form for constitution with a suitable vehicle, e.g., sterile pyrogen-free water, before use.

The therapeutic antibody may also be administered to a mammal subcutaneously or even by other parenteral routes. Moreover, the administration may be by continuous infusion or by single or multiple boluses. Preferably, the therapeutic antibody is infused over a period of less than about 4 hours, and more preferably, over a period of less than about 3 hours.

More generally, the dosage of an administered therapeutic antibody for humans will vary depending upon such factors as the patient's age, weight, height, sex, general medical condition and previous medical history. It may be desirable to provide the recipient with a dosage of therapeutic antibody that is in the range of from about 1 mg/kg to 25 mg/kg as a single intravenous infusion, although a lower or higher dosage also may be administered as circumstances dictate. A dosage of 1-20 mg/kg for a 70 kg patient, for example, is 70-1,400 mg, or 41-824 mg/m² for a 1.7-m patient. The dosage may be repeated as needed, for example, once per week for 4-10 weeks, once per week for 8 weeks, or once per week for 4 weeks. It may also be given less frequently, such as every other week for several months, or monthly or quarterly for many months, as needed in a maintenance therapy.

Alternatively, a therapeutic antibody may be administered as one dosage every 2 or 3 weeks, repeated for a total of at least 3 dosages. Or, the therapeutic antibody may be administered twice per week for 4-6 weeks. If the dosage is lowered to approximately 200-300 mg/m² (340 mg per dosage for a 1.7-m patient, or 4.9 mg/kg for a 70 kg patient), it may be administered once or even twice weekly for 4 to 10 weeks. Alternatively, the dosage schedule may be decreased, namely every 2 or 3 weeks for 2-3 months. It has been determined, however, that even higher doses, such as 20 mg/kg once weekly or once every 2-3 weeks can be administered by slow i.v. infusion, for repeated dosing cycles. The dosing schedule can optionally be repeated at other intervals and dosage may be given through various parenteral routes, with appropriate adjustment of the dose and schedule.

Additional pharmaceutical methods may be employed to control the duration of action of the therapeutic immunoconjugate or naked antibody. Control release preparations can be prepared through the use of polymers to complex or adsorb the immunoconjugate or naked antibody. For example, biocompatible polymers include matrices of poly(ethylene-co-vinyl acetate) and matrices of a polyanhydride copolymer of a stearic acid dimer and sebacic acid. Sherwood et al., Bio/Technology 10: 1446 (1992). The rate of release of an immunoconjugate or antibody from such a matrix depends upon the molecular weight of the immunoconjugate or antibody, the amount of immunoconjugate or antibody within the matrix, and the size of dispersed particles. Saltzman et al., Biophys. J. 55: 163 (1989); Sherwood et al., supra. Other solid dosage forms are described in Ansel et al., PHARMACEUTICAL DOSAGE FORMS AND DRUG DELIVERY SYSTEMS, 5th Edition (Lea & Febiger 1990), and Gennaro (ed.), REMINGTON'S PHARMACEUTICAL SCIENCES, 18th Edition (Mack Publishing Company 1990), and revised editions thereof.

Cancer Therapy

In preferred embodiments, the antibodies, antibody fragments or immunoconjugates are of use for therapy of cancer. Examples of cancers include, but are not limited to, carcinoma, lymphoma, glioblastoma, melanoma, sarcoma, and leukemia, myeloma, or lymphoid malignancies. More particular examples of such cancers are noted below and include: squamous cell cancer (e.g., epithelial squamous cell cancer), Ewing sarcoma, Wilms tumor, astrocytomas, lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma multiforme, cervical cancer, ovarian cancer, liver cancer, bladder cancer, hepatoma, hepatocellular carcinoma, neuroendocrine tumors, medullary thyroid cancer, differentiated thyroid carcinoma, breast cancer, ovarian cancer, colon cancer, rectal cancer, endometrial cancer or uterine carcinoma, salivary gland carcinoma, kidney or renal cancer, prostate cancer, vulvar cancer, anal carcinoma, penile carcinoma, as well as head-and-neck cancer. The term "cancer" includes primary malignant cells or tumors (e.g., those whose cells have not migrated to sites in the subject's body other than the site of the original malignancy or tumor) and secondary malignant cells or tumors (e.g., those arising from metastasis, the migration of malignant cells or tumor cells to secondary sites that are different from the site of the original tumor).

Other examples of cancers or malignancies include, but are not limited to: Acute Childhood Lymphoblastic Leukemia, Acute Lymphoblastic Leukemia, Acute Lymphocytic Leukemia, Acute Myeloid Leukemia, Adrenocortical Carcinoma, Adult (Primary) Hepatocellular Cancer, Adult (Primary) Liver Cancer, Adult Acute Lymphocytic Leukemia, Adult Acute Myeloid Leukemia, Adult Hodgkin's Lymphoma, Adult Lymphocytic Leukemia, Adult Non-Hodgkin's Lymphoma, Adult Primary Liver Cancer, Adult Soft Tissue Sarcoma, AIDS-Related Lymphoma, AIDS-Related Malignancies, Anal Cancer, Astrocytoma, Bile Duct Cancer, Bladder Cancer, Bone Cancer, Brain Stem Glioma, Brain Tumors, Breast Cancer, Cancer of the Renal Pelvis and Ureter, Central Nervous System (Primary) Lymphoma, Central Nervous System Lymphoma, Cerebellar Astrocytoma, Cerebral Astrocytoma, Cervical Cancer, Childhood (Primary) Hepatocellular Cancer, Childhood (Primary) Liver Cancer, Childhood Acute Lymphoblastic Leukemia, Childhood Acute Myeloid Leukemia, Childhood Brain Stem Glioma, Childhood Cerebellar Astrocytoma, Childhood Cerebral Astrocytoma, Childhood Extracranial Germ Cell Tumors, Childhood Hodgkin's Disease, Childhood Hodgkin's Lymphoma, Childhood Hypothalamic and Visual Pathway Glioma, Childhood Lymphoblastic Leukemia, Childhood Medulloblastoma, Childhood Non-Hodgkin's Lymphoma, Childhood Pineal and Supratentorial Primitive Neuroectodermal Tumors, Childhood Primary Liver Cancer, Childhood Rhabdomyosarcoma, Childhood Soft Tissue Sarcoma, Childhood Visual Pathway and Hypothalamic Glioma, Chronic Lymphocytic Leukemia, Chronic Myelogenous Leukemia, Colon Cancer, Cutaneous T-Cell Lymphoma, Endocrine Pancreas Islet Cell Carcinoma, Endometrial Cancer, Ependymoma, Epithelial Cancer, Esophageal Cancer, Ewing's Sarcoma and Related Tumors, Exocrine Pancreatic Cancer, Extracranial Germ Cell Tumor, Extragonadal Germ Cell Tumor, Extrahepatic Bile Duct Cancer, Eye Cancer, Female Breast Cancer, Gaucher's Disease, Gallbladder Cancer, Gastric Cancer, Gastrointestinal Carcinoid Tumor, Gastrointestinal Tumors, Germ Cell Tumors, Gestational Trophoblastic Tumor, Hairy Cell Leukemia, Head and Neck Cancer, Hepatocellular Cancer, Hodgkin's Lymphoma, Hypergammaglobulinemia, Hypopharyngeal Cancer, Intestinal Cancers, Intraocular Melanoma, Islet Cell Carcinoma, Islet Cell Pancreatic Cancer, Kaposi's Sarcoma, Kidney Cancer, Laryngeal Cancer, Lip and Oral Cavity Cancer, Liver Cancer, Lung Cancer, Lymphoproliferative Disorders, Macroglobulinemia, Male Breast Cancer, Malignant Mesothelioma, Malignant Thymoma, Medulloblastoma, Melanoma, Mesothelioma, Metastatic Occult Primary Squamous Neck Cancer, Metastatic Primary Squamous Neck Cancer, Metastatic Squamous Neck Cancer, Multiple Myeloma, Multiple Myeloma/Plasma Cell Neoplasm, Myelodysplastic Syndrome, Myelogenous Leukemia, Myeloid Leukemia, Myeloproliferative Disorders, Nasal Cavity and Paranasal Sinus Cancer, Nasopharyngeal Cancer, Neuroblastoma, Non-Hodgkin's Lymphoma, Nonmelanoma Skin Cancer, Non-Small Cell Lung Cancer, Occult Primary Metastatic Squamous Neck Cancer, Oropharyngeal Cancer, Osteo-/Malignant Fibrous Sarcoma, Osteosarcoma/Malignant Fibrous Histiocytoma, Osteosarcoma/Malignant Fibrous Histiocytoma of Bone, Ovarian Epithelial Cancer, Ovarian Germ Cell Tumor, Ovarian Low Malignant Potential Tumor, Pancreatic Cancer, Paraproteinemias, Polycythemia vera, Parathyroid Cancer, Penile Cancer, Pheochromocytoma, Pituitary Tumor, Primary Central Nervous System Lymphoma, Primary Liver Cancer, Prostate Cancer, Rectal Cancer, Renal Cell Cancer, Renal Pelvis and Ureter Cancer, Retinoblastoma, Rhabdomyosarcoma, Salivary Gland Cancer, Sarcoidosis Sarcomas, Sezary Syndrome, Skin Cancer, Small Cell Lung Cancer, Small Intestine Cancer, Soft Tissue Sarcoma, Squamous Neck Cancer, Stomach Cancer, Supratentorial Primitive Neuroectodermal and Pineal Tumors, T-Cell Lymphoma, Testicular Cancer, Thymoma, Thyroid Cancer, Transitional Cell Cancer of the Renal Pelvis and Ureter, Transitional Renal Pelvis and Ureter Cancer, Trophoblastic Tumors, Ureter and Renal Pelvis Cell Cancer, Urethral. Cancer, Uterine Cancer, Uterine Sarcoma, Vaginal Cancer, Visual Pathway and Hypothalamic Glioma, Vulvar Cancer, Waldenstrom's Macroglobulinemia, Wilms' Tumor, and any other hyperproliferative disease, besides neoplasia, located in an organ system listed above.

The methods and compositions described and claimed herein may be used to treat malignant or premalignant conditions and to prevent progression to a neoplastic or malignant state, including but not limited to those disorders described above. Such uses are indicated in conditions known or suspected of preceding progression to neoplasia or cancer, in particular, where non-neoplastic cell growth consisting of hyperplasia, metaplasia, or most particularly, dysplasia has occurred (for review of such abnormal growth conditions, see Robbins and Angell, Basic Pathology, 2d Ed., W. B. Saunders Co., Philadelphia, pp. 68-79 (1976)).

Dysplasia is frequently a forerunner of cancer, and is found mainly in the epithelia. It is the most disorderly form of non-neoplastic cell growth, involving a loss in individual cell uniformity and in the architectural orientation of cells. Dysplasia characteristically occurs where there exists chronic irritation or inflammation. Dysplastic disorders which can be treated include, but are not limited to, anhidrotic ectodermal dysplasia, anterofacial dysplasia, asphyxiating thoracic dysplasia, atriodigital dysplasia, bronchopulmonary dysplasia, cerebral dysplasia, cervical dysplasia, chondroectodermal dysplasia, cleidocranial dysplasia, congenital ectodermal dysplasia, craniodiaphysial dysplasia, craniocarpotarsal dysplasia, craniometaphysial dysplasia, dentin dysplasia, diaphysial dysplasia, ectodermal dysplasia, enamel dysplasia, encephalo-ophthalmic dysplasia, dysplasia epiphysialis hemimelia, dysplasia epiphysialis multiplex, dysplasia epiphysialis punctata, epithelial dysplasia, faciodigitogenital dysplasia, familial fibrous dysplasia of jaws, familial white folded dysplasia, fibromuscular dysplasia, fibrous dysplasia of bone, florid osseous dysplasia, hereditary renal-retinal dysplasia, hidrotic ectodermal dysplasia, hypohidrotic ectodermal dysplasia, lymphogenic thymic dysplasia, mammary dysplasia, mandibulofacial dysplasia, metaphysial dysplasia, Mondini dysplasia, monostotic fibrous dysplasia, mucoepithelial dysplasia, multiple epiphysial dysplasia, oculoauriculovertebral dysplasia, oculodentodigital dysplasia, oculovertebral dysplasia, odontogenic dysplasia, opthalmomandibulomelic dysplasia, periapical cemental dysplasia, polyostotic fibrous dysplasia, pseudoachondroplastic spondyloepiphysial dysplasia, retinal dysplasia, septo-optic dysplasia, spondyloepiphysial dysplasia, and ventriculoradial dysplasia.

Additional pre-neoplastic disorders which can be treated include, but are not limited to, benign dysproliferative disorders (e.g., benign tumors, fibrocystic conditions, tissue hypertrophy, intestinal polyps or adenomas, and esophageal dysplasia), leukoplakia, keratoses, Bowen's disease, Farmer's Skin, solar cheilitis, and solar keratosis.

In preferred embodiments, the method of the invention is used to inhibit growth, progression, and/or metastasis of cancers, in particular those listed above.

Additional hyperproliferative diseases, disorders, and/or conditions include, but are not limited to, progression, and/or metastases of malignancies and related disorders such as leukemia (including acute leukemias (e.g., acute lymphocytic leukemia, acute myelocytic leukemia (including myeloblastic, promyelocytic, myelomonocytic, monocytic, and erythroleukemia)) and chronic leukemias (e.g., chronic myelocytic (granulocytic) leukemia and chronic lymphocytic leukemia)), polycythemia vera, lymphomas (e.g., Hodgkin's disease and non-Hodgkin's disease), multiple myeloma, Waldenstrom's macroglobulinemia, heavy chain disease, and solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, emangioblastoma, acoustic neuroma, oligodendroglioma, meningioma, melanoma, neuroblastoma, and retinoblastoma.

Therapy of Autoimmune Disease

Anti-CD74 antibodies or immunoconjugates can be used to treat immune dysregulation disease and related autoimmune diseases, including Class-III autoimmune diseases, immune-mediated thrombocytopenias, such as acute idiopathic thrombocytopenic purpura and chronic idiopathic thrombocytopenic purpura, dermatomyositis, Sjogren's syndrome, multiple sclerosis, Sydenham's chorea, myasthenia gravis, systemic lupus erythematosus, lupus nephritis, rheumatic fever, polyglandular syndromes, bullous pemphigoid, diabetes mellitus, Henoch-Schonlein purpura, post-streptococcal nephritis, erythema nodosum, Takayasu's arteritis, Addison's disease, rheumatoid arthritis, sarcoidosis, ulcerative colitis, erythema multiforme, IgA nephropathy, polyarteritis nodosa, ankylosing spondylitis, Goodpasture's syndrome, thromboangitis obliterans, primary biliary cirrhosis, Hashimoto's thyroiditis, thyrotoxicosis, scleroderma, chronic active hepatitis, polymyositis/dermatomyositis, polychondritis, pemphigus vulgaris, Wegener's granulomatosis, membranous nephropathy, amyotrophic lateral sclerosis, tabes dorsalis, giant cell arteritis/polymyalgia, pernicious anemia, rapidly progressive glomerulonephritis and fibrosing alveolitis.

EXAMPLES

Various embodiments of the present invention are illustrated by the following examples, without limiting the scope thereof.

Example 1

FTY720 Modulates CD74 Expression and Sensitizes Mantle Cell Lymphoma Cells to Anti-CD74 Antibody-Mediated Cell Death Mantle cell lymphoma (MCL) is an aggressive B-cell malignancy with a short median survival despite multimodal therapy. FTY720, an immunosuppressive drug approved for the treatment of multiple sclerosis, promotes MCL cell death concurrent with down-modulation of phospho-Akt and Cyclin D1 and subsequent cell cycle arrest. However, the mechanism of FTY720-mediated MCL cell death has not previously been fully clarified. Here we show features of autophagy blockage by FTY720 treatment including accumulation of autolysosomes and increased LC3-II and p62 levels. We also show that FTY720-induced cell death is mediated by lysosomal membrane permeabilization with subsequent translocation of lysosomal hydrolases to the cytosol. FTY720-mediated disruption of the autophagic-lysosomal pathway led to increased levels of CD74, a therapeutic target in MCL that is degraded in the lysosomal compartment. This finding provided a rationale for examining combination therapy with FTY720 and milatuzumab, an anti-CD74 monoclonal antibody. Treatment of MCL cell lines and primary tumor cells with FTY720 and milatuzumab resulted in statistically significant enhanced cell death, which was synergistic in blastic variant MCL cell lines. Significant in vivo therapeutic activity of combination treatment was also demonstrated in a preclinical, in vivo model of MCL.

Introduction

Mantle cell lymphoma (MCL) is a B-cell malignancy that comprises 3-8% of Non-Hodgkin's lymphoma (NHL) cases diagnosed each year (Zelenetz, 2006, Ann Oncol 17 (suppl 4):iv12-14). Whereas the current treatment approach of using combination chemotherapeutic regimens can lead to complete remission, virtually all MCL patients relapse and outcome remains poor, with a median survival of only 3 years (Perez-Galan et al., Blood 117:26-38). The aggressive clinical behavior of MCL may be because of the complex pathobiology of the disease, which includes cell cycle dysregulation driven by cyclin D1 over-expression, alteration in the DNA damage response and constitutive activation of key antiapoptotic pathways such as phosphatidyl-inositol 3-kinase (PI3K)/Akt and nuclear factor-κB (NF-kB) (Martinez et al., 2003, 63:8226-32; Rudelius et al., 2006, Blood 108:1668-76; Pham et al., 2003, J Immunol 171:88-95; Rosenwald et al., 2003, Cancer Cell 3:185-97).

FTY720, (fingolimod), is a synthetic analog of sphingosine that was developed as an immunosuppressive agent (Mandala et al., 2002, Science 296:346-49; Tedesco-Silva et al., 2005, Transplantation 79:1553-60). FTY720 has been approved by the FDA to treat relapsed multiple sclerosis (Cohen et al., 2010, N Engl J Med 362:402-15). We have recently reported that FTY720 has in vitro and in vivo activity in MCL (Liu et al. 2010, Clin Cancer Res 16:3182-92). FTY720 promoted death of MCL cell lines and primary MCL tumor cells via caspase-independent radical oxygen species (ROS) generation, down-modulation of phospho-Akt (p-Akt) and Cyclin D1, with accumulation of cells in $G_0/G_1$ and $G_2/M$ phases of the cell cycle. Whereas these data provided information explaining the antitumor activity of FTY720, the effects of this drug on the pathophysiology of MCL required further characterization.

Here we show that FTY720 inhibits autophagic flux and induces MCL cell death through lysosomal membrane permeabilization and subsequent translocation of lysosomal hydrolases in the cytosol. Because the autophagy-lysosomal pathway represents an important regulatory mechanism governing the cellular proteosome, we hypothesized that disruption of this pathway would lead to the discovery of other proteins that could be targeted to enhance FTY720 antitumor activity. We examined CD74, a type II transmembrane glycoprotein that acts as a major histocompatibility complex (MHC) class II chaperone (Matza et al., 2001, J Biol Chem 276:27203-06). After synthesis, CD74 associates with the MHC class IIα and MHC class IIβ heterodimers in the endoplasmic reticulum (ER), exits the ER, and transfers to the lysosomal compartment where it is released from MHC class II molecules and degraded (Id.). CD74 also plays an important role as a survival receptor in the maturation and proliferation of B-cells by activating the PI3K/Akt and the NF-kβ pathway (Matza et al., 2001, J Biol Chem 276:27203-06; Starlets et al., 2006, Blood 107:4807-16; Stein et al., 2007, Clin Cancer Res 13:5556s-63s). We recently reported that CD74 is expressed on MCL cell lines and primary tumor cells and that milatuzumab, a fully humanized monoclonal antibody (mAb) specific for CD74, has significant anti-MCL activity in vitro and in vivo. (Alinari et al., 2011, Blood 117:4530-41). Here, we show that FTY720 treatment increases CD74 expression by blocking its degradation in the lysosomal compartment, generating more CD74 available for milatuzumab binding.

Material and Methods

Reagents.

FTY720 and OSU-2S were synthesized as previously described (Liu et al. 2010, Clin Cancer Res 16:3182-92; Omar et al., 2011, Hepatology 53:1943-58). Trastuzumab (GENENTECH, San Francisco, Calif.) was obtained commercially. Milatuzumab was provided by IMMUNOMEDICS (Morris Plains, N.J.). Chloroquine and acridine orange were purchased from SIGMA (St Louis, Mo.). Rapamycin was purchased from CALBIOCHEM (San Diego, Calif.). LYSOTRACKER™ green DND-26 and LYSOSENSOR™ green DND-189 were purchased from INVITROGEN (Rockville, Md.).

Primary Tumor Cells and Cell Lines.

Primary tumor cells were isolated from the peripheral blood/lymph nodes of patients with MCL. All patients studied were diagnosed with MCL according to the World Health Organization (WHO) classification of tumors (Swerdlow, 2008, World Health Organization Classification of Tumours of Haematopoetic and Lymphoid Tissues (ed $4^{th}$ ed.) Lyon, France, International Agency on Research for Cancer). All samples contained at least 85% of $CD19^+/CD20^+$ B cells detected by flow cytometry. Characteristics of MCL cell lines have been previously described (Drexler et al., 2006, Leuk Res 30:911-13). Primary tumor cells and MCL cell lines were incubated in RPMI 1640 media (INVITROGEN, Rockville, Md.), supplemented with 10% heat-inactivated fetal bovine serum, 2 mM L-glutamine and penicillin (100 U/mL)/streptomycin (100 μg/ml) at 37° C. in a humidified atmosphere of 5% $CO_2$.

Immunoblot Analysis.

Immunoblots were performed as previously described (Alinari et al., 2011, Blood 117:4530-41). Antibodies to the following proteins were used: actin and CD74 (SANTA CRUZ BIOTECHNOLOGY, Santa Cruz, Calif.); microtubule-associated protein 1 light chain 3 (LC3) and Beclin-1 (SIGMA-ALDRICH, St. Louis, Mo.); p62/SQSTM1 (Medical & Biological Laboratories CO., LTD, Japan). Cells were lysed in RIPA buffer [10 mM Tris-HCl (pH 7.4), 150 mM NaCl, 1% Triton X-100, 0.1% SDS and 1% sodium deoxycholate] containing protease and phosphatase inhibitors and cell lysates were clarified by centrifugation. Proteins were analyzed by immunoblot using standard procedures. 14% acrylamide gels were used to resolve LC3-I and LC3-II. The membranes were incubated with the indicated antibodies in PBS with 0.1% Tween 20 and 3% BSA. Goat anti-rabbit and goat anti-mouse Infrared IRDye®-labeled secondary antibodies (LI-COR) were used. Protein immunoreactivity was visualized and quantified using a Detection LI-COR/ODYSSEY® Infrared Imaging System Quantitative Real-Time Polymerase Chain Reaction (RT-PCR).

RNA extraction and RT-PCR were performed following standard methods (Lapalombella et al., 208, Blood 112:5180-89). RNA was isolated from approximately $1 \times 10^7$ cells using TRIZOL® reagent (INVITROGEN, Rockville, Md.) according to the manufacturer's directions. For each sample, cDNA was prepared using 2 ng of RNA and SUPERSCRIPT® First-Strand Synthesis System (INVITROGEN). Real-Time PCR was performed using pre-designed TAQMAN® Gene Expression Assay primer sets for CD74 (APPLIED BIOSYSTEMS, Foster City, Calif.) and GAPDH (APPLIED BIOSYSTEMS) and an ABI PRISM® 7700 sequence detection system (APPLIED BIOSYSTEMS). The expression of CD74 relative to the internal control gene was calculated by plotting the Ct (cycle number), and the average relative expression for each group was determined using the comparative method (2-Ct).

Synthesis of Fluorescence Labeled Milatuzumab.

Fluorescence labeled milatuzumab was synthesized as previously described (Alinari et al., 2011, Blood 117:4530-41). Antibody solution (1.0 mg/ml) was dialyzed against 0.1 M sodium bicarbonate buffer solution (pH=8.5) for 2 hours. NHS-rhodamine (10 mg/ml) in DMSO solution was added to the antibody solution in buffer ($NaHCO_3$, pH 8.3) for 1 hour at room temperature. The unbound free dyes were removed by column separation with a PD-10 desalting column (AMERSHAM BIOSCIENCES, Uppsala, Sweden). The resultant rhodamine-conjugated milatuzumab (red) was collected and sterilized via 200 nm polymer membrane filters. The stock solutions were kept at 4° C.

Confocal Fluorescence Microscopy and Live Cell Imaging.

MCL cells for confocal fluorescence microscopy were fixed and stained as previously described (Alinari et al., 2011, Blood 117:4530-41). Briefly, after exposure to drugs, cells were made adherent on a microscope slide by centrifugation. Immediately after cytospin, cells were fixed in cold acetone for two minutes. For CD74 immunofluorescence, the cells were incubated with rhodamine-conjugated milatuzumab. For LC3 staining, the cells were incubated in blocking solution (2% bovine serum albumin in phosphate-buffered saline) and stained for LC3 by incubating with the specific primary antibody overnight, at 4° C., followed by incubation with fluorescent secondary antibodies. ALEXA FLUOR® 488 (green) anti-rabbit was used for LC3. Nuclei were stained blue with DAPI (Vector laboratories, Burlingame, Calif.). Images were collected with an OLYMPUS® Fluoview 1000 Laser Scanning confocal microscope using a PlanApoN 60× oil-immersion objective (numerical aperture 1.42) and 4× optical zoom. All presented images were processed identically with OLYMPUS® Fluoview (v.2.1b) software. For quantification, 4 microscopic fields per slide were analyzed.

Nuclei count was performed using an edge constrained marker-controlled watershed for iterative fluorescence microscopic cell image splitting. For co-localization quantification, we used an algorithm developed by the Bioinformatics Core at Ohio State University (OSU). To compute the correlation value for the co-localization of the two fluorescence images we obtained two binary nuclei images (one for the red and the other for the green fluorescence image) by a certain threshold, which were denoted as R and G, respectively. The correlation value was calculated as the number of white pixels of (R&G) divided by the number of pixels of (R|G), where (R&G) is the intersection of R and G, and (R|G) is the union of R and G. To measure the fluorescence intensity for LC3 we used MetaMorph v.7.1.0 (MOLECULAR DEVICES, Sunnyvale, Calif.). The intensity was averaged relative to the number of cells per field.

For live cell imaging, cells were seeded at a density of $1.5 \times E^6$ in glass bottom, 35 mm petri dishes using RPMI 1640 growth media with 10% FBS and incubated 2 hours. Prior to live cell imaging, the growth media was exchanged with phenol red-free RPMI 1640 media containing 1 µM LYSOSENSOR™ green DND-189 and incubated for 30 min. FTY720 was added to the media following 20 minutes of image collection. Images were acquired sequentially every 10 min for a total of 5 hours using an excitation wavelength of 488 nm for 443 nm detection and 561 nm for 505 nm dye detection. Images were acquired with MetaMorph software that controlled a Visitech Infinity3 2D array scanning multi-beam confocal scanner system. Movies were produced using image z-stacks that were processed identically with MetaMorph.

Analysis by Flow Cytometry.

CD74 mean fluorescence intensity (MFI) and cell viability were evaluated as previously described (Alinari et al., 2011, Blood 117:4530-41; Alinari et al., 2009, MAbs 1:31-40). MCL cell lines were treated with FTY720, chloroquine (SIGMA, St Louis, Mo.) or rapamycin (CALBIOCHEM, San Diego, Calif.) for 8 and 24 hours and CD74 mean fluorescence intensity (MFI) was determined relative to a specific isotype control. After treatment, cells ($1 \times 10^6$) were washed in phosphate-buffered saline (PBS), stained with CD74-FITC (BD BIOSCIENCES, San Jose, Calif.) for 15 minutes at 4° C., then rinsed in PBS and analyzed by flow cytometry (EPICS-XL™; BECKMAN COULTER, Fullerton, Calif.). A total of 10,000 events were collected and analyzed using Windows Multiple Document Interface for Flow Cytometry (WinMDI, Scripps Research Institute, San Diego, Calif.).

To assess lysosomal volume, FTY720 treated cells were incubated with LYSOTRACKER™ green DND-26. To assess lysosomal membrane permeability, FTY720 treated cells were incubated with acridine orange (MOLECULAR PROBES; INVITROGEN). For analysis of cell viability, MCL cell lines ($0.5 \times 10^6$/ml) and primary cells ($1 \times 10^6$/ml) were treated with FTY720, milatuzumab, and the combination of both. Goat anti-human IgG cross-linker was added to the cell suspension 5 minutes after adding milatuzumab in five-fold excess of binding antibody. In addition, samples with no treatment were collected. Cell viability was measured at 24 hours by dual staining with annexin-V FITC and propidium iodide (PI). A total of 10,000 events were collected and analyzed using WinMDI.

Transmission Electron Microscopy (TEM).

Monolayer cells were grown in chamber slides in medium containing chloroquine (40 µM) or FTY720 (10 µM) for 12 hours. Prior to processing, the cells were fixed for 30 min in 2.5% glutaraldehyde in 0.1 M phosphate buffer pH 7.4. Further processing was thereafter performed by OSU Campus Microscopy and Imaging Facility. Images were obtained with a PEI TECHNAI™ G2 Spirit Transmission Electron Microscope.

Evaluation of the In Vivo Therapeutic Activity of FTY720 in Combination with Milatuzumab.

To examine the in vivo activity of FTY720 and milatuzumab, our previously described preclinical model of human MCL using the SCID mouse was used (Liu et al. 2010, Clin Cancer Res 16:3182-92). Six to eight-week old female SCID mice (cb17 scid/scid) were purchased from Taconic Farms (Hudson, N.Y.) and maintained in pathogen-free, isolation cages. All animals were depleted of murine NK cells with intra-peritoneal (i.p.) injections of 0.2 mg of rat anti-mouse interleukin-2 receptor β monoclonal antibody (TMβ1) 1 day prior to engraftment with human tumor cell lines and then every week. Forty-eight hours post intravenous injection of $40 \times 10^6$ Jeko cells via tail vein, 50 mice were randomly distributed into 10 cages. Animals in groups of ten were treated starting at day 15 after engraftment. The first two groups served as a control and received either placebo (saline), 100 µl i.p. every day for 2 weeks or trastuzumab (15 mg/kg) every three days, via i.p. injection. The third group was treated with FTY720 (5 mg/kg) every day for 2 weeks via i.p. The fourth group received milatuzumab (15 mg/kg) every three days, via i.p. injection. The fifth group received the combination of FTY720 and milatuzumab. Animals were monitored daily for signs of tumor burden, including hind limb paralysis, respiratory distress, weight loss, ruffled coat, and distended abdomen. Body weight was measured weekly for the first 3 weeks and then daily. Animals were sacrificed and subjected to histopathologic evaluation to confirm the presence of MCL if they exhibited either hind limb paralysis, a 30% reduction in body mass, a 10% reduction in body mass together with respiratory distress, ruffled coat and/or lethargic behavior. The primary end point of the study was survival defined as the time from engraftment to the development of the defined clinical criteria leading to removal from the study.

Results

FTY720 Blocks the Autophagic Flux in MCL Cell Lines.

Autophagic flux describes a physiologic sequential process through which cells degrade and recycle proteins and cytoplasmic organelles, thus promoting cell survival in stressful conditions (Mizushima et al., 2008, Nature 451:1069-75; Levvine & Yuan, 2005, J Clin Invest 115:2679-88). It has been reported that FTY720 induces autophagy in ovarian cancer cell lines and acute lymphoblastic leukemia (ALL) cells, an effect that protected tumor cells from FTY720-mediated cell death (Zhang et al., 2010, Autophagy 6:1157-67; Wallington-Beddoe et al., 2011, Autophagy 7:707-15). We therefore evaluated the influence of FTY720 treatment on autophagic flux in MCL cells by examining changes in LC3, Beclin-1 and p62 expression. LC3 is typically expressed in two forms: LC3-I, an 18 kDa form distributed throughout the cytosol under normal growth conditions, and LC3-II, a 16 kDa form that is incorporated into the membrane of expanding autophagosomes (Kabeya et al., 2000, EMBO J 195720-28). Therefore, the intracellular levels of LC3-II are typically used as a marker for autophagosome formation (Mizushima et al., 2010, Cell 140:313-26). Beclin-1 also participates in autophagosome formation and its expression is increased when autophagy is induced (Pattingre et al., 2005, Cell 122:927-39). The ubiquitin-binding protein p62 (SSTM1) directly binds proteins destined for autophagy-dependent degradation and facilitates protein localization in the autophagosomes by direct association with LC30II (Pankiv et al., 2007, J Biol Chem 282:24131-45). Both LC3-II and p62 are efficiently degraded by the autophagic-lysosome pathway (Pankiv et al., 2007, J Biol Chem 282:24131-45).

Given the variable biology and clinical behavior of MCL, four MCL cell lines were used in our experiments. The Mino cell line is derived from a patient with classic variant MCL (Lai et al., 2002, Leuk Res 26:849-55). Jeko-1, UPN-1 and Z-138 were derived from patients with blastoid variant MCL (Jeon et al., 1998, Br J Haematol 102:1323-26; M'Kacher et al., 2003, Cancer Genet Cytogenet 143:32-38; Estrov et al., 1998, Leuk Res 22:341-53).

Figure 1A:
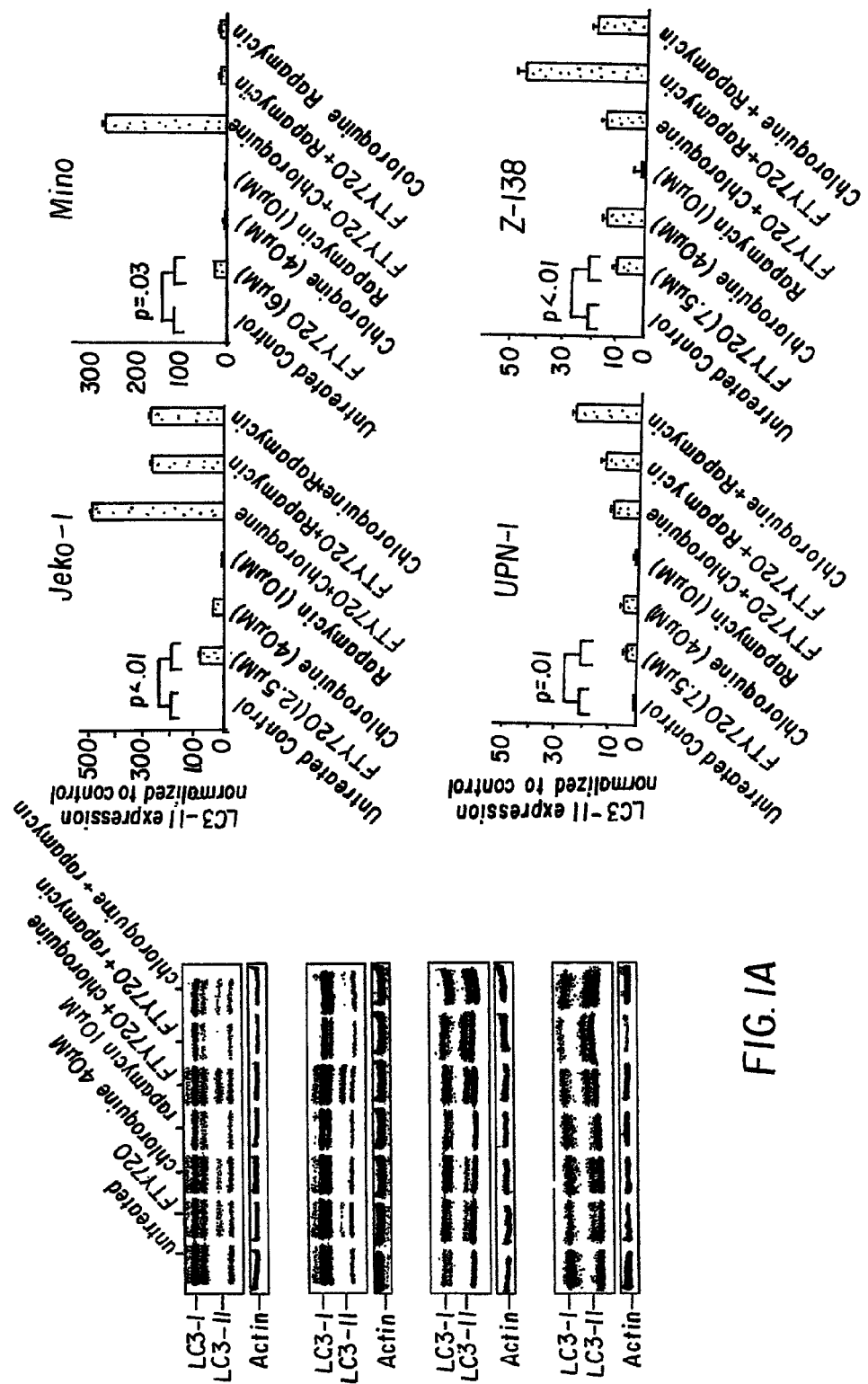
FIG. 1. FTY720 treatment blocks autophagy in MCL cells. (A) Four MCL cell lines were treated with FTY720 (Jeko-1, 12.5 µM; Mino, 7.5 µM; UPN-1, 12.5 µM; Z-138, 7.5 µM), chloroquine (40 µM), rapamycin (10 µM) or combinations, harvested at 24 hours, and immunoblotted for the microtubule-associated protein light-chain 3 (LC3-I and LC3-II). Actin was used as loading control. Representative histograms summarizing 3 independent experiments are also shown. Histograms were obtained using densitometry data for LC3-II levels in treated samples relative to untreated samples and normalized to the actin control. (B) The amount of total cellular LC3 was determined by confocal microscopy. Jeko-1, Mino, UPN-1 and Z-138 cells were treated with FTY720 at the indicated doses, chloroquine (40 µM), rapamycin (10 µM), or the combination of FTY720 and chloroquine for 4, 8 and 24 hours. LC3 fluorescence intensity was measured in 4 microscopic fields and integrated intensity was averaged relative to the number of cells per field (approximately 180-220 cells per condition). Representative histograms summarizing LC3 fluorescence intensity are shown. P values were calculated comparing FTY720, chloroquine and rapamycin treatment with untreated control. (C) Jeko-1, Mino, UPN-1 and Z-138 cells were treated with FTY720 at the dose indicated in panel A, chloroquine (40 µM), rapamycin (10 µM) or combinations, harvested at 24 hours and immunoblotted for p62. Actin was used as loading control. Levels of p62 normalized with actin are also shown in panel C. Representative histograms summarizing 3 independent experiments are also shown. Histograms were obtained using densitometry data for p62 levels in treated samples relative to untreated samples and normalized to the actin control.
Figure 1B:
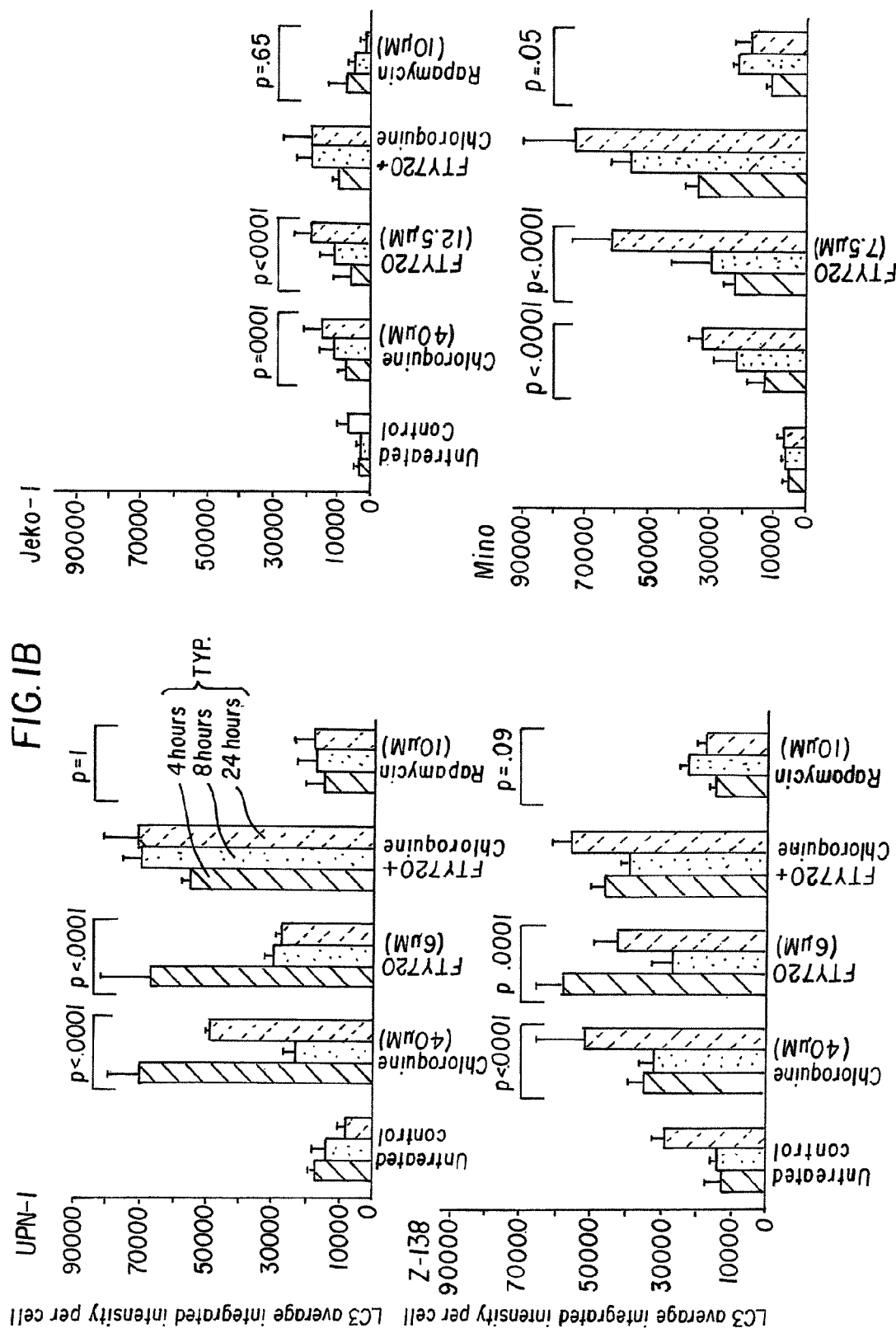

Whole cell lysates from MCL cell lines were evaluated by western blot for changes in LC3 isoforms after incubation with FTY720, chloroquine, rapamycin or combinations of these for 24 hours. Chloroquine inhibits acidification inside lysosomes and blocks the fusion of autophagosome and lysosomes, leading to inhibition of autophagic flux (Boya et al., 2005, Mol Cell Biol 25:1025-40). Rapamycin, an mTOR inhibitor, is a well established agent that accelerates autophagy (Takaeuchi et al., 2005, Cancer Res 65:3336-46). As shown in FIG. 1A, treatment with either FTY720 or chloroquine (Boya et al., 2005, Mol Cell Biol 25:1025-40), resulted in a significant increase in LC3-II levels. The differences in the amount of LC3-II between chloroquine-treated cells and untreated control represent the amount of LC3 that is delivered to the lysosome for degradation (Mizushima et al., 2010, Cell 140:313-26). The combination of FTY720 and chloroquine treatment resulted in a further increase of LC3-II levels, which may be because of either autophagy induction or inhibition of autophagic flux (Id.). In support of FTY720 as an autophagy blocker, treatment with rapamycin in combination with either FTY720 or chloroquine resulted in an increase of LC3-II compared with rapamycin alone (FIG. 1A), suggesting that FTY720 and chloroquine both block autophagic flux. Whereas the LC3 turnover assay should clarify if a drug induces or blocks autophagy, it has been proposed that this assay should not be the single method for evaluating autophagic flux (Id.). Because the amount of total cellular LC3 is inversely correlated with autophagic flux (Id.), confocal microscopy was used to evaluate the expression of total LC3 in Jeko-1, Mino, UPN-1 and Z-138 cells treated with FTY720, chloroquine, rapamycin, or the combination of FTY720 and chloroquine for 4, 8, and 24 hours. Fluorescence intensity was measured in 4 microscopic fields and integrated intensity was averaged relative to the number of cells per field. As shown in FIG. 1B, incubation of MCL cell lines with FTY720 or chloroquine resulted in a statistically significant increase in LC3 fluorescence intensity compared with untreated control cells for each of the 4 cell lines averaged across the 3 time points examined (P<0.0001). Representative images showed an increase in LC3 fluorescence (not shown), suggesting autophagosome/autolysosome accumulation in the presence of FTY720 or chloroquine.

We also evaluated the expression of Beclin-1, because the intracellular level of this protein is correlated with induction of autophagy (Id.). Beclin-1 levels remained unchanged after FTY720 treatment (1 and 4 hours incubation, data not shown) providing additional evidence that autophagy was not induced by FTY720 treatment.

Figure 1C:
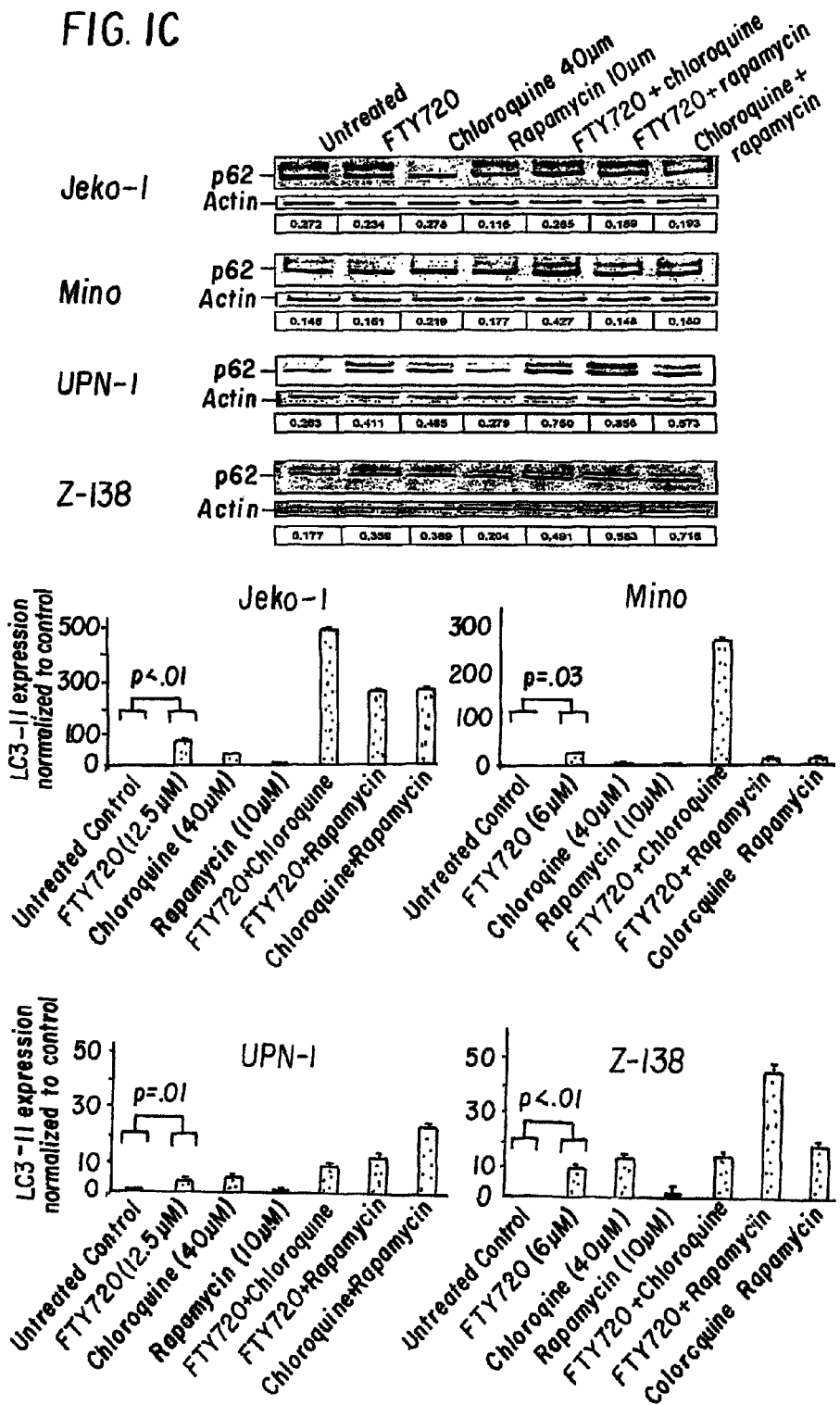

To further clarify the effect of FTY720 treatment on autophagy in MCL, we measured the expression of p62, which is inversely correlated with autophagic flux (Mizushima et al., 2010, Cell 140:313-26). As shown in FIG. 1C, incubation with either FTY720 or chloroquine for 24 hours resulted in a significant increase of p62 levels in UPN-1 and Z-138 cells, but not in Jeko-1 and Mino cell lines. However it must be noted that incubation of Jeko-1 and Mino cell lines with FY720 did not result in a decrease of p62 levels, which would otherwise suggest increase in autophagic flux. Interestingly, the combination of FTY720 and chloroquine resulted in a further increase of p62 levels in Mino and UPN-1 cell lines, confirming inhibition of autophagic flux in these cell lines.

We next examined ultrastructural morphologic changes in Jeko-1 and Mino cell lines treated with FTY720 using TEM. Normally growing cells are not expected to show accumulation of autophagosomes if the autophagic process operates efficiently. However, induction or blockage of autophagy results in accumulation of autophagosomes in the cytosol. In agreement with this, chloroquine-treated cells showed increased accumulation of autophagosomes compared with untreated cells, (data not shown). Interestingly, Jeko and Mino cells treated with FTY720 for 24 hours developed enlarged autolysosomes with characteristic enclosed cytoplasmic ultrastructures (Pankiv et al., 2007, J Biol Chem 282:24131-45), supporting the notion that FTY720 treatment results in blockade of the terminal stages of autophagy.

FTY720 is phosphorylated in vivo by sphingosine kinase 2 and converted to p-FTY720, which binds to sphingosine 1 phosphate (SIP) receptors (Liu et al. 2010, Clin Cancer Res 16:3182-92). As previously reported, p-FTY720 induces autophagy in prostate cancer cell lines through its interaction with S1P receptors (Chang et al., 2009, Am J Physiol Cell Physiol 297:C451-58). A non-phosphorylatable FTY720 derivative {OSU-2S [(S)-2-amino-2-(4-[(6-methylheptyl)-oxy]phenethyl)pentan-1-ol]} was recently developed at OSU (Omar et al., 2011, Hepatology 53:1943-58). OSU-2S exhibited cytotoxicity in MCL cell lines (data not shown) but because it is unable to be phosphorylated, will not interact with S1P receptors. We therefore sought to determine whether OSU-2S had the same effect as FTY720 on LC3 processing. Western blotting analysis was used to determine these effects in Jeko-1, Mino and Z-138 cell lines treated with OSU-2S for 24 hours. OSU-2S as well as FTY720 and chloroquine treatment resulted in increased levels of LC3-II (not shown). These observations led us conclude that FTY720 phosphorylation and its interaction with SP1 receptors are not required for FTY720-mediated cell death and blockage of autophagy in MCL cells.

In summary, we have shown that FTY720 increases the amount of total LC3 and p62 in UPN-1 and Z-138 and conversion of LC3-I to LC3-II without affecting Beclin-1 levels. These data, combined with our TEM images, suggest that FTY720 blocks the autophagic flux at a late stage, thus affecting the degradation process of autophagic cargo in MCL cells.

FTY720 Cytotoxicity Requires Lysosomal Membrane Permeabilization and Cathepsin Activity.

Figure 2A:
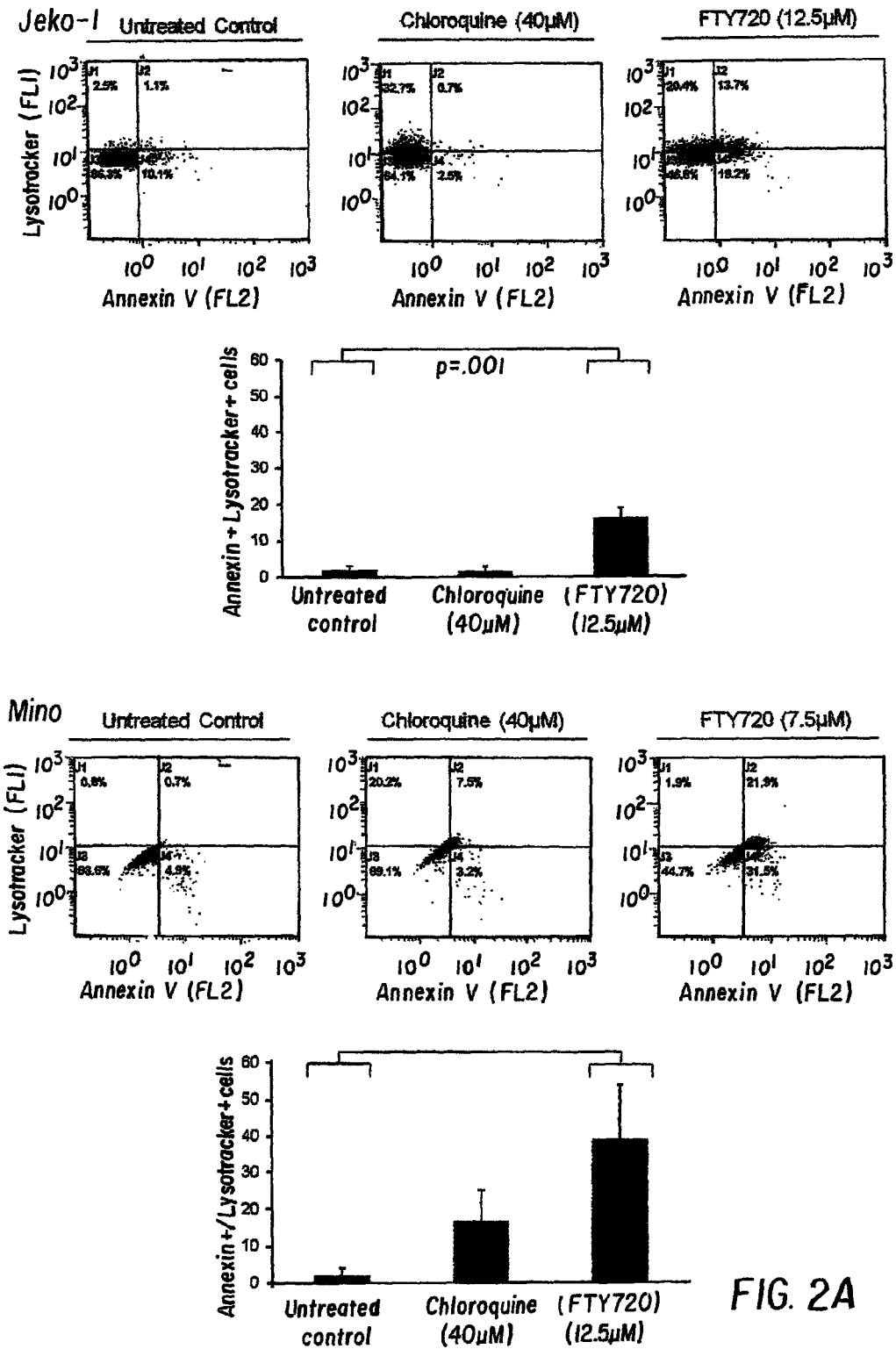
FIG. 2. FTY720 mediated cell death is dependent on lysosomal membrane permeabilization and cathepsin activity. (A) To determine the relationship between lysosomal volume and cell death, Jeko-1 and Mino cells were treated with FTY720 or chloroquine at the indicated concentrations for 8 hours. Cells were then labeled with LYSOTRACKER™ green and costained with annexin V-PE. Changes in lysosomal volume (FL1) and cell death (FL2) were assessed by 2-channel flow cytometry. Representative histograms summarizing the percentage of LYSOTRACKER™+/annexin V+ cells are also shown. (B) Jeko-1 (upper panel) and Mino (lower panel) cells were treated with FTY720, chloroquine, rapamycin, or combinations at the indicated concentrations for 8 hours. Cells were then stained with AO (1 µg/mL) for 15 minutes. The relative changes in FL1 fluorescence were assessed by flow cytometry. Representative histograms summarizing AO fluorescence intensity of MCL treated with FTY720, chloroquine, rapamycin or combinations are shown (MFI of treated cells is normalized to the untreated controls. (C) Jeko-1 and Mino cells were treated with FTY720 at the indicated concentration in the presence or absence of cathepsin inhibitor III (5 and 10 µM). Cell death was determined by annexin V/PI staining and flow cytometry at 8 hours. Data are shown as percentage of annexin V−/PI− cells (live cells).
Figure 2B:
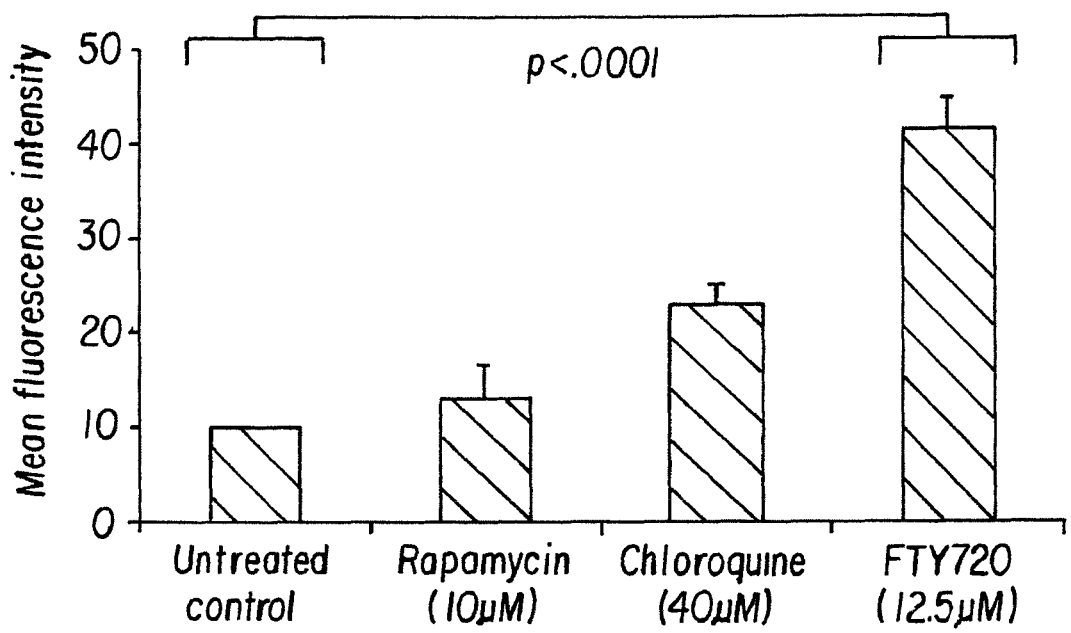
Figure 2B:
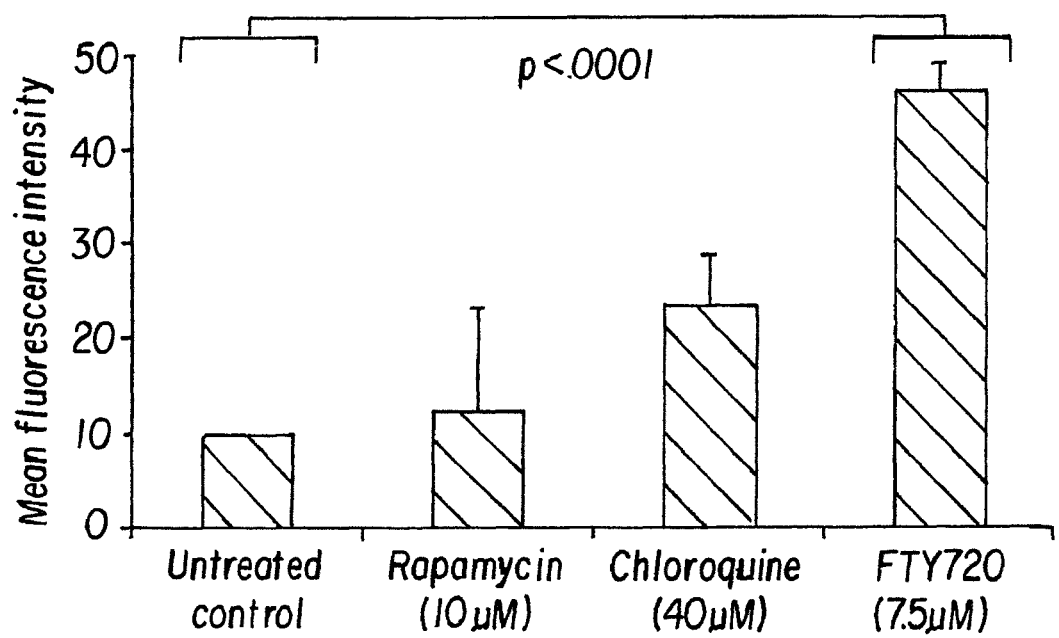

It is now well established that perturbation of lysosomal membrane function plays a central role in inducing nonapoptotic cell death (Kroemer et al., 2005, Nat Rev Cancer 5:886-97). Therefore, to characterize the involvement of the lysosomal compartment in FTY720-mediated cell death, FTY720 treated Jeko-1 and Mino cells (data not shown) were stained with LYSOSENSOR™, a lysosomal specific dye that emits green fluorescence in the presence of acidic pH. Images were collected every 10 minutes for 5 hours (not shown). These experiments revealed that LYSOSENSOR™ green fluorescence increased progressively after the addition of FTY720 (not shown), suggesting an enlargement of the lysosomal compartment. To correlate the lysosomal changes with cell death, 4 MCL cell lines (Jeko-1 and Mino, FIG. 2A; UPN-1 and Z-138, not shown) were treated with FTY720 for 8 hours, labeled with the lysosome-specific dye, LYSOTRACKER™ green, stained with annexin V-PE and then analyzed by flow cytometry. As shown in FIG. 2A, incubation of Jeko-1 and Mina cells with FTY720 induced an increase in LYSOTRACKER™ fluorescence, confirming an enlargement of lysosomes. Furthermore, the increase of LYSOTRACKER™ fluorescence coincided with annexin V positivity, suggesting a link between lysosomal enlargement and FTY720-mediated cell death. Unexpectedly, incubation of Jeko-1 and Mino cells with FTY720 for 8 and 24 hours was not associated with loss of mitochondrial transmembrane potential ($\Delta\Psi m$), as determined by JC-1 staining and flow cytometry (data not shown). This observation led us to hypothesize that the FTY720-induced ROS generation we previously reported was more likely a consequence of a FTY720-mediated lysosomal membrane permeabilization rather than mitochondrial membrane disruption.

To characterize the effects of FTY720 treatment on the lysosomal membrane, 4 MCL cell lines (Jeko-1 (upper trace, FIG. 2B), Mino (lower trace, FIG. 2B), UPN-1 and Z-138, not shown) were treated with FTY720 for 8 hours and then stained with acridine orange (AO) to label lysosomes. AO at acidic pH (i.e., lysosomal) fluoresces red, however, when AO leaks into a neutral pH (i.e., cytosolic), it causes an increase in green fluorescence that can be detected by flow cytometry. Representative histograms summarizing AO fluorescence intensity (FIG. 2B) show that FTY720 treatment of Jeko-1 and Mino cells followed by AO staining resulted in a significant increase of green fluorescence (FL1; P<0.001) compared with the untreated control cells. As expected, rapamycin did not induce an increase of green fluorescence. Interestingly, chloroquine treatment did induce a slight increase of green fluorescence although this was less pronounced compared to FTY720, suggesting that FTY720 and chloroquine have a similar effect on the lysosomal membrane. This led us to hypothesize that FTY720-mediated cell death was a consequence of the release of lysosomal contents into the cytosol.

Figure 2C:
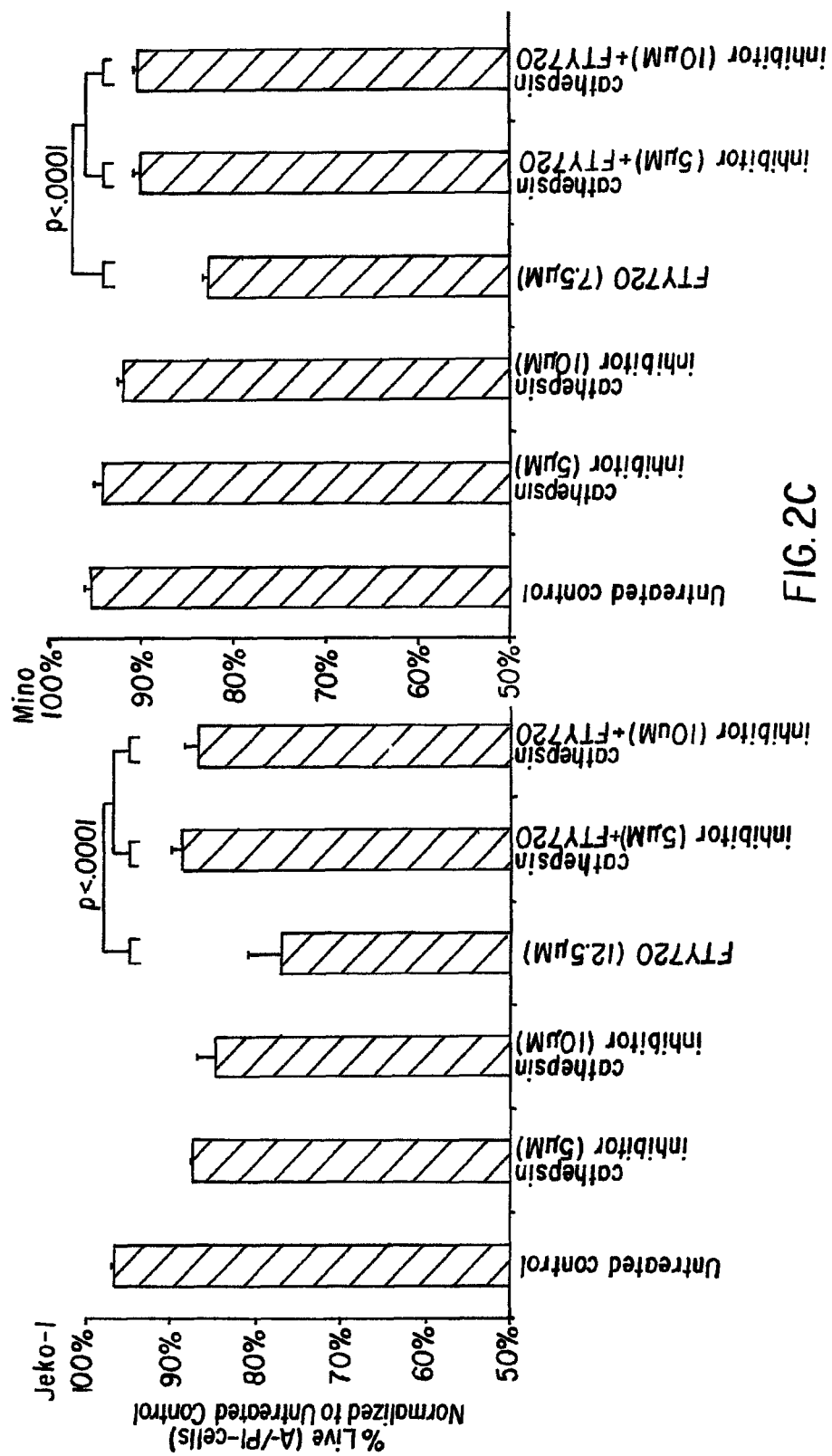

Cathepsins are the major lysosomal proteases (Reich et al., 2009, Immunol Lett 123:155-59). To evaluate the relevance of cathepsin activity in FTY720-mediated cell death, Jeko-1 and Mino cells were incubated with FTY720 in the presence of a specific cathepsin inhibitor (cathepsin inhibitor cocktail III) for 8 hours. As shown in FIG. 2C, the addition of the cathepsin inhibitor led to statistically significant increases in the viability of FTY720 treated Jeko-1 and Mino cells compared to FTY720 treatment alone (P<0.0001).

These data demonstrate that FTY720 treatment of MCL cells induces lysosomal membrane permeabilization and cathepsin release which contributed to FTY720-mediated cell death.

Treatment with FTY720 Increases CD74 Expression in MCL Cells.

We showed recently that MCL cell lines and primary MCL tumor cells express CD74 with a certain degree of variability (Jeko-1, 10,000 molecules/cell; Mino, 50,000 molecules/cell) (Alinari et al., 2011, Blood 117:4530-41). We also demonstrated that the CD74-specific antibody milatuzumab has significant anti-tumor preclinical activity in MCL and that the response to milatuzumab is strongly correlated with antigen density (Id.).

Figure 3A:
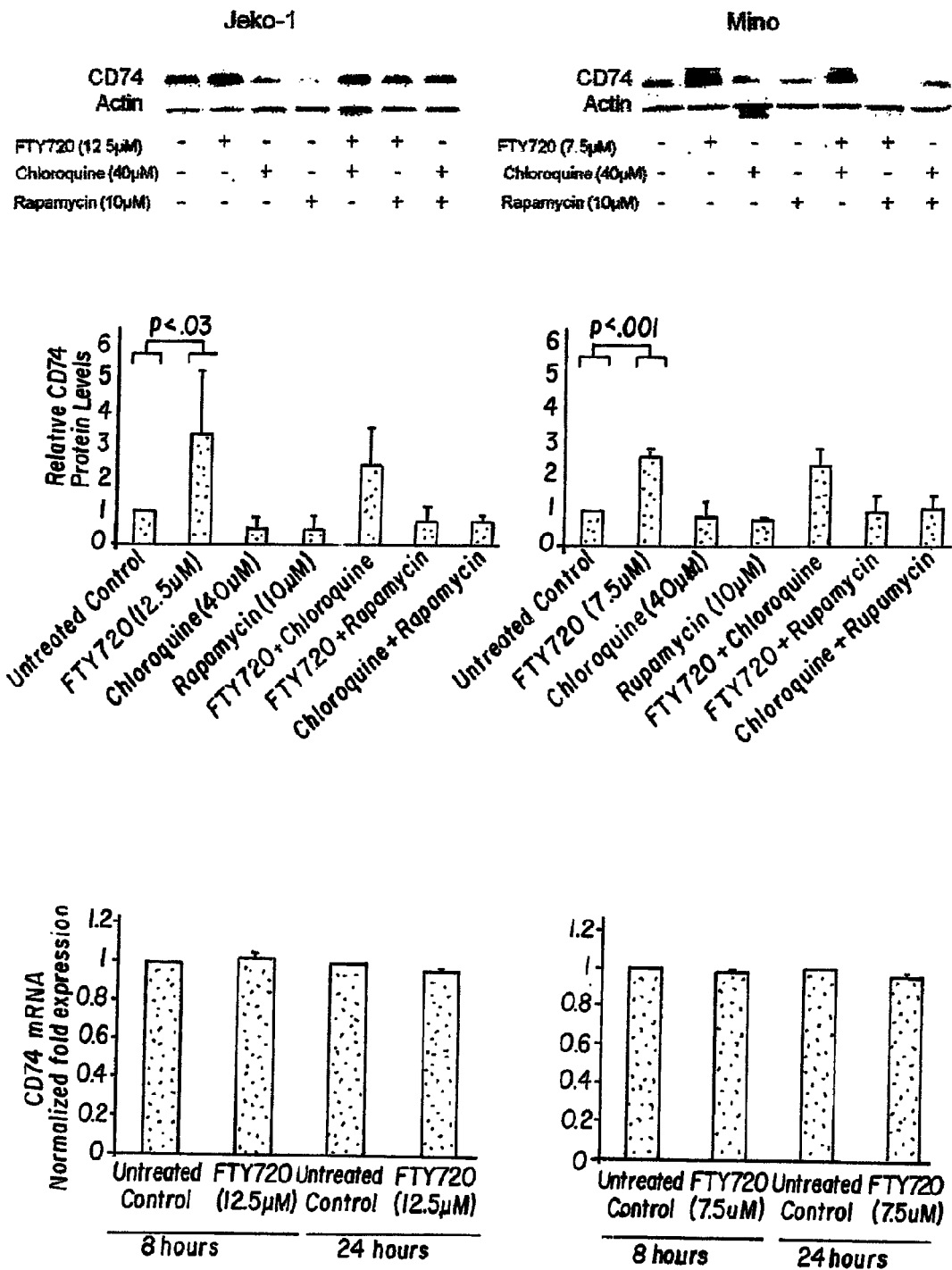

Because CD74 is degraded in the lysosomal compartment and because FTY720 blocks autophagy and induces lysosomal membrane permeabilization, we hypothesized that CD74 expression would increase after treatment of MCL cells with FTY720. Western blot analysis was used to determine the total cellular levels of CD74 in Jeko-1 and Mino cell lines treated with FTY720. As shown in FIG. 3A (top and middle panels), FTY720 treatment significantly increased the amount of CD74 in Jeko-1 and Mino cells. Chloroquine and rapamycin were used as controls for autophagic flux. RT-PCR data (FIG. 3A, bottom panels) indicated that no change in CD74 mRNA levels occurred in Jeko-1 or Mino cells treated with FTY720, fostering the hypothesis that FTY720 induced increase of CD74 levels through inhibition of its degradation rather than increased synthesis.

Figure 3B:
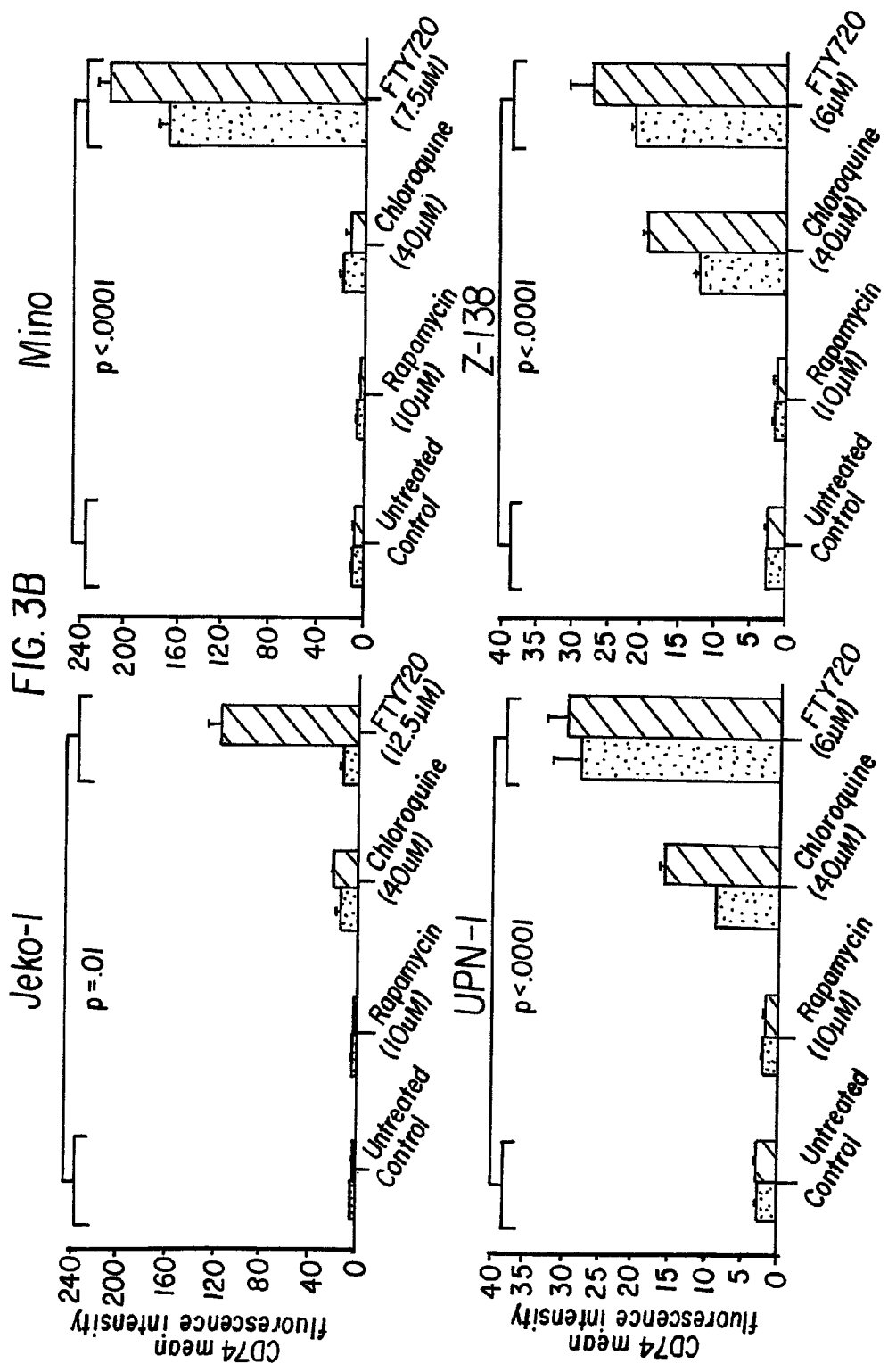

To determine the influence of FTY720 treatment on CD74 surface levels, Jeko-1 and Mino cells were incubated with FTY720, chloroquine or rapamycin for 8 and 24 hours. CD74 MFI values were determined by CD74-FITC staining and flow cytometry. FIG. 3B shows that FTY720 treatment of Jeko-1 and Mino cells induced a significant increase of CD74 MFI at 8 and 24 hours in both cell lines, compared with untreated control or rapamycin. Interestingly, chloroquine, but not rapamycin, also induced a slight increase of CD74 MFI, once again suggesting that FTY720 modulated CD74 expression by inhibiting its degradation. By 24 hours, rapamycin led to decreased CD74 MFI, suggesting that enhancing autophagic flux leads to more rapid loss of CD74 expression.

To verify these results, we performed the same experiment and evaluated total CD74 levels in Jeko-1, Mino, UPN-1 and Z-138 cells using confocal microscopy. As expected, incubation of Jeko-1 and Mino cells with non-immobilized rhodamine-conjugated milatuzumab (5 μg/ml), led to a rapid internalization of CD74 (not shown). Incubation with nonimmobilized rhodamine-conjugated milatuzumab and FTY720 led to a significant increase in total CD74 levels (not shown).

Figure 3C:
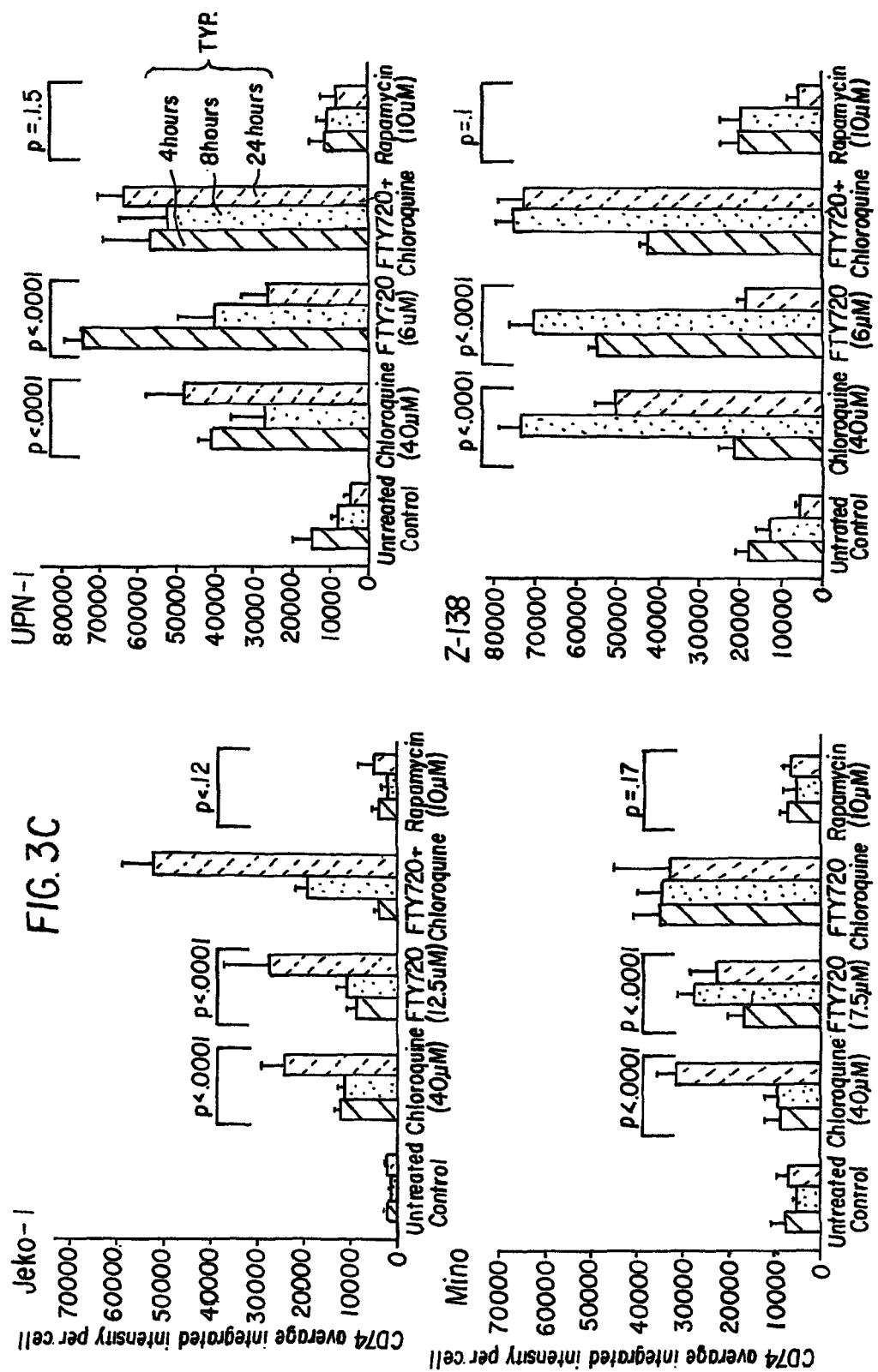

Representative histograms summarizing CD74 fluorescence intensities in Jeko-1, Mino, UPN-1 and Z-138 cells treated with FTY720, chloroquine, rapamycin or the combination of FTY720 and chloroquine for 4, 8 and 24 hours are shown in FIG. 3C. Fluorescence was measured in 4 microscopic fields and integrated intensity was averaged relative to the number of cells per field. As shown in FIG. 3C, incubation of the 4 MCL cell lines with FTY720 resulted in a statistically significant increase in CD74 fluorescence intensity compared with untreated control cells for each of the two cell lines averaged across the three time points examined (P<0.0001). A similar effect was observed in the presence of chloroquine confirming that both drugs inhibited CD74 degradation. Combination of FTY720 and chloroquine led to a further increased accumulation of CD74 compared with the two drugs alone. In contrast, treatment of cells with rapamycin did not cause CD74 accumulation. These data demonstrate for the first time that FTY720 increases cytosolic as well as surface CD74 levels in MCL, thus, potentially generating more CD74 available for milatuzumab targeted binding.

FTY720 Sensitizes MCL Cell Lines and Primary Patient Tumor Cells to Milatuzumab-Mediated Cytotoxicity.

Figure 4A:
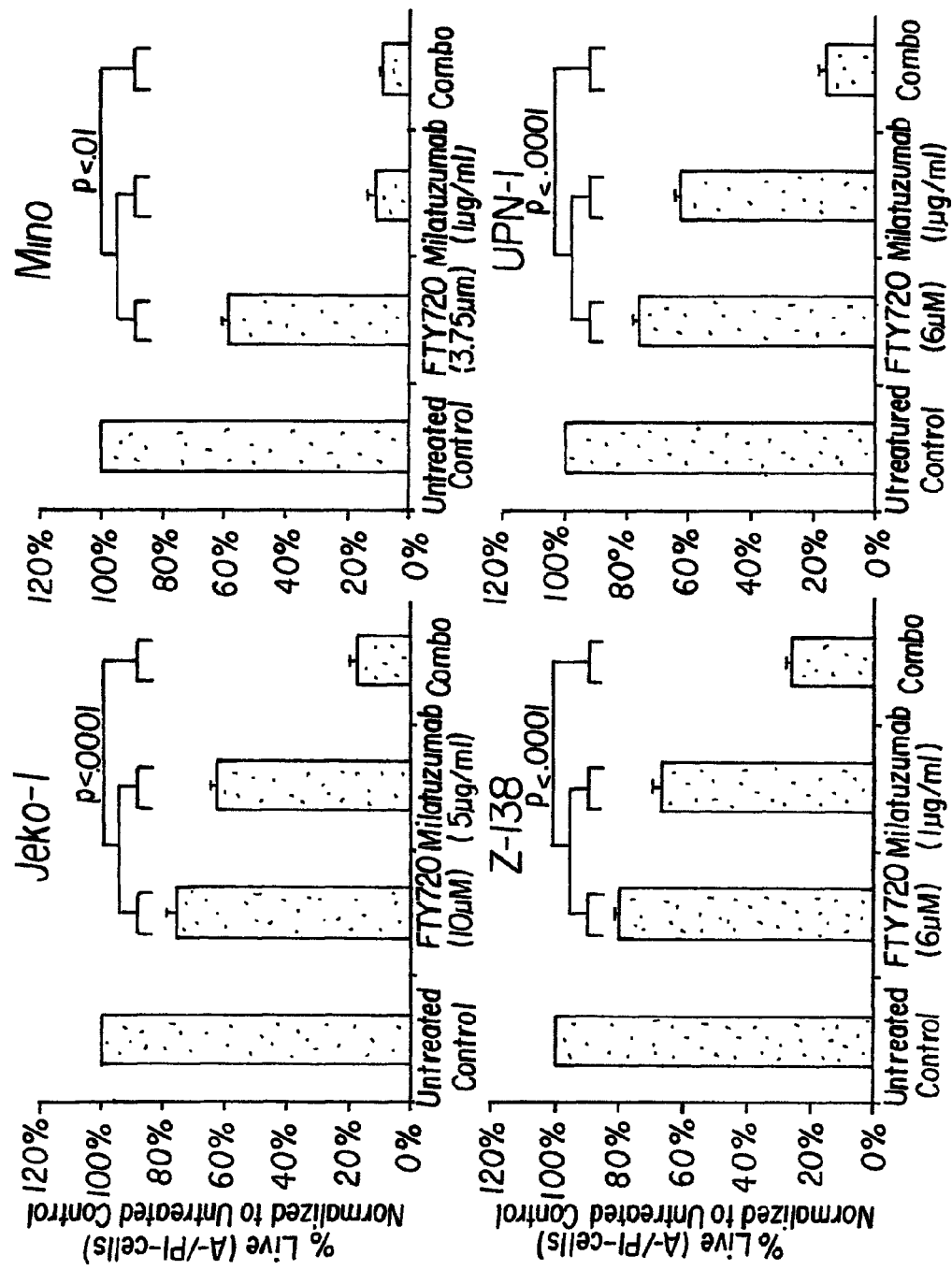

The in vitro survival of four MCL cell lines treated with FTY720, milatuzumab in the presence of a cross-linking antibody, and the combination of FTY720 and milatuzumab was determined at 24 hours by annexin-V/PI staining and flow cytometry. We previously performed dose titration experiments to determine the LC50 of the single agent approach with FTY720 and milatuzumab in MCL (Liu et al. 2010, Clin Cancer Res 16:3182-92; Alinari et al., 2011, Blood 117:4530-41). For Jeko-1 we used FTY720 at 10 μM (LC50: 12.5 μM), for Z-138 and UPN-1 we used 6 μM (LC50: 7.5 μM), and for Mino we used 3.75 μM (LC50: 7.5 μM). The dose of milatuzumab was not decreased from 5-1 μg/ml in Jeko-1 cells, which display the lowest CD74 expression. We used milatuzumab at 1 μg/ml for the other three cell lines. As shown in FIG. 4A, incubation of the four MCL cell lines with FTY720 and milatuzumab at the indicated doses resulted in a statistically significant decrease in cell viability compared with either single agent alone for each of the four cell lines (P<0.01). The Jeko-1, Z-138 and UPN-1 cell lines, which were derived from patients with blastoid variant MCL, were the cell lines in which combination treatment resulted in synergistic killing, although both FTY720 and milatuzumab as single agents showed only modest activity.

Figure 4C:
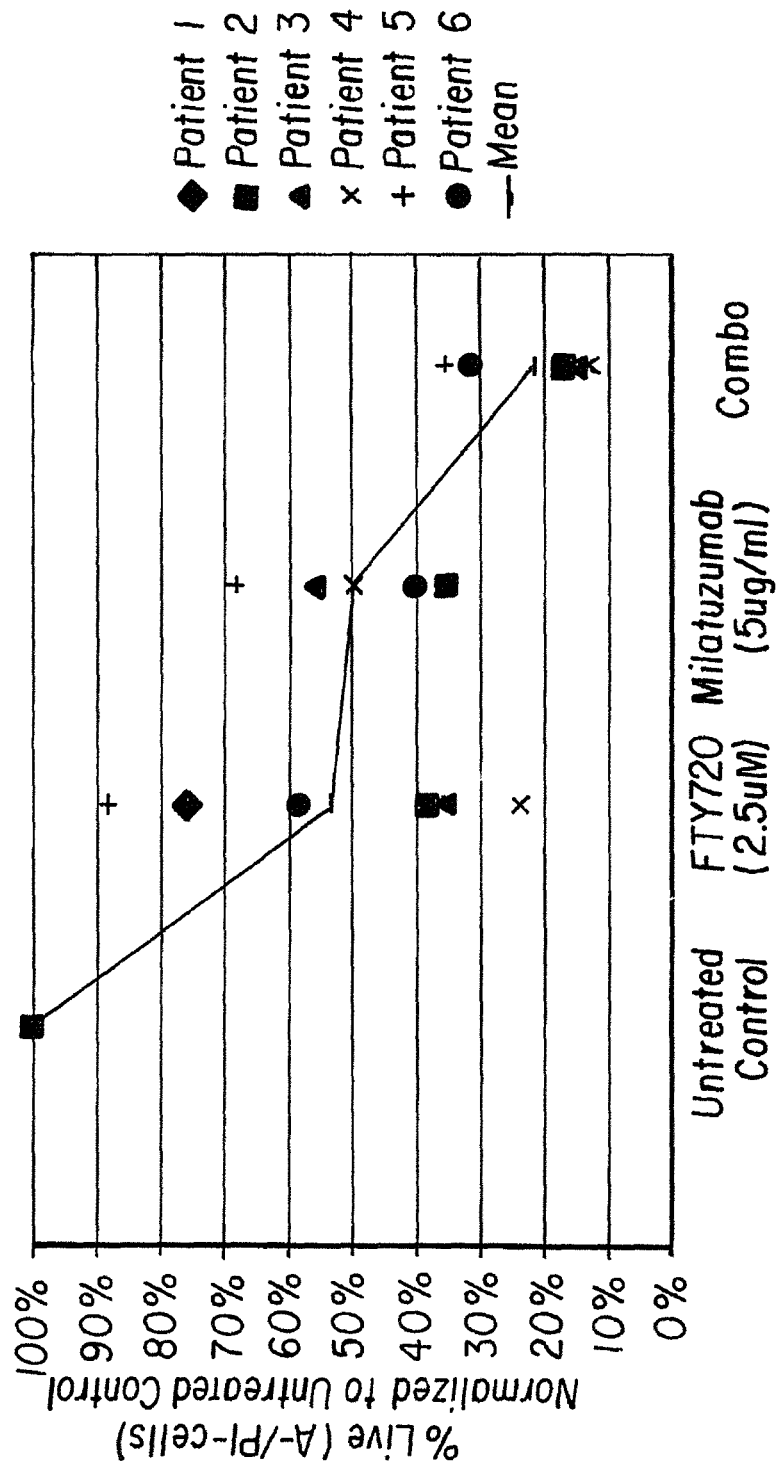
Figure 4D:
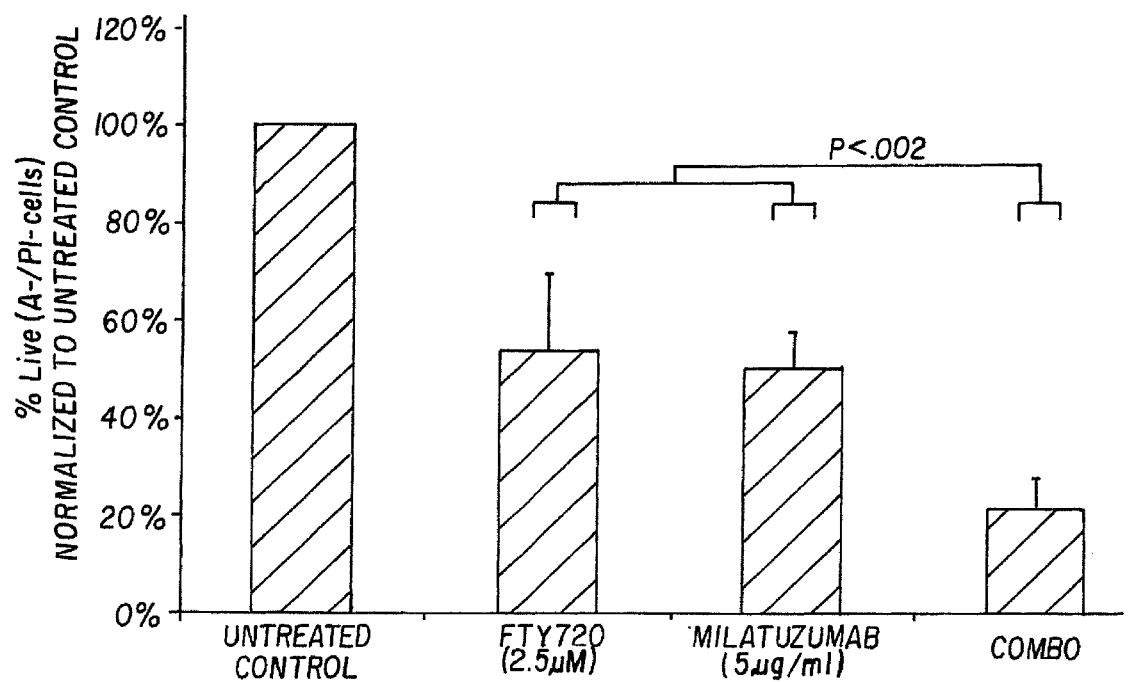

We next compared the effects of FTY720 and milatuzumab as single agents and in combination on primary tumor cells from six MCL patients, three patients with blastoid variant MCL and three patients with classic MCL (clinical characteristics summarized in FIG. 4B), after 24 hours of incubation with FTY720 (2.5 µM), immobilized milatuzumab (5 µg/ml), or combination treatment. Whereas the dose of FTY720 used was half the LC50 dose previously determined in primary MCL cells, combination treatment induced an average 78.5% cell death compared with 47% of FTY720 treated cells and 50% of the milatuzumab-treated cells (P=0.0005 and P=0.0014, respectively) (FIG. 4C and FIG. 4D).

These data demonstrate that combination treatment with FTY720 and milatuzumab markedly enhances cell death in MCL cell lines and primary MCL tumor cells regardless of the histologic variant of MCL and the source of primary cells (PBMCs vs. lymph node). We were able to significantly decrease the doses of FTY720 and milatuzumab compared with the LC50 previously published without affecting induction of cell death when these two agents were used in combination.

In Vivo Therapeutic Activity of Combination Treatment with FTY720 and Milatuzumab.

We next evaluated the in vivo effect of FTY720 in combination with milatuzumab in a preclinical model of human MCL. After natural killer cell depletion with i.p. injection of anti mouse IL2Rβ antibody, six to eight-week old female SCID mice (cb17 scid/scid) were engrafted with $40 \times 10^6$ Jeko cells via tail vein injection. The primary end point of the study was overall survival defined as the time to develop symptoms, indicating lethal tumor burden after initiation of treatment. Mice (n=10/group) were treated starting at day 15 after engraftment. Twenty control mice received either placebo (saline) or trastuzumab (15 mg/kg) treatment. The third group was treated with FTY720 (5 mg/kg) every day for 2 weeks via i.p. The fourth group received milatuzumab (15 mg/kg) every three days, via i.p. injection. The fifth group received the combination of FTY720 and milatuzumab. FIG. 5 shows that the median survival for the combination treated group was 36 days (95% CI, 31-36), compared with 28 days for the saline treated mice (95% CI, 24-31), 27 days for the trastuzumab treated mice (95% CI, 23-29), 31 days for the FTY720 treated mice (95% CI, 28-32) and 33.5 days for the milatuzumab treated mice (95% CI, 23-34). The combination treatment significantly prolonged survival of this group compared with the control (P<0.0001), FTY720 (P=0.0001) and milatuzumab (P=0.0048) groups.

Discussion

MCL is a B-cell lymphoma characterized by a high degree of biologic derangements including genomic instability, major alterations in the cell cycle control and activation of key anti-apoptotic mechanisms (Perez-Galan et al., Blood 117: 26-38). For this reason, the natural history of MCL is a course of progressive relapses which are increasingly short-lived as the disease becomes more resistant to therapy (Id.). Therefore, the development of new therapeutic options targeting the complex pathobiology of MCL is crucial to improve outcomes for patients with this incurable disease.

FTY720, an immunosuppressive agent recently approved by FDA for the treatment of relapsed multiple sclerosis, has shown significant activity in several hematologic malignancies including MCL (Liu et al. 2010, Clin Cancer Res 16:3182-92; Levine & Yuan, 2005, J Clin Invest 115:2679-88; Reich et al, 2009, Immunol Lett 123:155-59; Yasui et al., 2005, Cancer Res 65:7478-84; Neviani et al., 2007, J Clin Invest 117:2408-21). We have recently demonstrated that FTY720 promotes death of MCL cells through caspase independent ROS generation and down-modulation of p-Akt and Cyclin D1, with subsequent accumulation of cells in the G0/G1 and G2/M phases of the cell cycle (Liu et al. 2010, Clin Cancer Res 16:3182-92). Here we further elucidated the mechanism of action of FTY720 and showed that FTY720 treatment of MCL cells induced features of autophagy blockage and lysosomal membrane permeabilization with subsequent translocation of lysosomal hydrolases in the cytosol, events that are all required for MCL cell death.

We also demonstrated that FTY720 treatment of MCL cells increases CD74 expression by preventing its degradation in the lysosomal compartment. We have recently shown that milatuzumab, a fully humanized mAb anti-CD74, has significant anti-MCL activity in vitro and in vivo and that milatuzumab-mediated cell death significantly correlated with antigen density (Alinari et al., 2011, Blood 117:4530-41). We combined these two agents and showed that this approach resulted in statistically significant enhanced cell death in vitro and significantly prolonged survival in a mouse model of human MCL. The in vitro and in vivo dosing schemes were chosen based on the data we previously published for the single agent approach and lead to drug concentrations that are achievable in patients (Liu et al. 2010, Clin Cancer Res 16:3182-92; Alinari et al., 2011, Blood 117:4530-41).

The FTY720 dose and schedule used in this study was determined based on a detailed in vivo pharmacokinetic (PK) study of STY720 in rats that was previously published (Liu et al., 2008, Blood 111:275-84; Suzuki et al., 1996, Transplant Proc 28:1375-76; Suzuki et al., 1996, Transplantation 61:200-05.) This rat PK study demonstrated that FTY720 achieved a 3.5 µM maximum plasma concentration at a 4 mg/kg single IV does. Therefore, a regimen of 5 mg/kg daily dose for 2 weeks is very likely to achieve a steady-state concentration. Because there are no published preclinical data on the PK and pharmacodynamics of milatuzumab, the in vitro and in vivo dosing schedule used in our study was based on reported studies in non-Hodgkin lymphoma and multiple myeloma (Stein et al., 2004, Blood 104:3705-11; Kaufman et al., 2009, J Clin Oncol 27 (15 suppl):8593.) A PK study performed in refractory/relapsed multiple myeloma patient treated with milatuzumab (1.5, 4, 8 or 16 mg/kg) twice weekly for 4 weeks showed that at the lowest human dose (1.5 mg/kg), the peak levels were 10-20 µg/mL, which is 2-4 times the in vitro concentration used in our studies. The dosing in our mice was at 1.2 mg/kg human equivalent dose, approximately the lowest dose used in the clinical study. In addition, both FTY720 and milatuzumab as single agents were used by our group in a Raji xenograph model and in the Jeko xenograph model (Liu et al., 2010, Clin Cancer Res 16:3182-92; Alinari et al., 2011, Blood 117:4530-41; Liu et al., 2008, Blood 111:275-84). This dosage and delivery schedule did not cause any observed weight loss or other significant side effects. Therefore, we adopted the same regimen, making our findings more clinically relevant.

Autophagy describes a physiologic mechanism thought to be involved in cancer cell survival as it provides an alternative source of energy during adverse conditions that may occur with exposure to cytotoxic agents (Liu et al., 2008, Blood 111:275-84; Levine, 2007, Nature 446:745-47). It has been shown that pharmacological inhibition of autophagy enhances the anti-lymphoma activity of multiple chemotherapeutic agents (Amaravadi et al., 2007, J Clin Invest 117:326-36). Here we showed that FTY720 can block the autophagic flux and to sensitize MCL cells to milatuzumab-mediated cell death.

It has been recently reported that FTY720 induces autophagy in prostate, ovarian and ALL tumor cells (Mizushima et al., 2008, Nature 451:1069-75; Levine & Yuan, 2005, J Clin Invest 115:2679-88; Boya et al., 2005, Mol Cell Biol 25:1025-40). In support of FTY720 as an inducer of autophagy, Zhang et al. (2010, Autophagy 6:1157-67), and Wallington-Beddoe et al. (2011, Autophagy 7:707-15), showed that FTY720 treatment resulted in significant increase of LC3-II levels, which were further augmented by co-treatment with bafilomycin A1, a vacuolar $H^+$-ATPase inhibitor that blocks autolysosome formation. Whereas we similarly showed that accumulation of LC3-II in FTY720 treated MCL cells was increased by the addition of chloroquine, we also showed that FTY720 and chloroquine treatment induced a similar accumulation of LC3-II in MCL cell treated with rapamycin, an autophagy inducer, suggesting a blockage of autophagic flux instead. Whereas all four cell lines showed accumulation of LC3-II after treatment, it is clear that FTY720 affects autophagy to various degrees in individual cell lines, which most likely reflects the biologic heterogeneity among the cell lines, a common feature of MCL. Furthermore, whereas Zhang et al. (2010, Autophagy 6:1157-67) reported increased level of Beclin-1 after FTY720 treatment of ovarian cancer cells, Wallington-Beddoe et al. (2011, Autophagy 7:707-15) reported that the levels of Beclin-1 remained unchanged after FTY720 treatment of ALL cells. The explanation was that FTY720 treatment decreased Mcl-1 levels, suggesting that the inhibitory control of Beclin-1 by this Bcl-2 family member was partially removed. Inhibition of Beclin-1 by anti-apoptotic Bcl-2 family members is known to inhibit autophagy (Kabeya et al., 2009, EMBO J 19:5720-28). However we not only showed that Beclin-1 levels remain unchanged after FTY720 treatment but also recently reported that FTY720 treatment does not affect Mcl-1/Bcl-2 levels in MCL (Liu et al. 2010, Clin Cancer Res 16:3182-92), suggesting once again an inhibitory effect of FTY720 on autophagic flux. Furthermore, whereas Wallington-Beddoe et al. (2011, Autophagy 7:707-15) did not evaluate p62 levels in FTY720 treated ALL cells, Zhang et al. (2010, Autophagy 6:1157-67) showed a significant decrease of p62 levels in FTY720 treated ovarian cancer cell. However, in agreement with our hypothesis that FTY720 blocks autophagic flux in MCL, we showed significant increase of p62 levels after FTY720 treatment in 2 of our MCL cell lines, which were further increased by the addition of chloroquine.

CD74 is a type II transmembrane glycoprotein that plays an important role as a survival receptor in the maturation/proliferation of B-cells and is degraded in the lysosomal compartment (Matza et al., 2001, J Biol Chem 276:27203-06; Starlets et al., 2006, Blood 107:4807-16; Stein et al., 2007, Clin Cancer Res 13:5556s-63s). Here we showed that CD74 expression levels were significantly increased by FTY720 treatment via blockade of CD74 lysosomal degradation and were further augmented by the addition of chloroquine, supporting our hypothesis that FTY720 functions as an autophagy blocker. The most clinically relevant aspect of these findings is that we have demonstrated that a potent anti-MCL agent (FTY720) also has the ability to modulate a druggable target (CD74) after blocking autophagy.

Based on our in vitro experiments and TEM images displaying MCL cells with enlarged autolysosomes with visible cytoplasmic structures enclosed after FTY720 treatment, we conclude that FTY720 most likely affects late stages of autophagosome maturation. FTY720 may have a dual effect on autophagic flux, an activation of upstream steps in autophagic flux characterized by accumulation of LC3, followed by a blockage of a late step of the pathway with inhibition of autophagic protein degradation.

Our study provides further insight into the FTY720 mediated mechanism of cell death. Studies have shown that the use of detergents such as sphingosine and lysosomotropic antibiotics such as ciprofloxacin can disrupt the integrity of the lysosomal membrane and induce cell death (Kagedal et al., 2001, Biochem J 359:335-43; Boya et al., 2003, J Exp Med 197:1323-34). Here we demonstrated that the lysosomal compartment and lysosomal membrane permeabilization play a critical role in FTY720-mediated cell death. Second we showed that lysosomal hydrolases (i.e. cathepsins) are key enzymes in caspase independent FTY720-mediated cell death. Third, we recently reported ROS generation as a consequence of FTY720 treatment in MCL, and our current data suggests that ROS generation is more likely because of lysosomal membrane permeabilization rather than mitochondrial membrane permeabilization. We have also recently shown that milatuzumab mediates MCL cell death through caspase independent ROS generation, mitochondrial membrane potential loss and disruption of the NF-kB pathway (Alinari et al., 2011, Blood 117:4530-41), providing a rationale for combining these two agents with independent mechanisms of action. Whereas FTY720 induces ROS generation through lysosomal membrane permeabilization, milatuzumab induces ROS generation as a consequence of its effect on the mitochondrial membrane. Furthermore we showed the milatuzumab response is correlated with CD74 density (Id.), making the combined approach with FTY720 and milatuzumab an ideal option for a disease with variability of CD74 expression (Id). Because of the ability of FTY720 to increase CD74 expression, providing more antigen to target, we were able to significantly decrease the dose of these two agents without affecting the synergistic effect on MCL cell viability, suggesting that lower dosages may be used in vivo resulting in a more favorable toxicity. The combination treatment induced significant enhanced cell death in all MCL cell lines and patient samples regardless of MCL subtype (classic versus blastic variant).

It has been recently shown that the phosphorylated form of FTY720 induces autophagy in prostate cancer cell lines through its interaction with S1P receptors (Boya et al., 2005, Mol Cell Biol 25:1025-40). Here we showed that, similar to FTY720, treatment of MCL cell lines with OSU-2S, a non-phosphorylatable FTY720 derivative recently developed at OSU, resulted in LC3-II accumulation, suggesting that interaction of FTY720 with SP1 receptors is not necessary for its effects on autophagy. Furthermore, FTY720 interaction with S1P receptors is responsible for its immunosuppressive effects, cardiovascular complications and macular edema (Cohen et al., 2010, N Engl J Med 362:402-415). Similar to FTY720, OSU-2S has significant cytotoxic activity in MCL cell lines and primary cells, suggesting that the S1P signaling is not necessary for FTY720-mediated cell death. Considering that OSU-2S has a safer toxicity profile compared to FTY720, this compound may provide anti-tumor activity without the S1P-mediated immune suppressive properties.

Finally, the intriguing results obtained with the in vitro experiments led us to investigate the combination of FTY720 and milatuzumab in a preclinical murine model of human MCL. This model was used as it represents the most aggressive and stringent preclinical model to evaluate potential experimental therapeutic strategies in MCL. The combination of FTY720 and milatuzumab significantly prolonged survival compared with untreated controls (P<0.0001) but also compared with the single agent approach with FTY720 (P=0.0001) and milatuzumab (P=0.0048).

In summary, FTY720 and milatuzumab combination therapy resulted in enhanced cell death in MCL cell lines and primary tumor samples regardless of MCL subtype. Furthermore, enhanced survival was observed with combination therapy in an in vivo murine model of MCL. The combination strategy of FTY720 (or OSU-2S) and milatuzumab could potentially represent an ideal approach for the treatment of MCL patients, maximizing the chances of remission while reducing treatment-associated toxicities.

Example 2

Expression of CD74 by AML Blasts and Cell Lines and Enhanced Cytotoxicity of Anti-CD74 Antibodies after IFN-γ Treatment CD74 (invariant chain, Ii) is a type-II transmembrane glycoprotein that associates with the major histocompatibility class (MHC) II α and β chains and directs the transport of the βαIi complexes to endosomes and lysosomes. The proinflammatory cytokine, macrophage migration-inhibitory factor (MIF), binds to cell surface CD74, initiating a signaling cascade involving activation of NF-κB. CD74 is expressed by certain normal HLA class II-positive cells, including B cells, monocytes, macrophages, Langerhans cells, dendritic cells, subsets of activated T cells, and thymic epithelium. CD74 is also expressed on a variety of malignant cells, including the vast majority of B-cell cancers (NHL, CLL, MM). Expression of CD74 has been observed by DNA microarray-based methodology in AML clinical samples, and it has been shown to be a prognostic factor in the cytogenetically normal subset of AML, and to be a predictive factor for response to bortezomib in combination with induction chemotherapy.

The LL1 monoclonal antibody was generated by hybridoma technology after immunization of BALB/c mice with Raji human Burkitt lymphoma cells. The LL1 antibody reacts with an epitope in the extracellular domain of CD74. CD74-positive cell lines have been shown to very rapidly internalize LL1 (nearly $10^7$ molecules per cell per day). This rapid internalization enables LL1 to be an extremely effective agent for delivery of cytotoxic agents, such as chemotherapeutics or toxins, to malignant target cells.

Humanized anti-CD74 LL1 antibody (milatuzumab) exhibits direct cytotoxicity for NHL, CLL and MM cell lines, and is in clinical evaluation for therapy of NHL, MM and CLL. CD74 is induced by interferons in multiple cancer cell lines. Here we report an evaluation of CD74 expression and function in AML, and the effect of CD74 upregulation by treatment with IFN-γ on the cytotoxicity of milatuzumab for AML cell lines.

CD74 expression in bone marrow biopsy (BMB) specimens from non-M3 AML patients was evaluated by immunohistochemistry and, for 3 human AML cell lines, by flow cytometry, with/without permeabilization and with/without IFN-γ (40 and 200 U/mL). These cell lines were also tested in proliferation assays for responses to milatuzumab, with/without IFN-γ. In 13/14 BMB specimens, there was moderate to strong CD74 expression by leukemic blasts, which was mostly intracellular, usually with a perinuclear distribution (data not shown). Three AML cell lines also showed moderate to strong expression of CD74, which was mostly intracellular (data not shown). Without IFN-γ, surface expression of CD74 was present, but IFN-γ treatment of these 3 lines resulted in upregulation of surface CD74 by 69-117% (not shown). Much higher levels of intracellular CD74 were observed in all 3 lines, with and without IFN-γ (not shown). IFN-γ induced intracellular CD74 in all 3 lines (from 85%-868%) (not shown). In ⅔ lines, IFN-γ increased milatuzumab-mediated growth inhibition (23.7 to 44.8% and −3.9 to 30.9%, respectively) (not shown).

CD74 is expressed in AML patient specimens and in AML cell lines, with the majority of CD74 expression found intracellularly. Cell surface and cytoplasmic expression of CD74 were upregulated in AML lines after IFN-γ exposure. This increased expression resulted in increased cytotoxicity of the anti-CD74 MAb, milatuzumab, in ⅔ AML lines. Thus, combined therapy with IFN-γ and milatuzumab treatment is of use for treatment of AML.

Example 3

Sensitivity of NHL to Killing by Anti-CD74 Antibodies is Increased by Interferon-γ

Milatuzumab is in clinical evaluation for therapy of NHL, multiple myeloma (MM), and CLL after preclinical evidence of activity in these tumor types. In addition to expression in hematologic cancers, CD74 is expressed on the surface of other types of tumor cells, including melanoma and renal cell carcinoma, and in the cytoplasm of others, including pancreatic and colonic carcinomas and glioblastomas (GBM).

We examined whether the ability of anti-CD74 MAbs to kill cancer cells can be increased by using IFN-γ as an inducer of antigen expression. Using a panel of diverse cancer cell lines (including NHL, MM, GBM, and pancreatic and colonic carcinomas), we examined IFN-γ-induced changes in surface and cytoplasmic CD74 expression. Sensitivity of the malignant cells to milatuzumab was assessed with and without IFN-γ by cytotoxicity assays.

Results

Expression of CD74, HLA-DR, and carcinoembryonic antigen (CEACAM5) was determined in untreated cells and cells exposed to 200 U of IFN-γ for 48 h by flow cytometry. Cells were stained with directly labeled MAbs in comparison to a directly labeled human IgG control. Antibodies were labeled using ALEXA FLUOR® 488 (Invitrogen, Carlsbad, Calif.). For determination of cytoplasmic antigen expression, cells were permeabilized prior to staining using the BD CYTOFIX/CYTOPERM™ kit (BD Biosciences, San Jose, Calif.).

Without IFN-γ, surface expression of HLA-DR and CD74 was present on 2/2 NHL, 2/2 mM, and only weakly positive on 2/2 GBM cell lines (Table 4). Surface CD74 and HLA-DR were weak or undetectable on 4/4 colon and 4/4 pancreatic carcinomas (Table 4). Cytoplasmic CD74 and HLA-DR were seen in the NHL, MM, GBM, and ¼ colon and ¼ pancreatic (CD74 only) carcinomas (Table 5).

TABLE 4

Cell Surface Expression of CD74, HLA-DR and CEACAM5 With and Without IFN-γ

|  | hIgG (control) | Labetuzumab (anti-CEA) | hL243γ4P (anti-HLA-DR) | Milatuzumab (anti-CD74) |
|---|---|---|---|---|
| Lymphomas | | | | |
| FSCCL | 2.3 | 2.6 | 1087.1 | 14.3 |
| FSCCL + IFNγ | 2.8 | 2.8 | 1610.9 | 19.0 |
| % change | 25.8 | 7.6 | 48.2 | 32.8 |
| RL | 4.0 | 2.4 | 749.5 | 20.2 |
| RL + IFNγ | 2.8 | 2.9 | 861.8 | 25.0 |
| % change | −29.4 | 17.3 | 15.0 | 23.8 |
| Multiple Myelomas | | | | |
| CAG | 5.2 | 5.0 | 1926.3 | 41.5 |
| CAG + IFNγ | 5.4 | 5.2 | 1813.9 | 39.2 |
| % change | 2.9 | 3.0 | −5.8 | −5.4 |
| KMS11 | 2.3 | 2.1 | 677.2 | 4.4 |
| KMS11 + IFNγ | 2.5 | 2.3 | 665.3 | 5.1 |
| % change | 5.2 | 7.1 | −1.8 | 14.0 |
| Pancreatic Cancers | | | | |
| Panc-1 | 4.3 | 4.1 | 4.3 | 4.5 |
| Panc-1 + IFNγ | 4.2 | 4.4 | 4.7 | 4.9 |
| % change | −2.3 | 6.3 | 9.2 | 9.4 |
| Capan-1 | 4.2 | 57.5 | 5.5 | 4.4 |
| Capan + IFNγ | 5.3 | 48.8 | 66.2 | 11.1 |
| % change | 26.6 | −15.1 | 1100.0 | 152.4 |
| Aspc-1 | 3.0 | 52.9 | 3.2 | 3.3 |
| Aspc-1 + IFNγ | 3.4 | 66.8 | 15.2 | 7.3 |
| % change | 13.9 | 26.3 | 373.5 | 121.3 |
| BxPC-3 | 2.4 | 5.6 | 2.3 | 2.6 |
| BxPC-3 + IFNγ | 3.7 | 7.0 | 43.8 | 6.2 |
| % change | 55.7 | 25.6 | 1771.4 | 142.2 |
| Colon Cancers | | | | |
| Lovo | 3.1 | 56.8 | 7.3 | 3.4 |
| Lovo + IFNγ | 4.4 | 84.4 | 276.3 | 9.2 |
| % change | 45.1 | 48.6 | 3705.1 | 173.7 |
| Moser | 3.9 | 63.8 | 4.0 | 4.1 |
| Moser + IFNγ | 4.0 | 77.2 | 8.5 | 4.8 |
| % change | 2.3 | 20.9 | 113.0 | 16.3 |
| HT29 | 3.3 | 11.1 | 3.3 | 3.4 |
| HT29 + IFNγ | 4.8 | 34.9 | 298.0 | 8.3 |
| % change | 45.5 | 213.5 | 8848.9 | 141.1 |
| LS174T | 4.8 | 61.1 | 5.3 | 5.9 |
| LS174T + IFNγ | 4.8 | 163.7 | 4.7 | 5.2 |
| % change | 0.0 | 167.9 | −11.7 | −11.3 |
| Glioblastomas | | | | |
| U87 | 3.3 | 3.7 | 41.9 | 5.4 |
| U87 + IFNγ | 3.3 | 4.5 | 171.5 | 9.5 |
| % change | −0.3 | 23.8 | 309.0 | 75.6 |
| U118 | 4.2 | 5.5 | 6.1 | 7.0 |
| U118 + IFNγ | 4.5 | 5.6 | 197.1 | 18.3 |
| % change | 7.2 | 2.4 | 3136.9 | 160.9 |
| TU118 | 4.72 | 4.68 | 5.08 | 7.17 |
| TU118 + IFNγ | 5.61 | 5.29 | 93.49 | 19.2 |
| % change | 18.9 | 13.0 | 1740.4 | 167.8 |

TABLE 5

Cytoplasmic Expression of CD74, HLA-DR and CEACAM5 With and Without IFN-γ

|  | hIgG (control) | Labetuzumab (anti-CEA) | hL243γ4P (anti-HLA-DR) | Milatuzumab (anti-CD74) |
|---|---|---|---|---|
| Lymphomas | | | | |
| FSCCL | 27.3 | 19.3 | 1466.8 | 708.0 |
| FSCCL + IFNγ | 45.3 | 38.8 | 2522.2 | 1122.0 |
| % change | 66.0 | 100.7 | 72.0 | 58.5 |
| RL | 13.4 | 7.8 | 1055.3 | 887.8 |
| RL + IFNγ | 16.4 | 10.8 | 1184.3 | 920.9 |
| % change | 22.6 | 37.9 | 12.2 | 3.7 |
| Multiple Myelomas | | | | |
| CAG | 10.0 | 7.1 | 2315.2 | 418.1 |
| CAG + IFNγ | 12.4 | 9.1 | 2422.9 | 501.0 |
| % change | 24.6 | 27.4 | 4.7 | 19.8 |
| KMS11 | 10.5 | 8.1 | 878.6 | 228.8 |
| KMS11 + IFNγ | 11.7 | 7.2 | 926.8 | 224.5 |
| % change | 12.0 | −11.4 | 5.5 | −1.9 |
| Pancreatic Cancers | | | | |
| Panc-1 | 22.8 | 20.3 | 22.7 | 24.4 |
| Panc-1 + IFNγ | 56.0 | 53.0 | 64.1 | 75.3 |
| % change | 146.0 | 161.2 | 181.9 | 208.7 |
| Capan-1 | 12.4 | 168.2 | 11.6 | 41.2 |
| Capan + IFNγ | 16.9 | 182.7 | 253.1 | 272.1 |
| % change | 36.0 | 8.7 | 2081.6 | 561.2 |
| Aspc-1 | 13.5 | 139.0 | 11.0 | 12.8 |
| Aspc-1 + IFNγ | 31.0 | 213.0 | 73.6 | 198.4 |
| % change | 130.0 | 53.2 | 571.9 | 1451.5 |
| BxPC-3 | 18.4 | 22.2 | 14.2 | 15.3 |
| BxPC-3 + IFNγ | 27.1 | 33.9 | 129.7 | 285.5 |
| % change | 47.0 | 52.7 | 811.0 | 1763.5 |
| Colon Cancers | | | | |
| Lovo | 22.0 | 127.2 | 32.5 | 39.7 |
| Lovo + IFNγ | 41.4 | 193.8 | 989.3 | 339.7 |
| % change | 88.2 | 52.4 | 2942.0 | 756.0 |
| Moser | 24.5 | 102.6 | 18.2 | 28.9 |
| Moser + IFNγ | 36.7 | 145.5 | 40.5 | 53.7 |
| % change | 49.5 | 41.8 | 122.1 | 86.1 |
| HT29 | 9.6 | 35.9 | 9.1 | 10.8 |
| HT29 + IFNγ | 22.9 | 80.0 | 638.1 | 202.0 |
| % change | 139.1 | 122.7 | 6919.8 | 1766.6 |
| LS174T | 29.4 | 154.4 | 23.4 | 34.6 |
| LS174T + IFNγ | 51.2 | 456.9 | 42.3 | 73.6 |
| % change | 74.2 | 195.9 | 81.0 | 112.7 |
| Glioblastomas | | | | |
| U87 | 5.4 | 11.9 | 102.4 | 54.9 |
| U87 + IFNγ | 5.5 | 21.3 | 429.0 | 141.9 |
| % change | 2.6 | 79.0 | 318.9 | 158.8 |
| U118 | 7.7 | 17.1 | 24.6 | 47.7 |
| U118 + IFNγ | 7.5 | 30.5 | 352.3 | 252.1 |
| % change | −2.5 | 78.2 | 1333.4 | 428.2 |
| TU118 | 35.11 | 20.4 | 23.61 | 121.92 |
| TU118 + IFNγ | 57.21 | 43.96 | 215.38 | 578.58 |
| % change | 62.9 | 115.5 | 812.2 | 374.6 |

Two-day incubation with IFN-γ increased surface and cytoplasmic expression of CD74 and HLA-DR (Table 4, Table 5). In all 4 colon cancer lines, IFN-γ increased cytoplasmic expression of both antigens, and surface expression of HLA-DR in ¾ and CD74 in ²⁄₄ (Table 4, Table 5). Upregulation of HLA-DR and CD74 ranged from 23-3700% (Table 4, Table 5).

The cytotoxicity of anti-CD74 antibodies was examined in the presence or absence of IFN-γ (not shown). As previously observed, in vitro cytotoxicity of milatuzumab required crosslinking (Stein, et al., Blood, 104: 3705-11, 2004). Goat anti-human IgG (GAH) was used for crosslinking in these experiments. Increased killing by milatuzumab (33%) was seen in vitro after IFN-γ exposure in WSU-FSCCL NHL cells (not shown). Cytotoxicity was in part due to apoptosis, as significant increases in annexin V binding (P=0.01) were observed after treatment with IFN-γ plus milatuzumab (not shown). Experiments addressing cell signaling suggest a role for AKT, since phosphorylated AKT levels increased (P=0.06) in response to IFN-γ+ milatuzumab (not shown). Milatuzumab was unable to kill Capan-1 (pancreatic carcinoma), Aspc-1 (pancreatic carcinoma), LoVo (colon carcinoma), HT-29 (colon carcinoma), U87 (GBM), or U118 (GBM) cells, regardless of the use of a crosslinking agent or IFN-γ induced upregulation of antigen expression.

CONCLUSIONS

Cell surface and cytoplasmic expression of CD74 was increased on cell lines from a variety of cancer types after IFN-γ exposure. In the follicular lymphoma cell line, WSU-FSCCL, the increased expression of these antigens correlates with increased toxicity milatuzumab. These studies demonstrate the potential benefit of combined IFN-γ and anti-CD74 antibody therapies.

It will be readily apparent to one skilled in the art that varying substitutions and modifications may be made to the invention disclosed herein without departing from the scope and spirit of the invention. Thus, such additional embodiments are within the scope of the present invention.

What is claimed is:

1. A method of killing a CD74-expressing cell comprising
a) exposing the cell to fingolimod; and
b) exposing the cell to an anti-CD74 antibody or antigen-binding fragment thereof.

2. The method of claim 1, wherein the cell is a diseased cell.

3. The method of claim 2, wherein the disease is selected from the group consisting of cancer, autoimmune disease and immune dysfunction disease.

4. The method of claim 3, wherein the cancer is selected from the group consisting of hematopoietic cancer, B-cell leukemia, B-cell lymphoma, non-Hodgkin's lymphoma (NHL), multiple myeloma, chronic lymphocytic leukemia, acute lymphocytic leukemia, acute myelogenous leukemia, glioblastoma, follicular lymphoma, diffuse large B cell lymphoma, colon cancer, pancreatic cancer, renal cancer, lung cancer, stomach cancer, breast cancer, prostate cancer, ovarian cancer and melanoma.

5. The method of claim 3, wherein the immune dysregulation disease is graft-versus-host disease or organ transplant rejection.

6. The method of claim 3, wherein the autoimmune disease is selected from the group consisting of acute idiopathic thrombocytopenic purpura, chronic idiopathic thrombocytopenic purpura, dermatomyositis, Sydenham's chorea, myasthenia gravis, systemic lupus erythematosus, lupus nephritis, rheumatic fever, polyglandular syndromes, bullous pemphigoid, diabetes mellitus, Henoch-Schonlein purpura, post-streptococcal nephritis, erythema nodosum, Takayasu's arteritis, Addison's disease, rheumatoid arthritis, multiple sclerosis, sarcoidosis, ulcerative colitis, erythema multiforme, IgA nephropathy, polyarteritis nodosa, ankylosing spondylitis, Goodpasture's syndrome, thromboangitis obliterans, Sjogren's syndrome, primary biliary cirrhosis, Hashimoto's thyroiditis, thyrotoxicosis, scleroderma, chronic active hepatitis, polymyositis/dermatomyositis, polychondritis, pemphigus vulgaris, Wegener's granulomatosis, membranous nephropathy, amyotrophic lateral sclerosis, tabes dorsalis, giant cell arteritis/polymyalgia, pernicious anemia, rapidly progressive glomerulonephritis, psoriasis and fibrosing alveolitis.

7. The method of claim 1, wherein the fingolimod is administered before or concurrently with the anti-CD74 antibody.

8. The method of claim 1, wherein the anti-CD74 antibody competes for binding to CD74 with, or binds to the same epitope of CD74 as, an antibody comprising the light chain complementarity-determining region (CDR) sequences CDR1 (RSSQSLVHRNGNTYLH; SEQ ID NO:1), CDR2 (TVSNRFS; SEQ ID NO:2), and CDR3 (SQSSHVPPT; SEQ ID NO:3) and the heavy chain variable region CDR sequences CDR1 (NYGVN; SEQ ID NO:4), CDR2 (WINPNTGEPTFDDDFKG; SEQ ID NO:5), and CDR3 (SRGKNEAWFAY; SEQ ID NO:6).

9. The method of claim 1, wherein the anti-CD74 antibody comprises the light chain CDR sequences CDR1 (RSSQSLVHRNGNTYLH; SEQ ID NO:1), CDR2 (TVSNRFS; SEQ ID NO:2), and CDR3 (SQSSHVPPT; SEQ ID NO:3) and the heavy chain variable region CDR sequences CDR1 (NYGVN; SEQ ID NO:4), CDR2 (WINPNTGEPTFDDDFKG; SEQ ID NO:5), and CDR3 (SRGKNEAWFAY; SEQ ID NO:6).

10. The method of claim 1, wherein the anti-CD74 antibody or fragment thereof is a naked antibody or fragment thereof.

11. The method of claim 10, further comprising exposing the cell to at least one therapeutic agent selected from the group consisting of a radionuclide, a cytotoxin, a chemotherapeutic agent, a drug, a pro-drug, a toxin, an enzyme, an immunomodulator, an anti-angiogenic agent, a pro-apoptotic agent, a cytokine, a hormone, an oligonucleotide, an antisense molecule, a siRNA, a second antibody and a second antibody fragment.

12. The method of claim 1, wherein the anti-CD74 antibody or fragment thereof is conjugated to at least one therapeutic agent selected from the group consisting of a radionuclide, a cytotoxin, a chemotherapeutic agent, a drug, a pro-drug, a toxin, an enzyme, an immunomodulator, an anti-angiogenic agent, a pro-apoptotic agent, a cytokine, a hormone, an oligonucleotide, an antisense molecule, a siRNA, a second antibody and a second antibody fragment.

13. The method of claim 12, wherein the anti-CD74 antibody or fragment thereof is conjugated to a second antibody or fragment thereof to form a bispecific antibody.

14. The method of claim 13, wherein the second antibody or fragment thereof binds to an antigen selected from the group consisting of carbonic anhydrase IX, CCCL19, CCCL21, CSAp, CD1, CD1a, CD2, CD3, CD4, CD5, CD8, CD11A, CD14, CD15, CD16, CD18, CD19, IGF-1R, CD20, CD21, CD22, CD23, CD25, CD29, CD30, CD32b, CD33, CD37, CD38, CD40, CD40L, CD45, CD46, CD52, CD54, CD55, CD59, CD64, CD66a-e, CD67, CD70, CD74, CD79a, CD80, CD83, CD95, CD126, CD133, CD138, CD147, CD154, CXCR4, CXCR7, CXCL12, HIF-1α, AFP, PSMA, CEACAM5, CEACAM6, B7, ED-B of fibronectin, Factor H, FHL-1, Flt-3, folate receptor, GROB, HMGB-1, hypoxia inducible factor (HIF), HM1.24, insulin-like growth factor-1 (IGF-1), IFN-γ, IFN-α, IFN-β, IL-2, IL-4R, IL-6R, IL-13R, IL-15R, IL-17R, IL-18R, IL-6, IL-8, IL-12, IL-15, IL-17, IL-18, IL-25, PP-10, MAGE, mCRP, MCP-1, MPP-1A, MIP-1B, MIF, MUC1, MUC2, MUC3, MUC4, MUC5, NCA-95, NCA-90, Ia, HM1.24, EGP-1, EGP-2, HLA-DR, tenascin, Le(y), RANTES, T101, TAC, Tn antigen, Thomson-Friedenreich antigens, tumor necrosis antigens, TNF-α, TRAIL receptor (R1 and R2), VEGFR, EGFR, PlGF, complement factors C3, C3a, C3b, C5a, C5, and an oncogene product.

15. The method of claim 13, wherein the bispecific antibody is a dock-and-lock complex.

16. The method of claim 12, wherein the therapeutic agent is selected from the group consisting of aplidin, azaribine, anastrozole, azacytidine, bleomycin, bortezomib, bryostatin-1, busulfan, calicheamycin, camptothecin, 10-hydroxycamptothecin, carmustine, celebrex, chlorambucil, cisplatin, irinotecan (CPT-11), SN-38, carboplatin, cladribine, cyclophosphamide, cytarabine, dacarbazine, docetaxel, dactinomycin, daunomycin glucuronide, daunorubicin, dexamethasone, diethylstilbestrol, doxorubicin, doxorubicin glucuronide, epirubicin glucuronide, ethinyl estradiol, estramustine, etoposide, etoposide glucuronide, etoposide phosphate, floxuridine (FUdR), 3',5'-O-dioleoyl-FUdR (FUdR-dO), fludarabine, flutamide, fluorouracil, fluoxymesterone, gemcitabine, hydroxyprogesterone caproate, hydroxyurea, idarubicin, ifosfamide, L-asparaginase, leucovorin, lomustine, mechlorethamine, medroprogesterone acetate, megestrol acetate, melphalan, mercaptopurine, 6-mercaptopurine, methotrexate, mitoxantrone, mithramycin, mitomycin, mitotane, phenyl butyrate, prednisone, procarbazine, paclitaxel, pentostatin, PSI-341, semustine streptozocin, tamoxifen, taxanes, taxol, testosterone propionate, thalidomide, thioguanine, thiotepa, teniposide, topotecan, uracil mustard, velcade, vinblastine, vinorelbine, vincristine, ricin, abrin, ribonuclease, onconase, rapLR1, DNase I, Staphylococcal enterotoxin-A, pokeweed antiviral protein, gelonin, diphtheria toxin, Pseudomonas exotoxin, and Pseudomonas endotoxin.

17. The method of claim 13, wherein the therapeutic agent is a radionuclide selected from the group consisting of $^{103m}Rh$, to $^{103}Rh$, $^{105}Rh$, $^{105}Ru$, to $^{107}Hg$, to $^{109}Pd$, $^{109}Pt$, $^{111}Ag$, $^{111}In$, $^{113m}In$, $^{119}Sb$, $^{11}C$, $^{121m}Te$, $^{122m}Te$, $^{125}I$, $^{125m}Te$, $^{126}I$, $^{131}I$, $^{133}I$, $^{13}N$, $^{142}Pr$, $^{143}Pr$, $^{149}Pm$, $^{152}Dy$, $^{153}Sm$, $^{15}O$, $^{161}Ho$, $^{161}Tb$, $^{165}Tm$, $^{166}Dy$, $^{166}Ho$, $^{167}Tm$, $^{168}Tm$, $^{169}Er$, $^{169}Yb$, $^{177}Lu$, $^{186}Re$, $^{189m}Os$, $^{188}Re$, $^{189}Re$, $^{192}Ir$, $^{194}Ir$, $^{197}Pt$, $^{198}Au$, $^{199}Au$, $^{201}Tl$, $^{203}Hg$, $^{211}At$, $^{211}Bi$, $^{211}Pb$, $^{212}Bi$, $^{212}Pb$, $^{213}Bi$, $^{215}Po$, $^{217}At$, $^{219}Rn$, $^{221}Fr$, $^{223}Ra$, $^{224}Ac$, $^{225}Ac$, $^{225}Fm$, $^{32}P$, $^{33}P$, $^{47}Sc$, $^{51}Cr$, $^{57}Co$, $^{58}Co$, $^{59}Fe$, $^{62}Cu$, $^{67}Cu$, $^{67}Ga$, $^{75}Br$, $^{75}Se$, $^{76}Br$, $^{77}As$, $^{77}Br$, $^{80m}Br$, $^{89}Sr$, $^{90}Y$, $^{95}Ru$, $^{97}Ru$, $^{99}Mo$ and $^{99m}Tc$.

18. The method of claim 12, wherein the therapeutic agent is an enzyme selected from the group consisting of malate dehydrogenase, staphylococcal nuclease, delta-V-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase.

19. The method of claim 12, wherein the therapeutic agent is an immunomodulator selected from the group consisting of erythropoietin, thrombopoietin tumor necrosis factor-α (TNF), TNF-β, granulocyte-colony stimulating factor (G-CSF), granulocyte macrophage-colony stimulating factor (GM-CSF), interferon-α, interferon-β, interferon-γ, stem cell growth factor designated "S1 factor", human growth hormone, N-methionyl human growth hormone, bovine growth hormone, parathyroid hormone, thyroxine, insulin, proinsulin, relaxin, prorelaxin, follicle stimulating hormone (FSH), thyroid stimulating hormone (TSH), luteinizing hormone (LH), hepatic growth factor, prostaglandin, fibroblast growth factor, prolactin, placental lactogen, OB protein, mullerian-inhibiting substance, mouse gonadotropin-associated peptide, inhibin, activin, vascular endothelial growth factor, integrin, NGF-β, platelet-growth factor, TGF-α, TGF-β, insulin-like growth factor-I, insulin-like growth factor-II, macrophage-CSF (M-CSF), IL-1, IL-1α, IL-2, IL-3, IL-4, IL-5, IL-6, IL-7, IL-8, IL-9, IL-10, IL-11, IL-12, IL-13, IL-14, IL-15, IL-16, IL-17, IL-18, IL-21, IL-25, LIF, FLT-3, angiostatin, thrombospondin, endostatin and LT.

20. The method of claim 1, wherein the CD74-expressing cell is killed by the combination of fingolimod and anti-CD74 antibody, but not by anti-CD74 antibody alone.

21. The method of claim 1 wherein exposure of the cell to fingolimod increases the expression of CD74 by the cell.

22. The method of claim 1, wherein the antibody fragment is selected from the group consisting of F(ab')$_2$, F(ab)$_2$, Fab', Fab, Fv, scFv and single domain antibody.

23. The method of claim 1, wherein the anti-CD74 antibody is a chimeric, humanized or human anti-CD74 antibody.

24. The method of claim 1, further comprising exposing the cell to interferon-γ.

25. The method of claim 1, further comprising exposing the cell to an anti-HLA-DR antibody or antigen-binding fragment thereof.

26. The method of claim 25, wherein the anti-HLA-DR antibody competes for binding to HLA-DR with, or binds to the same epitope of HLA-DR as, an antibody comprising the heavy chain CDR sequences CDR1 (NYGMN, SEQ ID NO:7), CDR2 (WINTYTREPTYADDFKG, SEQ ID NO:8), and CDR3 (DITAVVPTGFDY, SEQ ID NO:9) and the light chain CDR sequences CDR1 (RASENIYSNLA, SEQ ID NO:10), CDR2 (AASNLAD, SEQ ID NO:11), and CDR3 (QHFWTTPWA, SEQ ID NO:12).

27. The method of claim 25, wherein the anti-HLA-DR antibody comprises heavy chain CDR sequences CDR1 (NYGMN, SEQ ID NO:7), CDR2 (WINTYTREPTYADDFKG, SEQ ID NO:8), and CDR3 (DITAVVPTGFDY, SEQ ID NO:9) and the light chain CDR sequences CDR1 (RASENIYSNLA, SEQ ID NO:10), CDR2 (AASNLAD, SEQ ID NO:11), and CDR3 (QHFWTTPWA, SEQ ID NO:12).

28. The method of claim 25, wherein the anti-HLA-DR antibody or fragment thereof is a naked antibody or fragment thereof.

29. The method of claim 25, wherein the anti-HLA-DR antibody or fragment thereof is conjugated to at least one therapeutic agent selected from the group consisting of a radionuclide, a cytotoxin, a chemotherapeutic agent, a drug, a pro-drug, a toxin, an enzyme, an immunomodulator, an anti-angiogenic agent, a pro-apoptotic agent, a cytokine, a hormone, an oligonucleotide, an antisense molecule, a siRNA, a second antibody and a second antibody fragment.

30. A method of treating a disease selected from the group consisting of cancer, autoimmune disease and immune dysfunction disease comprising:
   a) administering fingolimod to an individual suspected of having the disease; and
   b) administering to the individual an anti-CD74 antibody or antigen-binding fragment thereof.

31. The method of claim 30, wherein the cancer is selected from the group consisting of hematopoietic cancer, B-cell leukemia, B-cell lymphoma, non-Hodgkin's lymphoma (NHL), multiple myeloma, chronic lymphocytic leukemia, acute lymphocytic leukemia, acute myelogenous leukemia, glioblastoma, follicular lymphoma, diffuse large B cell lymphoma, colon cancer, pancreatic cancer, renal cancer, lung cancer, stomach cancer, breast cancer, prostate cancer, ovarian cancer and melanoma.

32. The method of claim 30, wherein the immune dysregulation disease is graft-versus-host disease or organ transplant rejection.

33. The method of claim 30, wherein the autoimmune disease is selected from the group consisting of acute idiopathic thrombocytopenic purpura, chronic idiopathic thrombocytopenic purpura, dermatomyositis, Sydenham's chorea, myasthenia gravis, systemic lupus erythematosus, lupus nephritis, rheumatic fever, polyglandular syndromes, bullous pemphigoid, diabetes mellitus, Henoch-Schonlein purpura, post-streptococcal nephritis, erythema nodosum, Takayasu's arteritis, Addison's disease, rheumatoid arthritis, multiple sclerosis, sarcoidosis, ulcerative colitis, erythema multiforme, IgA nephropathy, polyarteritis nodosa, ankylosing spondylitis, Goodpasture's syndrome, thromboangitis obliterans, Sjogren's syndrome, primary biliary cirrhosis, Hashimoto's thyroiditis, thyrotoxicosis, scleroderma, chronic active hepatitis, polymyositis/dermatomyositis, polychondritis, pemphigus vulgaris, Wegener's granulomatosis, membranous nephropathy, amyotrophic lateral sclerosis, tabes dorsalis, giant cell arteritis/polymyalgia, pernicious anemia, rapidly progressive glomerulonephritis, psoriasis and fibrosing alveolitis.

34. The method of claim 30, wherein the fingolimod is administered before or concurrently with the antibody or fragment thereof.

35. The method of claim 30, wherein the antibody or fragment thereof is a naked antibody or fragment thereof.

36. The method of claim 35, further comprising administering at least one therapeutic agent selected from the group consisting of a radionuclide, a cytotoxin, a chemotherapeutic agent, a drug, a pro-drug, a toxin, an enzyme, an immunomodulator, an anti-angiogenic agent, a pro-apoptotic agent, a cytokine, a hormone, an oligonucleotide, an antisense molecule, a siRNA, a second antibody and a second antibody fragment.

37. The method of claim 36, further comprising administering both an anti-CD74 and an anti-HLA-DR antibody or fragment thereof.

38. The method of claim 30, wherein the antibody or fragment thereof is conjugated to at least one therapeutic agent selected from the group consisting of a radionuclide, a cytotoxin, a chemotherapeutic agent, a drug, a pro-drug, a toxin, an enzyme, an immunomodulator, an anti-angiogenic agent, a pro-apoptotic agent, a cytokine, a hormone, an oligonucleotide, an antisense molecule, a siRNA, a second antibody and a second antibody fragment.

39. The method of claim 38, wherein the therapeutic agent is selected from the group consisting of aplidin, azaribine, anastrozole, azacytidine, bleomycin, bortezomib, bryostatin-1, busulfan, calicheamycin, camptothecin, 10-hydroxycamptothecin, carmustine, celebrex, chlorambucil, cisplatin, irinotecan (CPT-11), SN-38, carboplatin, cladribine, cyclophosphamide, cytarabine, dacarbazine, docetaxel, dactinomycin, daunomycin glucuronide, daunorubicin, dexamethasone, diethylstilbestrol, doxorubicin, doxorubicin glucuronide, epirubicin glucuronide, ethinyl estradiol, estramustine, etoposide, etoposide glucuronide, etoposide phosphate, floxuridine (FUdR), 3',5'-O-dioleoyl-FudR (FUdR-dO), fludarabine, flutamide, fluorouracil, fluoxymesterone, gemcitabine, hydroxyprogesterone caproate, hydroxyurea, idarubicin, ifosfamide, L-asparaginase, leucovorin, lomustine, mechlorethamine, medroprogesterone acetate, megestrol acetate, melphalan, mercaptopurine, 6-mercaptopurine, methotrexate, mitoxantrone, mithramycin, mitomycin, mitotane, phenyl butyrate, prednisone, procarbazine, paclitaxel, pentostatin, PSI-341, semustine streptozocin, tamoxifen, taxanes, taxol, testosterone propionate, thalidomide, thioguanine, thiotepa, teniposide, topotecan, uracil mustard, velcade, vinblastine, vinorelbine, vincristine, ricin, abrin, ribonuclease, onconase, rapLR1, DNase I, Staphylococcal enterotoxin-A, pokeweed antiviral protein, gelonin, diphtheria toxin, Pseudomonas exotoxin, and Pseudomonas endotoxin.

40. The method of claim 38, wherein the therapeutic agent is a radionuclide selected from the group consisting of $^{103m}$Rh, $^{103}$Ru, $^{\Psi}$Rh, $^{105}$Ru, $^{107}$Hg, $^{109}$Pd, $^{109}$Pt, $^{111}$Ag, $^{111}$In, $^{113m}$In, $^{119}$Sb, $^{11}$C, $^{121m}$Te, $^{122m}$Te, $^{125}$I, $^{125m}$Te, $^{126}$I, $^{131}$I, $^{133}$I, $^{13}$N, $^{142}$Pr, $^{143}$Pr, $^{149}$Pm, $^{152}$Dy, $^{153}$Sm, $^{15}$O, $^{161}$Ho, $^{161}$Tb, $^{165}$Tm, $^{166}$Dy, $^{166}$Ho, $^{167}$Tm, $^{168}$Tm, $^{169}$Er, $^{169}$Yb, $^{177}$Lu, $^{186}$Re, $^{188}$Re, $^{189m}$Os, $^{189}$Re, $^{192}$Ir, $^{194}$Ir, $^{197}$Pt, $^{198}$Au, $^{199}$Au, $^{201}$Tl, $^{203}$Hg, $^{211}$At, $^{211}$Bi, $^{211}$Pb, $^{212}$Bi, $^{212}$Pb, $^{213}$Bi, $^{215}$Po, $^{217}$At, $^{219}$Rn, $^{221}$Fr, $^{223}$Ra, $^{224}$Ac, $^{225}$Ac, $^{225}$Fm, $^{32}$P, $^{33}$P, $^{47}$Sc, $^{51}$Cr, $^{57}$Co, $^{58}$Co, $^{59}$Fe, $^{62}$Cu, $^{67}$Cu, $^{67}$Ga, $^{75}$Br, $^{75}$Se, $^{76}$Br, $^{77}$As, $^{77}$Br, $^{80m}$Br, $^{89}$Sr, $^{90}$Y, $^{95}$Ru, $^{97}$Ru, $^{99}$Mo and $^{99m}$Tc.

41. The method of claim 38, wherein the therapeutic agent is an enzyme selected from the group consisting of malate dehydrogenase, staphylococcal nuclease, delta-V-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase.

42. The method of claim 38, wherein the therapeutic agent is an immunomodulator selected from the group consisting of erythropoietin, thrombopoietin tumor necrosis factor-α (TNF), TNF-β, granulocyte-colony stimulating factor (G-CSF), granulocyte macrophage-colony stimulating factor (GM-CSF), interferon-α, interferon-β, interferon-γ, stem cell growth factor designated "S1 factor", human growth hormone, N-methionyl human growth hormone, bovine growth hormone, parathyroid hormone, thyroxine, insulin, proinsulin, relaxin, prorelaxin, follicle stimulating hormone (FSH), thyroid stimulating hormone (TSH), luteinizing hormone (LH), hepatic growth factor, prostaglandin, fibroblast growth factor, prolactin, placental lactogen, OB protein, mullerian-inhibiting substance, mouse gonadotropin-associated peptide, inhibin, activin, vascular endothelial growth factor, integrin, NGF-β, platelet-growth factor, TGF-α, TGF-β, insulin-like growth factor-I, insulin-like growth factor-II, macrophage-CSF (M-CSF), IL-1, IL-1α, IL-2, IL-3, IL-4, IL-5, IL-6, IL-7, IL-8, IL-9, IL-10, IL-11, IL-12, IL-13, IL-14, IL-15, IL-16, IL-17, IL-18, IL-21, IL-25, LIF, FLT-3, angiostatin, thrombospondin, endostatin and LT.

43. The method of claim 30, wherein the antibody fragment is selected from the group consisting of F(ab')$_2$, F(ab)$_2$, Fab', Fab, Fv, scFv and single domain antibody.

44. The method of claim 30, wherein the antibody is a chimeric, humanized or human antibody.

45. A therapeutic composition comprising:
  a) fingolimod; and
  b) an anti-CD74 antibody or antigen-binding fragment thereof.

46. The composition of claim 45, wherein the antibody or fragment thereof is a naked antibody or fragment thereof.

47. The composition of claim 45 wherein the antibody or fragment thereof is conjugated to at least one therapeutic agent.

48. The composition of claim 46, further comprising at least one therapeutic agent.

* * * * *

SEQUENCE LISTING

```
<160> NUMBER OF SEQ ID NOS: 60

<210> SEQ ID NO 1
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Arg Ser Ser Gln Ser Leu Val His Arg Asn Gly Asn Thr Tyr Leu His
1               5                   10                  15

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Thr Val Ser Asn Arg Phe Ser
1               5

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ser Gln Ser Ser His Val Pro Pro Thr
1               5

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Asn Tyr Gly Val Asn
1               5

<210> SEQ ID NO 5
```

```
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Trp Ile Asn Pro Asn Thr Gly Glu Pro Thr Phe Asp Asp Asp Phe Lys
1               5                   10                  15

Gly

<210> SEQ ID NO 6
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ser Arg Gly Lys Asn Glu Ala Trp Phe Ala Tyr
1               5                   10

<210> SEQ ID NO 7
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Gly Gly Gly Gly Ser Gly Gly Gly Gly Ser Gly Gly Gly Gly Ser
1               5                   10                  15

<210> SEQ ID NO 8
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Ser His Ile Gln Ile Pro Pro Gly Leu Thr Glu Leu Leu Gln Gly Tyr
1               5                   10                  15

Thr Val Glu Val Leu Arg Gln Gln Pro Pro Asp Leu Val Glu Phe Ala
                20                  25                  30

Val Glu Tyr Phe Thr Arg Leu Arg Glu Ala Arg Ala
            35                  40

<210> SEQ ID NO 9
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Cys Gly His Ile Gln Ile Pro Pro Gly Leu Thr Glu Leu Leu Gln Gly
1               5                   10                  15

Tyr Thr Val Glu Val Leu Arg Gln Gln Pro Pro Asp Leu Val Glu Phe
                20                  25                  30

Ala Val Glu Tyr Phe Thr Arg Leu Arg Glu Ala Arg Ala
```

```
<210> SEQ ID NO 10
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gln Ile Glu Tyr Leu Ala Lys Gln Ile Val Asp Asn Ala Ile Gln Gln
1               5                   10                  15

Ala

<210> SEQ ID NO 11
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Cys Gly Gln Ile Glu Tyr Leu Ala Lys Gln Ile Val Asp Asn Ala Ile
1               5                   10                  15

Gln Gln Ala Gly Cys
            20

<210> SEQ ID NO 12
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Ser Leu Arg Glu Cys Glu Leu Tyr Val Gln Lys His Asn Ile Gln Ala
1               5                   10                  15

Leu Leu Lys Asp Ser Ile Val Gln Leu Cys Thr Ala Arg Pro Glu Arg
            20                  25                  30

Pro Met Ala Phe Leu Arg Glu Tyr Phe Glu Arg Leu Glu Lys Glu Glu
        35                  40                  45

Ala Lys
    50

<210> SEQ ID NO 13
<211> LENGTH: 55
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Met Ser Cys Gly Gly Ser Leu Arg Glu Cys Glu Leu Tyr Val Gln Lys
1               5                   10                  15

His Asn Ile Gln Ala Leu Leu Lys Asp Ser Ile Val Gln Leu Cys Thr
            20                  25                  30

Ala Arg Pro Glu Arg Pro Met Ala Phe Leu Arg Glu Tyr Phe Glu Arg
        35                  40                  45

Leu Glu Lys Glu Glu Ala Lys
    50                  55
```

<210> SEQ ID NO 14
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Cys Gly Phe Glu Glu Leu Ala Trp Lys Ile Ala Lys Met Ile Trp Ser
1               5                   10                  15

Asp Val Phe Gln Gln Gly Cys
            20

<210> SEQ ID NO 15
<211> LENGTH: 51
<212> TYPE: PRT
<213> ORGANISM: Homo sapiens

<400> SEQUENCE: 15

Ser Leu Arg Glu Cys Glu Leu Tyr Val Gln Lys His Asn Ile Gln Ala
1               5                   10                  15

Leu Leu Lys Asp Val Ser Ile Val Gln Leu Cys Thr Ala Arg Pro Glu
            20                  25                  30

Arg Pro Met Ala Phe Leu Arg Glu Tyr Phe Glu Lys Leu Glu Lys Glu
        35                  40                  45

Glu Ala Lys
    50

<210> SEQ ID NO 16
<211> LENGTH: 54
<212> TYPE: PRT
<213> ORGANISM: Homo sapiens

<400> SEQUENCE: 16

Ser Leu Lys Gly Cys Glu Leu Tyr Val Gln Leu His Gly Ile Gln Gln
1               5                   10                  15

Val Leu Lys Asp Cys Ile Val His Leu Cys Ile Ser Lys Pro Glu Arg
            20                  25                  30

Pro Met Lys Phe Leu Arg Glu His Phe Glu Lys Leu Glu Lys Glu Glu
        35                  40                  45

Asn Arg Gln Ile Leu Ala
    50

<210> SEQ ID NO 17
<211> LENGTH: 44
<212> TYPE: PRT
<213> ORGANISM: Homo sapiens

<400> SEQUENCE: 17

Ser His Ile Gln Ile Pro Pro Gly Leu Thr Glu Leu Leu Gln Gly Tyr
1               5                   10                  15

Thr Val Glu Val Gly Gln Gln Pro Pro Asp Leu Val Asp Phe Ala Val
            20                  25                  30

Glu Tyr Phe Thr Arg Leu Arg Glu Ala Arg Arg Gln
        35                  40

<210> SEQ ID NO 18
<211> LENGTH: 44
<212> TYPE: PRT
<213> ORGANISM: Homo sapiens -continued

<400> SEQUENCE: 18

Ser Ile Glu Ile Pro Ala Gly Leu Thr Glu Leu Leu Gln Gly Phe Thr
1               5                   10                  15

Val Glu Val Leu Arg His Gln Pro Ala Asp Leu Leu Glu Phe Ala Leu
            20                  25                  30

Gln His Phe Thr Arg Leu Gln Gln Glu Asn Glu Arg
        35                  40

<210> SEQ ID NO 19
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Gln Ile Glu Tyr Val Ala Lys Gln Ile Val Asp Tyr Ala Ile His Gln
1               5                   10                  15

Ala

<210> SEQ ID NO 20
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Gln Ile Glu Tyr Lys Ala Lys Gln Ile Val Asp His Ala Ile His Gln
1               5                   10                  15

Ala

<210> SEQ ID NO 21
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Gln Ile Glu Tyr His Ala Lys Gln Ile Val Asp His Ala Ile His Gln
1               5                   10                  15

Ala

<210> SEQ ID NO 22
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Gln Ile Glu Tyr Val Ala Lys Gln Ile Val Asp His Ala Ile His Gln
1               5                   10                  15

Ala

<210> SEQ ID NO 23
<211> LENGTH: 21
<212> TYPE: DNA

```
<213> ORGANISM: Artificial Sequence
<220> FEATURE:
<223> OTHER INFORMATION: Description of Artificial Sequence: Synthetic
      oligonucleotide

<400> SEQUENCE: 23
aatgcggcgg tggtgacagt a                                                   21

<210> SEQ ID NO 24
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
aagctcagca cacagaaaga c                                                   21

<210> SEQ ID NO 25
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 25
uaaaaucuuc cugcccacct t                                                   21

<210> SEQ ID NO 26
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 26
ggaagcuguu ggcugaaaat t                                                   21

<210> SEQ ID NO 27
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 27
aagaccagcc ucuuugccca g                                                   21

<210> SEQ ID NO 28
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
ggaccaggca gaaaacgag                                                      19
```

```
<210> SEQ ID NO 29
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 29
cuaucaggau gacgcgg                                                       17

<210> SEQ ID NO 30
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 30
ugacacaggc aggcuugacu u                                                  21

<210> SEQ ID NO 31
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
ggtgaagaag ggcgtccaa                                                     19

<210> SEQ ID NO 32
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
gatccgttgg agctgttggc gtagttcaag agactcgcca acagctccaa cttttggaaa        60

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
aggtggtgtt aacagcagag                                                    20

<210> SEQ ID NO 34
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
aaggtggagc aagcggtgga g                                                  21

<210> SEQ ID NO 35
```

```
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
aaggagttga aggccgacaa a                                              21

<210> SEQ ID NO 36
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 36
uauggagcug cagaggaugt t                                              21

<210> SEQ ID NO 37
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
tttgaatatc tgtgctgaga acacagttct cagcacagat attctttt                 49

<210> SEQ ID NO 38
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
aatgagaaaa gcaaaaggtg ccctgtctc                                      29

<210> SEQ ID NO 39
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 39
aaucaucauc aagaaagggc a                                              21

<210> SEQ ID NO 40
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 40
```
augacuguca ggauguugct t                                              21

<210> SEQ ID NO 41
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 41
gaacgaaucc ugaagacauc u                                              21

<210> SEQ ID NO 42
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
aagcctggct acagcaatat gcctgtctc                                      29

<210> SEQ ID NO 43
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 43
ugaccaucac cgaguuuaut t                                              21

<210> SEQ ID NO 44
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
aagtcggacg caacagagaa a                                              21

<210> SEQ ID NO 45
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 45
cuaccuuucu acggacgugt t                                              21

<210> SEQ ID NO 46
<211> LENGTH: 21
<212> TYPE: DNA
<213> ORGANISM: Artificial Sequence
<220> FEATURE:
<223> OTHER INFORMATION: Description of Artificial Sequence: Synthetic -continued oligonucleotide

<400> SEQUENCE: 46
ctgcctaagg cggatttgaa t                                              21

<210> SEQ ID NO 47
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
ttauuccuuc uucgggaagu c                                              21

<210> SEQ ID NO 48
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
aaccttctgg aacccgccca c                                              21

<210> SEQ ID NO 49
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
gagcatcttc gagcaagaa                                                 19

<210> SEQ ID NO 50
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
catgtggcac cgtttgcct                                                 19

<210> SEQ ID NO 51
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
aactaccaga aaggtatacc t                                              21

<210> SEQ ID NO 52
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:

```
<223> OTHER INFORMATION: Description of Combined DNA/RNA Molecule:
      Synthetic oligonucleotide

<400> SEQUENCE: 52
ucacaguguc cuuuauguau t                                              21

<210> SEQ ID NO 53
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 53
gcaugaaccg gaggcccaut t                                              21

<210> SEQ ID NO 54
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
ccggacagtt ccatgtata                                                 19

<210> SEQ ID NO 55
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Asn Tyr Gly Met Asn
1               5

<210> SEQ ID NO 56
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Trp Ile Asn Thr Tyr Thr Arg Glu Pro Thr Tyr Ala Asp Asp Phe Lys
1               5                   10                  15

Gly

<210> SEQ ID NO 57
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Asp Ile Thr Ala Val Val Pro Thr Gly Phe Asp Tyr
1               5                   10
```

```
<210> SEQ ID NO 58
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Arg Ala Ser Glu Asn Ile Tyr Ser Asn Leu Ala
1               5                   10

<210> SEQ ID NO 59
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Ala Ala Ser Asn Leu Ala Asp
1               5

<210> SEQ ID NO 60
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Gln His Phe Trp Thr Thr Pro Trp Ala
1               5
```